US008975026B2

(12) United States Patent
Zichi et al.

(10) Patent No.: US 8,975,026 B2
(45) **Date of Patent: *Mar. 10, 2015**

(54) METHOD FOR GENERATING APTAMERS WITH IMPROVED OFF-RATES

(75) Inventors: Dominic Zichi, Boulder, CO (US); Sheri K. Wilcox, Longmont, CO (US); Chris Bock, Denver, CO (US); Daniel J. Schneider, Arvada, CO (US); Bruce Eaton, Longmont, CO (US); Larry Gold, Boulder, CO (US); Thale C. Jarvis, Boulder, CO (US); Jeffrey D. Carter, Longmont, CO (US)

(73) Assignee: SomaLogic, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/382,493

(22) PCT Filed: Jul. 9, 2010

(86) PCT No.: PCT/US2010/041540

§ 371 (c)(1),
(2), (4) Date: Jan. 5, 2012

(87) PCT Pub. No.: WO2011/006075

PCT Pub. Date: Jan. 13, 2011

(65) Prior Publication Data

US 2012/0115752 A1 May 10, 2012

Related U.S. Application Data

(63) Continuation-in-part of application No. 12/499,967, filed on Jul. 9, 2009, now Pat. No. 7,964,356, which is a continuation-in-part of application No. 12/175,434, filed on Jul. 17, 2008, now Pat. No. 7,947,447, and a continuation-in-part of application No. 11/623,580, filed on Jan. 16, 2007, now abandoned.

(60) Provisional application No. 60/950,281, filed on Jul. 17, 2007, provisional application No. 60/950,293, filed on Jul. 17, 2007, provisional application No. 60/950,283, filed on Jul. 17, 2007, provisional application No. 61/031,420, filed on Feb. 26, 2008, provisional application No. 61/051,594, filed on May 8, 2008.

(51) Int. Cl.
*C12N 15/115* (2010.01)

(52) U.S. Cl.
USPC ......... 435/6.11; 424/9.1; 435/91.1; 536/23.1; 536/24.3

(58) Field of Classification Search
USPC ......... 435/6, 91.1, 91.5, 6.11; 536/23.1, 24.3, 536/24.5; 935/77, 78; 424/9.1
See application file for complete search history.

(56) References Cited

U.S. PATENT DOCUMENTS

| | | | | |
|---|---|---|---|---|
| 4,562,157 | A | | 12/1985 | Lowe et al. |
| 4,737,453 | A | | 4/1988 | Primus et al. |
| 4,752,566 | A | | 6/1988 | Collins et al. |
| 5,000,000 | A | * | 3/1991 | Ingram et al. ................ 435/161 |
| 5,124,246 | A | | 6/1992 | Urdea et al. |
| 5,270,163 | A | | 12/1993 | Gold et al. |
| 5,412,087 | A | | 5/1995 | McGall et al. |
| 5,475,096 | A | | 12/1995 | Gold et al. |
| 5,567,588 | A | | 10/1996 | Gold et al. |
| 5,580,737 | A | | 12/1996 | Polisky |
| 5,582,981 | A | | 12/1996 | Toole et al. |
| 5,599,720 | A | | 2/1997 | Ekins |
| 5,614,503 | A | | 3/1997 | Chaudhary et al. |
| 5,639,868 | A | | 6/1997 | Janjic et al. |
| 5,645,985 | A | | 7/1997 | Froehler |
| 5,658,738 | A | | 8/1997 | Nadeau et al. |
| 5,681,697 | A | | 10/1997 | Urdea et al. |
| 5,688,935 | A | | 11/1997 | Stephens et al. |
| 5,712,375 | A | | 1/1998 | Jensen et al. |
| 5,719,273 | A | | 2/1998 | Tu et al. |
| 5,750,342 | A | | 5/1998 | Stephens et al. |

(Continued)

FOREIGN PATENT DOCUMENTS

| | | |
|---|---|---|
| EP | 0310251 | 4/1989 |
| GB | 2 183 661 | 6/1987 |
| WO | WO 89/06694 | 7/1989 |
| WO | WO 92/14842 | 3/1992 |
| WO | WO 92/14843 | 9/1992 |
| WO | WO 94/06934 | 3/1994 |
| WO | WO 98/33941 | 8/1998 |
| WO | WO 2001/009159 | 2/2001 |
| WO | WO 2001/061037 | 8/2001 |
| WO | WO 02/44726 | 6/2002 |

(Continued)

OTHER PUBLICATIONS

Bock et al., Proteomics, vol. 4, pp. 609-618 (2004).*

(Continued)

*Primary Examiner* — Jane Zara

(74) *Attorney, Agent, or Firm* — Swanson & Bratschun, L.L.C.

(57) ABSTRACT

The present disclosure describes the identification and use of aptamers and photoaptamers having slower dissociation rate constants than those obtained using previously described methods. Specifically, the present disclosure describes methods for the identification and use of aptamers to one or more targets within a histological or cytological sample, which have slow rates of dissociation. The aptamers may be used to assess localization, relative density, and presence or absence of one or more targets in cytological and histological samples. Targets may be selected that are specific and diagnostic of a given disease state for which the sample was collected. The aptamers may also be used to introduce target specific signal moieties. In addition to target identification, the aptamers may be used to amplify signal generation through a variety of methods.

29 Claims, 38 Drawing Sheets

(56) References Cited

U.S. PATENT DOCUMENTS

| | | | | |
|---|---|---|---|---|
| 5,756,291 | A | 5/1998 | Griffin et al. | |
| 5,763,177 | A | 6/1998 | Gold et al. | |
| 5,763,566 | A | 6/1998 | Jensen et al. | |
| 5,789,157 | A | 8/1998 | Jensen et al. | |
| 5,801,154 | A * | 9/1998 | Baracchini et al. | 514/44 A |
| 5,840,867 | A | 11/1998 | Toole et al. | |
| 5,843,653 | A | 12/1998 | Gold et al. | |
| 5,861,254 | A * | 1/1999 | Schneider et al. | 435/6.11 |
| 5,864,026 | A | 1/1999 | Jensen et al. | |
| 5,874,218 | A | 2/1999 | Drolet et al. | |
| 5,945,527 | A | 8/1999 | Tu et al. | |
| 5,958,691 | A | 9/1999 | Pieken | |
| 6,013,443 | A | 1/2000 | Heilig et al. | |
| 6,114,120 | A | 9/2000 | Jensen et al. | |
| 6,127,119 | A | 10/2000 | Stephens et al. | |
| 6,232,462 | B1 | 5/2001 | Collins et al. | |
| 6,376,474 | B1 | 4/2002 | Heilig et al. | |
| 6,613,526 | B2 | 9/2003 | Gold et al. | |
| 6,897,015 | B2 | 5/2005 | Henderson | |
| 7,855,054 | B2 | 12/2010 | Schneider | |
| 7,947,447 | B2 * | 5/2011 | Zichi et al. | 435/6.12 |
| 7,964,356 | B2 * | 6/2011 | Zichi et al. | 435/6.1 |
| 8,703,416 | B2 | 4/2014 | Sanders et al. | |
| 2002/0009767 | A1 | 1/2002 | Muraca | |
| 2002/0119473 | A1 | 8/2002 | Lupold | |
| 2003/0162216 | A1 | 8/2003 | Gold et al. | |
| 2003/0219801 | A1 | 11/2003 | Lipshutz | |
| 2003/0228603 | A1 | 12/2003 | Cload et al. | |
| 2004/0106145 | A1 | 6/2004 | Gold et al. | |
| 2004/0142384 | A1 | 7/2004 | Cohen et al. | |
| 2004/0176282 | A1 | 9/2004 | Dalby et al. | |
| 2004/0235053 | A1 | 11/2004 | Lam et al. | |
| 2005/0142582 | A1 | 6/2005 | Doyle et al. | |
| 2005/0158780 | A1 | 7/2005 | Lupold et al. | |
| 2005/0227225 | A1 | 10/2005 | Krevolin | |
| 2005/0288244 | A1 | 12/2005 | Manoharan et al. | |
| 2006/0057573 | A1 | 3/2006 | Gold et al. | |
| 2006/0105341 | A1 | 5/2006 | Krause et al. | |
| 2006/0105378 | A1 | 5/2006 | Hicke et al. | |
| 2006/0199213 | A1 | 9/2006 | Capodieci et al. | |
| 2007/0003950 | A1 | 1/2007 | Shen et al. | |
| 2007/0041901 | A1 | 2/2007 | Diener et al. | |
| 2007/0105142 | A1 | 5/2007 | Wilhelm | |
| 2007/0161015 | A1 | 7/2007 | Zheng et al. | |
| 2007/0166741 | A1 | 7/2007 | Heil et al. | |
| 2007/0166742 | A1 | 7/2007 | Gold et al. | |
| 2009/0004667 | A1 | 1/2009 | Zichi et al. | |
| 2009/0042206 | A1 | 2/2009 | Schneider et al. | |
| 2009/0306461 | A1 | 12/2009 | Oksenberg et al. | |
| 2010/0099149 | A1 | 4/2010 | Birnboim et al. | |
| 2010/0285479 | A1 * | 11/2010 | Jenison | 435/6 |
| 2010/0317120 | A1 | 12/2010 | Heil et al. | |
| 2011/0136099 | A1 | 6/2011 | Schneider et al. | |
| 2011/0245479 | A1 | 10/2011 | Zichi et al. | |
| 2012/0264117 | A1 | 10/2012 | Sanders et al. | |
| 2014/0058076 | A1 | 2/2014 | Rohloff et al. | |

FOREIGN PATENT DOCUMENTS

| | | | |
|---|---|---|---|
| WO | WO 2004/043996 | | 5/2004 |
| WO | WO 2006/063717 | * | 6/2006 |
| WO | WO 2011/006075 | | 1/2011 |
| WO | WO 2012/174496 | | 12/2012 |
| WO | WO 2013/185078 | | 12/2013 |

OTHER PUBLICATIONS

Brody et al., Molecular Diagnosis, vol. 4, No. 4, pp. 381-388 (1999).*

Latham et al., Nucleic Acids Research, vol. 22, No. 14, pp. 2817-2822 (1994).*

Brody et al, Molecular Diagnosis, vol. 4, No. 4, pp. 381-388 (1999).*

Bock et al, Proteomics, vol. 4, pp. 609-618 (2004).*

Structure search results re: Steutz et al (excerpted from WO 2006/063717), provided by PTO STIC services.*

Gold et al. (Dec. 7, 2010) PLOS ONE 5(12):e15004, "Aptamer-Based Multiplexed Proteomic Technology for Biomarker Discovery".

IPRP issued Jan. 19, 2012 in PCT/US2010/041540.

European Search Report issued Jul. 2, 2013 in EP Serial No. 10797920.5.

Gupta (May 2011) "Rapid histochemistry using slow off-rate modified aptamers with anionic competition" Applied Immunohistochemistry & Molecular Morphology: AIMM/Official Publication of the Society for Applied Immunohistochemistry 19(3):273-278.

Latham et al. (1994)Nucleic Acids Research 22(14):2817-2822, "The application of a modified nucleotide in aptamer selection: novel thrombin aptamers containing 5-(1-pentynyl)-2'-deoxyuridine".

Liu et al. (May 2012) PLOS ONE 7(5):1-10, "Selection of aptamers specific for adipose tissue".

Partial European Search Report issued Jul. 11, 2013 in EP 13164719.0.

Sekiya et al. (2005) Nucleic Acids Symposium 49:361-362 "In vitro selection of RNA aptamers against cellular and abnormal isoform of mouse prion protein".

Shaohua et al. (2009) Journal of Pathology 281:327-336, "Identification of an aptamer targeting nhRNP A1 by tissue slide-based SELEX".

Bigge and Mertes (1981) J. Org. Chem. 46(10): 1994-1997, "A palladium-catalyzed coupling reaction and a photolytic reaction for the direct synthesis of 5-arylpyrimidine nucleotides".

Bock et al. (Mar. 2004) Proteomics 4(3):609-618, "Photoaptmaer arrays applied to multiplexed proteomic analysis".

Brody et al. (1999) Molecular Diagnostics 4(4):381-388, "The Use of Aptamers in Large Arrays for Molecular Diagnostics".

Conklin et al. (Jan. 2002) Journal of Surgical Research 102(1):13-21, "Shear stress regulates occluding and VEGF expression in procine or arterial endothelial cells".

Daniels et al. (Dec. 23, 2003) PNAS 100(26):15416-15421, "A tenascin-C aptamer identified by tumor cell SELEX: Systematic evolution of ligands by exponential enrichment".

Davis et al. (1978) The Lancet 1:1185-1187, "Scintigraphic Detection of Atherosclerotic Lesions and Venous Thrombi in Man by Indium-111-Labeled Autologous Platelets".

Davis et al. (May 1980) Circulation 61:982-988, "Scintigraphic Detection of Carotid Atherosclerosis with Indium-111-Labeled Autologous Platelets".

Davis et al. (Sep. 3, 2002) PNAS, 99(18):11616-11621, "Isolation of high-affinity GTP aptamers from partially structured RNA libraries".

Dewey et al. (1995) J. Am. Chem. Soc. 117: 8474-8475, "New Uridine Derivatives for Systematic Evolution of RNA Ligands by Exponential Enrichment".

DiDonato (2006) "Dissertation. Part II. Synthesis and Evaluation of Modified Nucleotides for DNA Aptamer Selection" University of North Carolina, Raleigh 30-53.

Drabovich et al. (May 1, 2006) Analytical Chemistry 78(9):3171-3178, "Selection of smart aptamers by methods of kinetic capillary electrophoresis".

Drolet et al. (Aug. 1996) Nature Biotechnology 14(8):1021-1025, "An enzyme-linked oligonucleotide assay".

Ekins and Chu (Sep. 1997) JIFCC 9(3):100-109, "Immunoassay and Other Ligand Assays: Present Status and Future Trends".

Ellington & Szostak (1990) "Selection of RNAs with ligand-specific binding activity from pools of random sequence molecules" RNA Processing meeting abstract, p. 84.

EP Office Action issued Feb. 16, 2011 in European Application Serial No. 08782010.6.

EP Office Action issued Feb. 28, 2011 in European application serial No. 07718147.7.

EP Search report issued Dec. 1, 2009 in EP application serial No. 08782010.6.

EP Search report issued Feb. 22, 2010 in EP application serial No. 09012809.1.

Famulok and Szostak (1992) Angew. Chem. Int. Ed. Engl. 31(8): 979-988, "In Vitro Selection of Specific Ligand-binding Nucleic Acids".

Fischman et al. (1989) J. Nuc. Med. 30(6):1095-1100, "Radionuclide Imaging of Experimental Atherosclerosis with Nonspecific Polyclonal Immunoglobulin G".

(56) References Cited

OTHER PUBLICATIONS

Gebhardt et al. (Jun. 20, 2000) Biochemistry 39(24):7255-7265, "RNA aptamers to S-adenosylhomocysteine: kinectic properties, divalent cation dependency, and comparision with anti-S-adenosylhomocysteine antibody".
Ginsberg et al. (1990) Arteriosclerosis 10(2):256-262, "Noninvasive Imaging of $^{99m}$Technetium-Labeled Low Density Lipoprotein Uptake by Tendon Xanthomas in Hypercholesterolemic Patients".
Gold et al. (Jan. 1, 1995) Harvey Lectures 91:47-57, "The SELEX Process: A Surprising Source of Therapeutic and Diagnostic Compounds".
Gold et al. (Jan. 1995) Annual Review of Biochemistry 64:763-797, "Diversity of Oligonucleotide Functions".
IPRP issued Jan. 19, 2010 in PCT/US2008/070383.
Isaacsohn et al.(1986) Metabolism 35:364-366, "Adrenal Imaging With Technetium-99m-Labeled Low Density Lipoproteins".
ISR and Written Opinion mailed Dec. 17, 2008 in PCT/US2008/070383.
ISR and Written Opinion mailed Oct. 18, 2010 in PCT/US2010/041540.
Jellinek, et al. (Aug. 30, 1994) Biochemistry 33(34):10450-10456, "Inhibition of Receptor Binding by High-Affinity RNA Ligands to Vascular Endothelial Growth Factor".
Jhaveri et al. (Sep. 8, 1998) Bioorganic & Medicinal Chemistry Letters, 8(17):2285-2290, "In vitro selection of phosphorothiolated aptamers".
Joyce (1989) Gene 82:83-87, "Amplification, mutation and selection of catalytic RNA".
Joyce and Inoue (1989) Nucleic Acids Research 17(2): 711-722, "A novel technique for the rapid preparation of mutant RNAs".
Kang et al. (May 29, 2007) FEBS Letters, 581(13):2497-2502, "Combinatorial selection of a RNA thioaptamer that binds to Venezuelan equine encephalitis virus capsid protein".
Kawakami et al. (1997) Nucleic Acids Symposium Series No. 37:201-202, "Evolution of a phosphorothioate RNA library during in vitro selection".
Kinzler and Vogelstein (1989) Nucleic Acids Research 17(10): 3645-3653, "Whole genome PCR: application to the identification of sequences bound by gene regulatory proteins".
Kramer et al. (1974) J. Mol. Biol. 89: 719-736, "Evolution in vitro: sequence and phenotype of a mutant RNA resistant to ethidium bromide".
Langer et al. (Nov. 1981) Proc. Natl. Acad. Sci. USA,78(11):6633-6637, "Enzymatic synthesis of biotin-labeled polynucleotides: Novel nucleic acid affinity probes".
Lavitrano et al. (1992) Molecular Reproduction and Development 31:161-169, "The Interaction between Exogenous DNA and Sperm Cells".
Lees et al. (1983) J. Nuc. Med. 24:154-156, "External Imaging of Human Atherosclerosis".
Lees et al. (Sep.-Oct. 1, 1988) Arteriosclerosis 8:461-470, "Imaging Human Atherosclerosis with $^{99m}$Tc-Labeled Low Density Lipoproteins".
Levisohn and Spiegleman (1968) PNAS USA 60: 866-872, "The cloning of a self-replicating RNA molecule".
Levisohn and Spiegleman (1969) PNAS USA 63: 805-811, "Further extracellular Darwinian experiments with replicating RNA moleucles: diverse variants isolated under different selective conditions".
McGown et al. (Nov. 1995) Anal. Chem. 67:663A-668A, "The Nucleic Acid Ligand. A New Tool for Molecular Recognition".
Mettinger et al. (Feb. 1978)The Lancet 1:242-244, "Detection of Atherosclerotic Plaques in Carotid Arteries by the Use of $^{123}$I-Fibrinogen".
Minar et al. (Jan. 1989) Stroke 20(1):27-33, "Indium-111-Labeled Platelet Scintigraphy in Carotid Atherosclerosis".
Moerlein et al. (Feb. 1991) J. Nuc. Med. 32(2):300-307, "Metabolic Imaging with Gallium-68- and Indium-111-Labeled Low-Density Lipoprotein".
Office Action issued Feb. 23, 2011 in U.S. Appl. No. 12/859,930.
Oliphant and Struhl (1987) Methods in Enzymology 155: 568-582, "The use of random-sequence oligonucleotides for determining consensus sequences".
Oliphant and Struhl (1988) Nucleic Acids Research 16(15): 7673-7683, "Defining the consensus sequences of *E. coli* promoter elements by random selection".
Oliphant et al. (1986) Gene 44:177-183, "Cloning of random-sequence oligodeoxynucleotides".
Oliphant et al. (Jul. 1989) Mol. Cell. Biol. 9: 2944-2949, "Defining the sequence specificity of DNA-binding proteins by selecting binding sites from random-sequence oligonucleotides: analysis of yeast GCN4 protein".
Ord et al. (1992) Circulation 85:288-297, "Imaging of Thrombi With Tissue-Type Plasminogen Activator Rendered Enzymatically Inactive and Conjugated to a Residualizing Label".
Osborne et al. (1997) Current Opinion in Chemical Biology 1:5-9, "Aptamers as Therapeutic and Diagnostic Reagents: Problems and Prospects".
Pinkel et al. (Dec. 1988) Proc. Natl. Acad. Sci. USA 85:9138-9142, "Fluorescence in situ hybridization with human chromosome-specific libraries: Detection of trisomy 21 and translocations of chromosome 4".
Ramos-Vara, J. (2005) Vet. Pathol. 42:405-426, "Technical Aspects of Immunohistochemistry".
Roberts et al. (1983) J. Lipid Research 24:1160-1167 "Selective Accumulation of Low Density Lipoproteins in Damaged Arterial Wall".
Robertson and Joyce (Mar. 1990) Nature 344: 467-468, "Selection in vitro of an RNA enzyme that specifically cleaves single-stranded DNA".
Seelig and Jaschke (1997) Tetrahedron Letters, 38(44):7729-7732, "Site-Specific Modification of Enzymatically Synthesized RNA: Transcription Initiation and Diels-Adler Reaction".
Syvanen et al. (1986) Nucleic Acid Research, 14(12):5037-5048, "Fast quantification of nucleic acid hybrids by affinity-based hybrid collection".
Szostak (1988) Redesigning the Molecules of Life, (S.A. Benner ed.) Springer-Verlag Berlin Heidelberg, pp. 87-113.
Tarasow (1998) Nucleic Acid Sciences 48(1):29-37, "Dressed for Success" Realizing the Catalytic Potential of RNA.
Thiesen and Bach (Jun. 1990) Nucleic Acids Res. 18(11): 3203-3209, "Target detection assay (TDA): a versatile procedure to determine DNA binding sites as demonstrated on SP1 protein".
Tsai and Keene (Feb. 1993) J. Immunol. 150(3):1137-1145", In Vitro Selection of RNA Epitopes Using Autoimmune Patient Serum".
Tuerk and Gold (Aug. 1990) Science 249: 505-510, "Systematic evolution of ligands by exponential enrichment: RNA ligands to bacteriophage T4 DNA polymerase".
Tuerk et al. (Aug. 1992) Proc. Natl. Acad. Sci. USA 89:6988-6992, "RNA pseudoknots that inhibit human immunodeficiency virus type 1 reverse transcriptase".
Zichi et al. (Mar. 7, 2008) Current Opinion in Chemical Biology 12(1):78-85, "Proteomics and diagnostics: Let's Get Specific, again".
Vaught et al. (Mar. 2010) J.Am. Chem. Soc. ePub, 132(12):4141-4151:4142, "Expanding the Chemistry of DNA for in Vitro Selection".
Vaught, Jonathan David, Thesis Oct. 2008, "Enhancing the Functionality of Nucleic Acids".
Ito et al. (2003) Nucleic Acids Research 31(10):2514-2523, "Synthesis, thermal stability and resistance to enzymatic hydrolysis of the oligonucleotides containing 5-(*N*-aminohexyl)carbamoy1-2'-*O*-methylurindines".
Nomura et al. (1997) Nucleic Acids Research 25(14):2784-2791, "Site-specific introduction of functional groups into phosphodiester oligodeoxynucleotides and their thermal stability and nuclease-resistance properties".
Srisawat et al. (2001) Nucleic Acids Research 29(2):1-5 "Sephadex-binding RNA ligands: rapid affinity purification of RNA from complex RNA mixtures".
Ueno et al. (1997) Nucleic Acids Research 25(19):3777-3782, "Effects of 5-(*N*-aminohexyl)carbamoyl-2'-deoxyuridine on endonuclease stability and the ability of oligodeoxynucleotide to activate RNase H".

* cited by examiner

FIG.1

Histology Stains

| Stain | Materials Stained/Color | Site Stained/Color | Notes |
|---|---|---|---|
| Haematoxylin | Nucleic acids/blue; ER/blue | Nucleus/blue | |
| Eosin | Elastic fibers/pink; Reticular fibers/pink | Cytoplasm/pink; RBC/orange-red; Collagen/pink | Similar Dye analine blue |
| Toluidine blue | Mast cells granule/purple | Nucleus/blue; Cytoplasm/blue; RBC/blue; Collagen/blue | Similar dye methylene green |
| Masson's trichrome stain | Cartilage/blue-green ; Muscle fibers/red | Nucleus/black; Cytoplasm/red-pink; RBC/red; Collagen/blue-green | |
| Mallory's trichrome stain | Keratin/orange ; Cartilage/blue; Bone matrix/deep blue; Muscle fibers/red | Nucleus/red; Cytoplasm/ pale red; RBC/orange; Collagen/deep blue | |
| Weigert's elastic stain | Elastic fibers/blue-black | Nucleus/blue-black | |
| Heidenhains'azan trichrome stain | Muscle fibers/red; Cartilage/blue; Bone matrix/blue | Nucleus/red-purple; Cytoplasm/pink; RBC/red; Collagen/blue | Distinguishing cells from extracellular components |
| Silver stain | Reticular fibers/brown-black ; Nerve fibers/brown-black | | Reticular fibers, nerve fibers, fungi |
| Wright's stain | Granules/purple-pink ; Eosinophil granules/bright red-orange; Basophil granules/deep purple-violet; Platelet granules/red-purple | Nucleus/bluish-purple; Cytoplasm/bluish-gray; RBC/red-pink | Blood cells |
| Orcein stain | Elastic fibers/dark brown; Mast cells granules/purple; Smooth muscle/light blue | Nucleus/deep blue [or red]; RBC/bright red; Collagen/pink | |
| Periodic acid-Schiff stain (PAS) | Glycogen and other carbohydrates/magenta | Nucleus/blue; Collagen/pink | Basement membrane, carbohydrates |
| Acid Fast | Mycobacterium/red | | |
| Alcian Blue Stain | Polysaccharides/blue – blue green | Nucleus/black | Glycosaminoglycan analysis |
| Bielschowsky Stain | Neurofibrillary tangles/black; Senile plaques/brown | | |

FIG.1 Cont'd

| | | | |
|---|---|---|---|
| Congo Red | Amyloid/pink – red | | Apple green birefringence |
| Luxol Fast Blue Stain | Myelin sheath/ blue- blue purple; Nissl substance/red | | |
| Mucicarmine Stain | Epithelial mucin/red | | |
| Phosphotungstic Acid Haematoxylin Stain | Muscle /blue – black; Striations/dark brown; Connective Tissue/pale orange to pink to brownish red; Fibrin neuroglia/deep blue; Coarse elastic fibers/purple; Cartilage/bone/yellowish to brownish red | | CNS analysis |
| Osmium tetroxide | Lipids/black | | |
| VonGieson | Muscle/yellow; Connective tissue/red | | |

Template 1

5'-ABABGTCTTCTTGTCGTTTCGC-(N)40-GGTGGAGTGTGGTGAGG-3'

(SEQ ID NO:1)

Forward PCR Primer 1

5'-ATATATATCCTCACCACACTCCACC-3' (SEQ ID NO:2)

Reverse PCR Primer 1

5'-ABABTTTTTTTTGTCTTCTTGTCGTTTCGC-3' (SEQ ID NO:3)

Template 2

5'-ABABCCGTCCTCCTCTCCGTC-(N)40-GGGACACTGGGTGCAGG-3'

(SEQ ID NO:4)

Forward PCR Primer 2

5'-ATATATATCCTGCACCCAGTGTCCC-3' (SEQ ID NO:5)

Reverse PCR Primer 2

5'-ABABTTTTTTTTCCGTCCTCCTCTCCGTC-3' (SEQ ID NO:6)

(His)6-complement Oligonucleotide

5'-GTCTTCTTGTCGTTTCGC-3' (SEQ ID NO:7)

FIG. 3

Template 1

5'-ABABCCCGCTCGTCGTCTG-(N)40-CAGGCAGACGGTCACTC-3'

(SEQ ID NO:8)

Forward BrdU Primer 1

5'-BrdU - ATATATATGAGTGACCGTCTGCCTG-3' (SEQ ID NO:9)

Forward ANA Primer 1

5'- ANA - ATATATATGAGTGACCGTCTGCCTG-3' (SEQ ID NO:10)

Forward AQ Primer 1

5'- AQ - ATATATATGAGTGACCGTCTGCCTG-3' (SEQ ID NO:11

Forward Psor Primer 1

5'- Psor - ATATATATGAGTGACCGTCTGCCTG-3' (SEQ ID NO:12)

Forward PCR Primer 1

5'-ATATATATGAGTGACCGTCTGCCTG-3' (SEQ ID NO:13)

Reverse Primer 1

5'-TTTTTTTTCCCGCTCGTCGTCTG-3' (SEQ ID NO:14)

Reverse PCR Primer 1

5'-ABABTTTTTTTTCCCGCTCGTCGTCTG-3' (SEQ ID NO:15)

FIG. 5A

Template 2

5'-ABABGTGTCTGTCTGTGTCCTC-(N)40-GGTGGAGTGTGGTGAGG-3'

(SEQ ID NO:16)

Forward BrdU Primer 2

5'- BrdU - ATATATATCCTCACCACACTCCACC-3' (SEQ ID NO:17)

Forward ANA Primer 2

5'- ANA - ATATATATCCTCACCACACTCCACC-3' (SEQ ID NO:18)

Forward AQ Primer 2

5'- AQ - ATATATATCCTCACCACACTCCACC-3' (SEQ ID NO:19)

Forward Psor Primer 2

5'- Psor - ATATATATCCTCACCACACTCCACC-3' (SEQ ID NO:20)

Forward PCR Primer 2

5'-ATATATATCCTCACCACACTCCACC-3' (SEQ ID NO:21)

Reverse Primer 2

5'-TTTTTTTTGTGTCTGTCTGTGTCCTC-3' (SEQ ID NO:22)

Reverse PCR Primer 2

5'- ABABTTTTTTTTGTGTCTGTCTGTGTCCTC-3' (SEQ ID NO:23)

FIG. 5B

Anthraquinone (AQ)
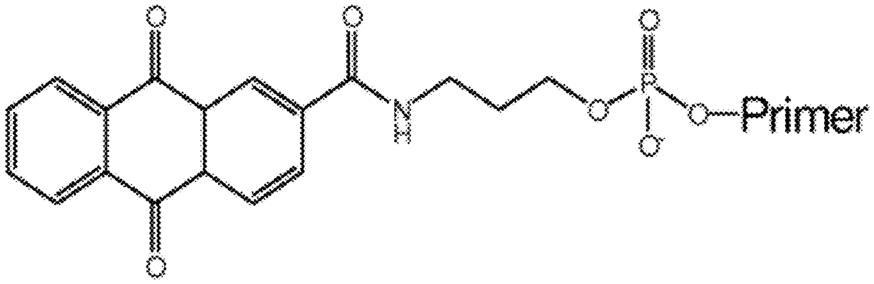
Psoralen (Psor)
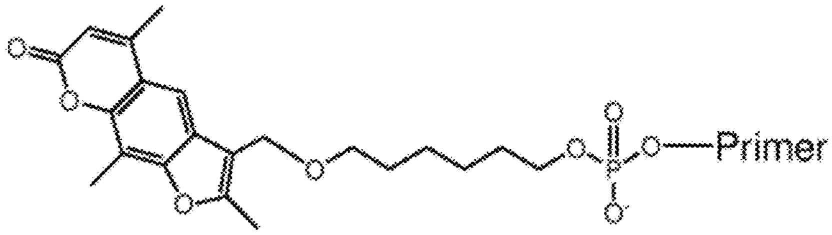
FIG. 6

4-Azido-2-nitro-aniline (ANA)

FIG 8

4-1BB
4-1BB ligand
6Ckine
α-1-Antichymotrypsin
α-2-Antichymotrypsin
ACE2
Activated Protein C
Activin A
Activin R1A
Activin R1B
ADAMTS - 4
ASAMTS - 5
Aggrecan
AIF
ALCAM
ALK-1
Alkaline phosphatase, tissue
AMPM2
Amyloid precursor protein
Angiogenin
Angiopoietin -1
Angiopoietin - 2
Angiopoietin - 4
ANGL3
ANGL4
Apo A -1
Apo B
Apo E
Apo E2
Apo E3
Apo E4
APRIL
AREG
ARGB
ARSB
ART
Artemin
ASAH2
ASAHL
ATN1
ATX13
Aurora Kinase A
Azurocidin
B7
B7-2
BAFF
BCAM
β-Catenin
Bcl-2
BCMA
BDNF
β-Endorphin
bFGF
bFGF-R
BGH3
β-Glucuronidase
BGN
BLC
BMP-7
BMP-14
BMPER
BMPR1A
BMP RII
β NGF
Bone proteoglycan II
BPI
C1q
C1r
C2
C3
C3a
C3adesArg
C3b
C3d
C4
C4b
C5
C5a
C5b, 6 Complex
C6
C7
C8
C9
Cadherin E
Cadherin 5
Calcineurin B α
Calpain I
Calpastatin
Carbonic Anhydrase IV
Cardiotrophin - 1
Caspase-3 (pro)
Catalase
Cathepsin A
Cathepsin B
Cathepsin D
Cathepsin G
Cathepsin S
Cathepsin V
CCL28
CD30L
CD22
CD27
CD30
CD40 Ligand
CD58 ANTIGEN
CD59
CD97
CD109
Ceruloplasmin
CFD
CK1
Ck β-8-1
CK-BB
CK-MM
CLF-1/CLC Complex
[illegible]
CNTF
CNTFR alpha
CNTN2
Coagulation Factor α-XIIa
Coagulation Factor IX
Coagulation Factor IXab
Coagulation Factor V
Coagulation Factor VII
Coagulation Factor X
Coagulation Factor Xa

FIG. 8 Cont'd

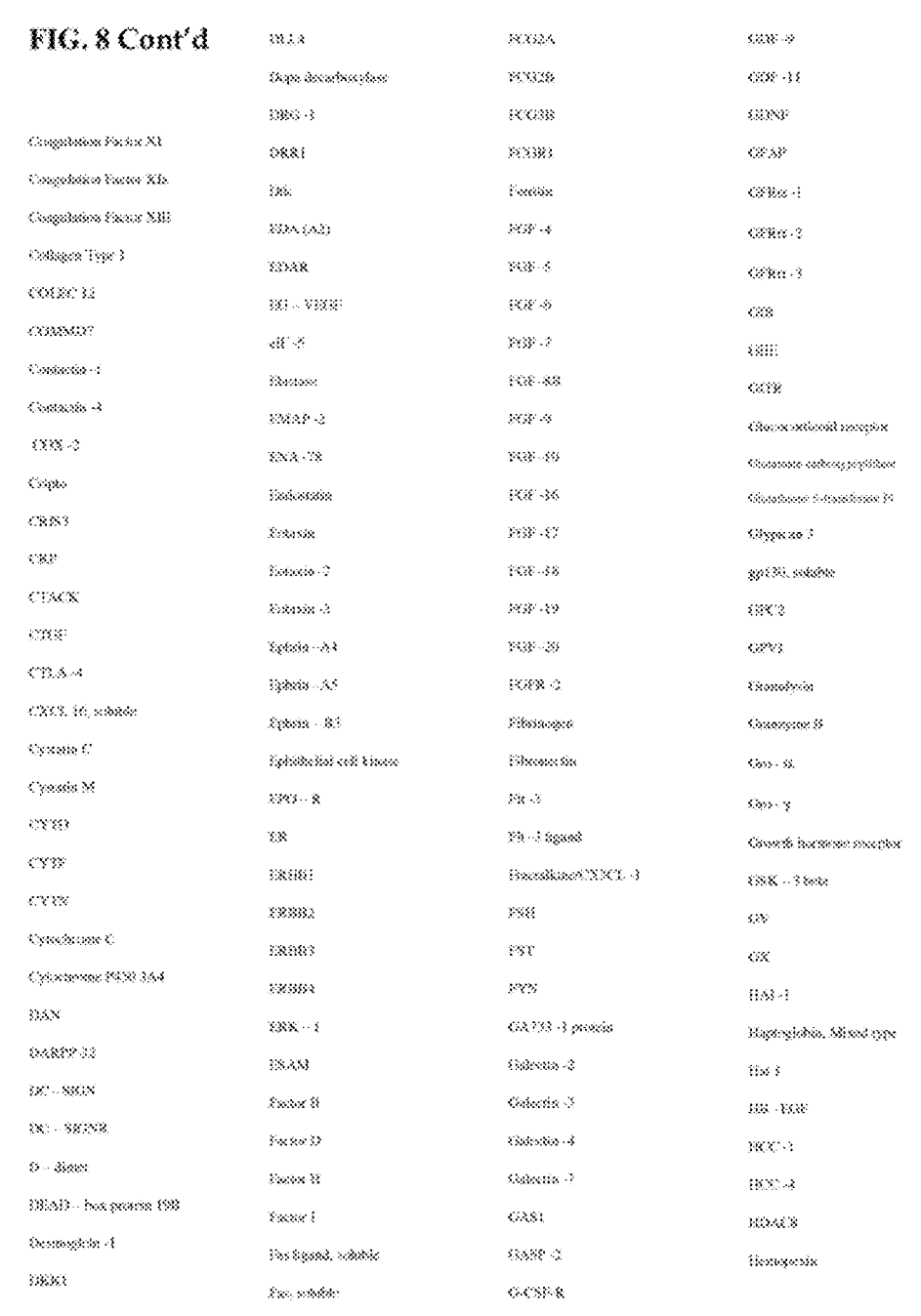

Coagulation Factor XI
Coagulation Factor XIa
Coagulation Factor XIII
Collagen Type I
COLEC12
COMMD7
Contactin-1
Contactin-4
COX-2
Cripto
CRIS3
CRP
CTACK
CTGF
CTLA-4
CXCL16, soluble
Cystatin C
Cystatin M
CYR61
CYTF
CYTN
Cytochrome C
Cytochrome P450 3A4
DAN
DARPP-32
DC-SIGN
DC-SIGNR
D-dimer
DEAD-box protein 19B
Desmoglein-1
DKK1
DLL4
Dopa decarboxylase
DBG-3
DRR1
Dtk
EDA (A2)
EDAR
EG-VEGF
eIF-5
Elastase
EMAP-2
ENA-78
Endostatin
Eotaxin
Eotaxin-2
Eotaxin-3
Ephrin-A4
Ephrin-A5
Ephrin-B3
Epithelial cell kinase
EPO-R
ER
ERBB1
ERBB2
ERBB3
ERBB4
ERK-1
ESAM
Factor B
Factor D
Factor H
Factor I
Fas ligand, soluble
Fas, soluble
FCG2A
FCG2B
FCG3B
FCGR1
Fetuin
FGF-4
FGF-5
FGF-6
FGF-7
FGF-8B
FGF-9
FGF-10
FGF-16
FGF-17
FGF-18
FGF-19
FGF-20
FGFR-2
Fibrinogen
Fibronectin
Flt-3
Flt-3 ligand
Fractalkine/CX3CL-1
FSH
FST
FYN
GA733-1 protein
Galectin-2
Galectin-3
Galectin-4
Galectin-7
GAS1
GASP-2
G-CSF-R
GDF-9
GDF-11
GDNF
GFAP
GFRα-1
GFRα-2
GFRα-3
GH
GHR
GITR
Glucocorticoid receptor
Glutamate carboxypeptidase
Glutathione S-transferase Pi
Glypican 3
gp130, soluble
GPC2
GPV1
Granulysin
Granzyme B
Gro-α
Gro-γ
Growth hormone receptor
GSK-3 beta
GV
GX
HAI-1
Haptoglobin, Mixed type
Hat 1
HB-EGF
HCC-1
HCC-4
HDAC8
Hemopexin

FIG. 8 Cont'd

Heparin cofactor II
HGF
Histone H1.2
HIV-1 Rev
HMG-1
HO-1
HPLN1
HPV E7 Type16
HPV E7 Type18
HSP 60
HSP 70
HSP 90α
HSP 90β
HTRA2
HVEM
H1KA
I12R2
I-309
IC3b
ICOS
IDE
IDS
IDUA
IFN-γ
IFN-γ R1
IFN-lambda 1
IFN-lambda 2
IgE
IGFBP-1
IGFBP-2
IGFBP-3
IGFBP-4
IGFBP-5
IGFBP-6
IGFBP-7
IGF-1
IGF-1 sR
IGF-II receptor
IgM
IL-1β
IL-1R AcP
IL-1R4
IL-1 sRI
IL-1F7
IL-1Rrp2
IL-2
IL-2 sRγ
IL-4
IL-4 sR
IL-6
IL-6 sRγ
IL-7
IL-7 R alpha
IL-8
IL-10
IL-10 Rβ
IL-11
IL-12
IL-12Rβ1
IL-13
IL-13 Rα1
IL-13 Rα2
IL-15 Rα
IL-16
IL-17 sR
IL-17B
IL-17D
IL-17E
IL-17F
IL-18 Bpa
IL-18 Rα
IL-18 Rβ
IL-19
IL-20
IL-21 sR
IL-22
IL-27
Inosine triphosphatase
IP-10
IR
I-TAC
JAM-B
JAM-C
Kallikrein 4
Kallikrein 5
Kallikrein 8
Kallikrein 11
Kallikrein 12
Kallikrein 13
Karyopherin-α2
Kininogen, HMW, Single Chain
Kininogen, HMW, Two Chain
KLB
KREM2
Ku70
Lactoferrin
LAG-3
Laminin
Layilin
LBP
LD78-beta
Leptin
Lipocalin 2
LKHA4
LRIG3
LRP6
LSAMP
Luteinizing hormone
LY86
LY9
Lymphotactin
Lymphotoxin β R
Lysozyme
LYVE-1
Macrophage mannose receptor
MAPK14
MATN2
MATN3
MBL
MCP-1
MCP-2
MCP-3
MCP-4
M-CSF R
MDC
MEK1
MEPE
MER
Met
METAP1
MIA
MICA

FIG. 8 Cont'd

Midkine
Mil4gd, Mouse
MIG
Mim, Rat
MIP-1α
MIP-1β
MIP-3α
MIP-3β
MKD1
MMP-1
MMP-2
MMP-3
MMP-7
MMP-8
MMP-9
MMP-13
MMP-14
MMP-17
MOZ
MP 032
MPIF-1
MSP R
Myeloperoxidase
Myosin regulatory light chain 2
NADPH-P450 Oxidoreductase
NANOG
NAP-2
NCAM-L1
NET3
NEUREGULIN-1
Neurotrophin-3
Neurotrophin-5
NG36
Nidogen
NKG2D
NKp30
NKp44
Noggin
Nogo Receptor
NovH
NPS-PLA2
NRP1
OLR1
OM
OPG
OSM
OX40 Ligand
PAFAH beta subunit
PAI-1
PAPP-A
PARC
Pattern protein A
Pattern protein B
P-Cadherin
PCNA
PDGF Rb
PDGF-AA
PD-L2
PDPK1
PECAM-1
Persephin
PF-4
PGRP-S
PIGR
PKR
PKC-α
PKC-β-II
PKCD
PKC-ζ
Plasmin
Plasminogen
PlGF
Prekallikrein
PRL
Properdin
Prostatic acid phosphatase
Protease nexin I
Protein C
Protein S
Prothrombin
PSA
PSA-ACT
P-Selectin
PSMA
PTHrP
PTN
PTP-1 B
Rab GDP dissociation factor β
Rac1
RAD51
RANTES
RAP
RELT
Resistin
RET
RGMB
RGM-C
S100A4
SAP
SARP-2
sCD14
SCF sR
SCGF-α
SCGF-β
Semaphorin 3A
sE-Selectin
SET9
sFRP-3
sICAM-1
sICAM-3
SIGIRR
Siglec-6
Siglec-7
Siglec-9
SLAMF8
sLeptin R
SLPI
sL-Selectin
SMAC
sn-1,2-Diacylglycerol Kinase
SOD
Soggy-1
Sonic Hedgehog
SPIN T2
Spondin-1
sRage
sRANKL
sTie-1
sTie-2
sTREM-1
STX1α

FIG. 8 Cont'd

Sulfotransferase, Nod Factor
SurFac
TACI
TARC
tau
TBP
TECK
Tenascin
Testican-2
TF
TFPI
TGF-β1
TGF-β2
TGF-β RIII
Thrombin
Thyroxine-Binding Globulin
TIE-2
TIMP-1
TIMP-2
TIMP-3
TNF sR-I
TNF sR-II
TNFSF 15
TNFSF 18
Tom34
Topoisomerase
tPA
Tpo
TRAIL
TRAIL R2
TRAIL R4
Transferrin
TrATPase
TrKB
TrKC
Troponin I
Troponin T
Trypsin
Trypsin 2
TSLP
TSLP R
TSP2
TSP4
TWEAK
UBC9
Ubiquitin +1
ULBP-1
ULBP-2
ULBP-3
uPA
URB
VCAM-1
VEGF
VEGF sR2
VEGF sR3
Vitronectin
vWF
WFKN2
WIF-1
WISP-3
XEDAR
Yes PCB-sp-cy
Molecular Weight: 1729.78

Molecular Weight: 1784.71

GdmB-P-sp-cy photocleavable biotin

PCB-dS1-cy3

Molecular Weight: 1299.28

PCB-dS1-cy3

Molecular Weight: 1299.28

PCB-dS3-cy3

Molecular Weight: 1657.46

FIG. 11

A 5' - CY3 – APTAMER – 3'

B 5' - $(AB)_2$ – $(T)_8$ – PC - PRIMER – 3'

C 5' - ANA – PC – CY3 – APTAMER – 3'

D 5' - $(AB)_2$ – $(T)_8$ – PRIMER – 3'

Base = Uridine (U) or Cytidine (C) (attachment is to the 5-position)

Z = R plus $(CH_2)_n$ connecting group, where n=0-3

* Denotes point of attachment of the R group to $(CH_2)_n$

FIG.20A

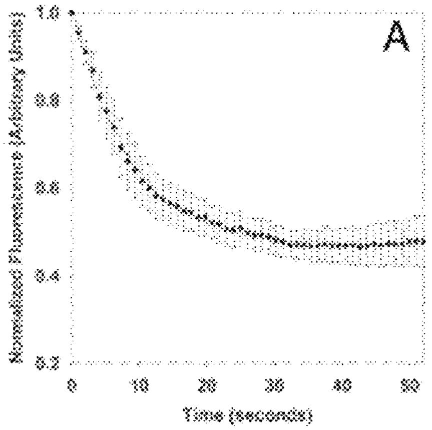

FIG.20B

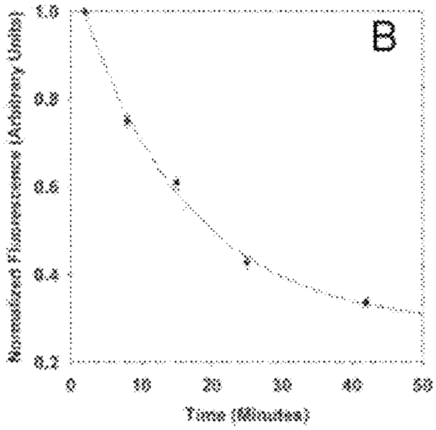

Nuclear fluorescence as HER2 SOMAmer is dissociated in the presence of 1 mM DS; data shown is mean +/- SD for n=5 nuclei, including the curve fit from nonlinear regression. Every fifth time point is shown for clarity. B) Membranous fluorescence as SOMAmers are dissociated in the presence of 1 mM DS and 100 nM nonfluorescent HER2 SOMAmer; data is mean +/- SD for n=5 regions of interest, including the curve fit from nonlinear regression.

FIG.22A
FIG.22B
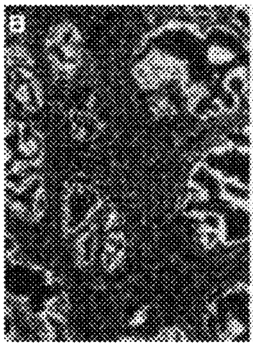
FIG.22C
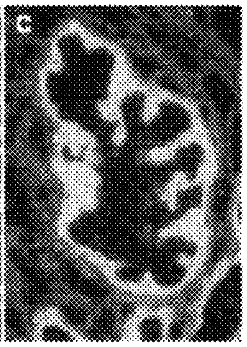
FIG.22D
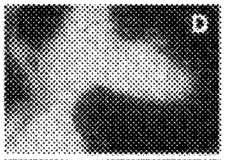
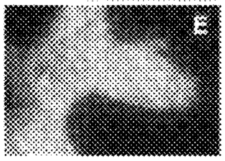
FIG.22E

METHOD FOR GENERATING APTAMERS WITH IMPROVED OFF-RATES

RELATED APPLICATIONS

This application is a continuation in part of U.S. application Ser. No. 12/499,967, filed Jul. 9, 2009, which is a continuation in part of U.S. application Ser. No. 12/175,434, filed Jul. 17, 2008, which claims priority to U.S. Provisional Application Ser. No. 60/950,281, filed Jul. 17, 2007, U.S. Provisional Application Ser. No. 60/950,293, filed Jul. 17, 2007, U.S. Provisional Application Ser. No. 60/950,283, filed Jul. 17, 2007, U.S. Provisional Application Ser. No. 61/031,420, filed Feb. 26, 2008 and U.S. Provisional Application Ser. No. 61/051,594, filed May 8, 2008. This application is also a continuation in part of U.S. application Ser. No. 11/623,580, filed on Jan. 16, 2007. Each of these applications is incorporated herein by reference in its entirety.

FIELD OF THE INVENTION

The present disclosure describes the identification and use of slow off-rate aptamers that are highly specific to one or more histological or cytological targets of interest. The disclosure describes the composition of these slow off-rate aptamers as well methods for their selection. The disclosure also describes aptamer constructs with improved functionalities for detection methods. Further, the disclosure describes applications enabled by these improved aptamers such as methods for improving identification of one or more specific markers in histological and/or cytological specimens using marker specific aptamers for the diagnosis of a disease state.

Incorporated by reference herein in its entirety is the Sequence Listing entitled "sequence Listing.txt", created Oct. 21, 2011, size of 5 kilobytes.

BACKGROUND

The following description provides a summary of information relevant to the present disclosure and is not a concession that any of the information provided or publications referenced herein is prior art to the claimed invention.

The SELEX process is a method for the in vitro selection of nucleic acid molecules that are able to bind with high specificity to target molecules and is described in U.S. Pat. No. 5,475,096 entitled "Nucleic Acid Ligands" and U.S. Pat. No. 5,270,163 (see also WO 91/19813) entitled "Nucleic Acid Ligands" each of which is specifically incorporated by reference herein. These patents, collectively referred to herein as the SELEX Patents, describe methods for making an aptamer to any desired target molecule.

The basic SELEX process has been modified to achieve a number of specific objectives. For example, U.S. Pat. No. 5,707,796, entitled "Method for Selecting Nucleic Acids on the Basis of Structure" describes the use of the SELEX process in conjunction with gel electrophoresis to select nucleic acid molecules with specific structural characteristics, such as bent DNA. U.S. Pat. No. 5,580,737, entitled "High-Affinity Nucleic Acid Ligands That Discriminate Between Theophylline and Caffeine" describes a method for identifying highly specific aptamers able to discriminate between closely related molecules, termed Counter-SELEX. U.S. Pat. No. 5,567,588, entitled "Systematic Evolution of Ligands by Exponential Enrichment: Solution SELEX" describes a SELEX-based method which achieves highly efficient partitioning between oligonucleotides having high and low affinity for a target molecule. U.S. Pat. No. 5,496,938, entitled "Nucleic Acid Ligands to HIV-RT and HIV-1 Rev" describes methods for obtaining improved aptamers after SELEX has been performed. U.S. Pat. No. 5,705,337, entitled "Systematic Evolution of Ligands by Exponential Enrichment: Chemi-SELEX" describes methods for covalently linking an aptamer to its target. U.S. Pat. No. 6,376,424, entitled "Systematic Evolution of Ligands by Exponential Enrichment: Tissue SELEX" describes methods to produce aptamers to cell or tissue specific markers without the purification of the specific marker.

The SELEX process encompasses the identification of high-affinity aptamers containing modified nucleotides conferring improved characteristics on the ligand, such as improved in vivo stability or improved delivery characteristics. Examples of such modifications include chemical substitutions at the ribose and/or phosphate and/or base positions. SELEX process-identified aptamers containing modified nucleotides are described in U.S. Pat. No. 5,660,985, entitled "High Affinity Nucleic Acid Ligands Containing Modified Nucleotides" that describes oligonucleotides containing nucleotide derivatives chemically modified at the 5'- and 2'-positions of pyrimidines. U.S. Pat. No. 5,580,737, see supra, describes highly specific aptamers containing one or more nucleotides modified with 2'-amino (2'-$NH_2$), 2'-fluoro (2'-F), and/or 2'-O-methyl (2'-OMe).

Further modifications of the SELEX process are described in U.S. Pat. No. 5,763,177, U.S. Pat. No. 6,001,577, and U.S. Pat. No. 6,291,184, each of which is entitled "Systematic Evolution of Nucleic Acid Ligands by Exponential Enrichment: Photoselection of Nucleic Acid Ligands and Solution SELEX"; see also, e.g., U.S. Pat. No. 6,458,539, entitled "Photoselection of Nucleic Acid Ligands". These patents, collectively referred to herein as "the PhotoSELEX Patents" describe various SELEX methods for selecting aptamers containing photoreactive functional groups capable of binding and/or photocrosslinking to and/or photoinactivating a target molecule. The resulting photoreactive aptamers are referred to as photocrosslinking aptamers or photoaptamers.

Although these SELEX and photoSELEX processes are useful, there is always a need for processes that lead to improved properties of aptamers generated from in vitro selection techniques. For example, a need exists for aptamers to target molecules with better binding affinities than those achieved with naturally occurring DNA or RNA nucleotides, as well as methods for producing such aptamers. For many applications, such as for example, in vitro assays, diagnostics, therapeutic, or imaging applications, it is of interest to produce aptamers with slow dissociation rates from the aptamer/target affinity complex. Several techniques have been proposed for producing such reagents (see, e.g., WO 99/27133 and US 2005/0003362). However, these selection processes do not discriminate between the selection of reagents that have fast association kinetics with the target (i.e., fast on-rates) and the selection of reagents that have slow dissociation kinetics with the target (i.e., slow off-rates). Thus, there is a need for novel processes and techniques that favor the selection of slow off-rate aptamers while inhibiting the selection of aptamers that simply have a fast association rate with the target.

Finally, there is a need for aptamer constructs that include different built-in functionalities. These functionalities may include tags for immobilization, labels for detection, means to promote or control separation, etc.

Cytology consists of the evaluation of cell morphology, structure, and substructure, and as a diagnostic tool can be applied to any bodily fluid or organ. Specimens may be cells released in a fluid such as urine, gastric, sputum, pleural, spinal fluid, effusions, etc. or may be collected by needle biopsy or aspiration, scraping, or cytological brush. Aspiration biopsy may be performed on the lymph nodes, thyroid, salivary glands, breast, endometrial, or prostate. Cytological evaluations are used to evaluate organelle pathology, cell death (necrosis, apoptosis), cellular injury and response, cell aging, amyloidosis, autoimmune diseases, and to discriminate cancer from other disease states.

Histology consists of the evaluation of tissue morphology and structure for the diagnosis of a disease state, with the identification of malignancy being largely based on histological information. There are four major tissue categories in the body—epithelial, connective, muscle, and nervous. Direct microscopic visualization of tissue features is difficult due to the thickness of the tissue sample. Therefore techniques have been developed to allow the production of thin, representative sections of the tissue sample for subsequent analysis. Histochemistry is the study of the chemical composition of cells and tissues, typically using specific staining reactions to identify and localize specific components.

Both cytology and histology samples have been evaluated with immunological reagents. Antibodies to specific markers have been used to introduce dyes or other signaling moieties for visualization. Frequently, the immunological methods are harsher than the standard methods because of the additional requirement to make the fixed sample permeable to the immunological reagents so the fixation method may be carefully balanced with the subsequent immunostaining to prevent the generation of artifacts. The size of the antibody limits diffusion into fixed cells and tissues. The $F_c$ portion of the antibody may non-specifically associate with cell or tissue structures to generate erroneous results.

Cytologists and histologist are currently being asked to increase the number and range of tests conducted on a single collected specimen. To accomplish these goals it would be advantageous to have reagents that could provide one or more of the following characteristics: (1) be applied sequentially to the same sample without significant sample damage; (2) be pre-labeled to reduce or eliminate multiple process steps; (3) be pre-labeled with a number of different dyes or detectable moieties that can simultaneously be detected for detection of multiple targets from a single section; (4) eliminate the need for the antigen retrieval process as described below; (5) reduce or eliminate the permeabilization process; (6) reduce or eliminate non-specific association with the non-target; (7) stabilize label location; and (8) diffuse rapidly through tissue to facilitate fast target staining. Slow off-rate aptamers could address any of these needs in addition to providing (1) a more consistent and reliable reagent because they are chemically synthesized; (2) chemically robust reagents that have reduced storage requirements; and (3) rapid and high-throughput discovery of binding reagents to target new proteins.

SUMMARY

The present disclosure describes novel aptamers, and methods to produce and use such aptamers. In particular, the disclosure describes slow off-rate (slow rate of dissociation) aptamers, slow off-rate aptamers containing C-5 modified pyrimidines, and processes for the selection of slow off-rate aptamers by dilution, by the addition of a competitor, or by a combination of both approaches. In addition, slow off-rate aptamers to various targets such as proteins and peptides are described. Slow off-rate aptamers with unique structural features and melting temperatures are also described. The disclosure also describes slow off-rate aptamers with photoreactive functional groups, aptamers that are refractory to the presence of poly-anionic materials, and a selection process for these aptamers, as well as aptamers constructed with a variety of other functionalities to improve their utility in various applications.

The present disclosure describes improved SELEX methods for generating aptamers that are capable of binding to one or more targets of interest. More specifically, the present disclosure describes methods for producing aptamers and/or photoaptamers having slower rates of dissociation from their respective targets than aptamers and photoaptamers obtained with previous SELEX methods. Generally, after contacting the candidate mixture with the target and allowing the formation of nucleic acid-target complexes to occur, a slow off-rate enrichment process is introduced wherein nucleic acid-target complexes with fast dissociation rates will dissociate and not reform, while complexes with slow dissociation rates will remain intact. Methods for introducing a slow off-rate enrichment process include, but are not limited to, adding competitor molecules to the mixture of nucleic acids and targets, diluting the mixture of nucleic acids and targets, or a combination of both of these. The disclosure further describes aptamers and photoaptamers obtained using these methods.

In one embodiment, the method comprises preparing a candidate mixture of nucleic acids; contacting the candidate mixture with a target wherein nucleic acids with the highest relative affinities to the target preferentially bind the target, forming nucleic acid-target complexes; introducing a slow off-rate enrichment process to induce the dissociation of nucleic acid-target complexes with relatively fast dissociation rates; partitioning the remaining bound nucleic acid-target complexes from free nucleic acids in the candidate mixture; and identifying the nucleic acids that were bound to the target. The process may further include the iterative step of amplifying the nucleic acids that bind to the target to yield a mixture of nucleic acids enriched with nucleic acids that bind to the target molecule yet produce nucleic acid-target molecule complexes having slow dissociation rates.

In another embodiment, the candidate mixture of nucleic acids includes nucleic acids containing modified nucleotide bases that may aid in the formation of modified nucleic acid-target complexes having slow dissociation rates. Improved methods for performing SELEX with modified nucleotides, including nucleotides which contain photoactive or other functional groups, or nucleotides which contain placeholders for photoactive groups are disclosed in U.S. application Ser. No. 12/175,388, filed Jul. 17, 2008, entitled "Improved SELEX and PHOTOSELEX," which is incorporated by reference herein in its entirety. Placeholder nucleotides may also be used for the mid-SELEX or post-SELEX introduction of modified nucleotides that are not photoreactive.

The various methods and steps described herein can be used to generate an aptamer capable of either (1) binding to a target or (2) binding to a target and subsequently forming a covalent linkage with the target upon irradiation with light in the UV or visible spectrum.

In another aspect, the various methods and steps described herein can be used to generate an aptamer capable of modifying the bioactivity of a target through binding and/or crosslinking to the target. In one embodiment, an aptamer to a unique target associated with or relevant to a specific disease process is identified. This aptamer can be used as a diagnostic reagent, either in vitro or in vivo. In another embodiment, an aptamer to a target associated with a disease state may be administered to an individual and used to treat the disease in vivo. The aptamers and photoaptamers identified herein can be used in any diagnostic, imaging, high throughput screening or target validation techniques or procedures or assays for which aptamers, oligonucleotides, antibodies and ligands, without limitation can be used. For example, aptamers and photoaptamers identified herein can be used according to the methods described in detail in U.S. application Ser. No. 12/175,446, filed Jul. 17, 2008, entitled "Multiplexed Analyses of Test Samples", which is incorporated by reference herein in its entirety.

Various embodiments describe the utility of slow off-rate aptamers for the identification and visualization of specific targets in cytological and/or histological samples and as histology/cytology reagents. In one embodiment, one or more slow off-rate aptamers are used in a cytological or histological evaluation of a cell or tissue sample to detect one or more potential targets in said cell or tissue sample. The cytological or histological evaluation comprises: a) obtaining a cell or tissue sample and dividing said sample into a plurality of cell sample aliquots or preparations or tissue sections; b) contacting a first cell sample preparation or tissue section with a solution comprising a slow off-rate aptamer to a target; c) optionally comparing the results obtained in step b) with a negative control prepared by reacting a second cell sample aliquot or tissue section with a solution as in step b) that lacks said slow off-rate aptamer; and d) detecting said slow off-rate aptamer as an indication of the presence or absence of said target.

In one embodiment, slow off-rate aptamers are selected for one or more targets from an optionally fixed cellular or tissue sample for use in that specific cell or tissue in a diagnostic application. Thus, the slow off-rate aptamers would specifically recognize the target in the fixed configuration (whether that is cross linked or otherwise modified) and in the cellular/tissue environment specific to the diagnosis to be made. Thus, no antigen retrieval process would be required.

In another embodiment, slow off-rate aptamers are produced with photoreactive or chemically reactive moieties that can be used to crosslink the slow off-rate aptamer (or aptamers) to its (their) specific target (targets) within in the cytological or histological sample. The ability to make a covalent linkage between the slow off-rate aptamer and the specific target may facilitate the retention of a target specific detectable moiety through the sample processing steps required with a histological or cytological preparation.

Other embodiments rely on slow off-rate aptamers that are substantially smaller than antibodies and should have improved dispersion capabilities in the cell or tissue sample. Still other embodiments rely on the elimination of multiple process steps that could reduce the damage done to cellular and tissue samples, and also substantially accelerate the staining process.

Yet more embodiments, involve analyzing multiple targets, with the corresponding specific slow off-rate aptamers, from a single slide that would reduce waste, processing time, time to results, and conserve original specimen for any subsequent testing needs or archival purposes. In some embodiments, these multiple slow off-rate aptamers are contacted with their corresponding target in a sequential manner. In other embodiments, these multiple slow off-rate aptamers are contacted with their corresponding target in a simultaneous manner. In one embodiment, the one or more slow off-rate aptamers are each produced with a different detectable moiety.

In another embodiment, the presence of one or more target(s) identified in a histological or cytological sample by the detection of a target specific slow off-rate aptamer may be used for the differentiation of type and origin of a suspected tumor. These targets may include tumor specific markers as well as tissue specific markers, like hormones or cytokeratins. In another embodiment, the presence of one or more target(s) identified in a histological or cytological sample by detection of a target specific slow off-rate aptamer may be used for the selection of appropriate therapeutic agents and to evaluate potential outcome.

In one embodiment, steps a) and b) of the cytological or histological evaluation may include one or more of the following steps: collecting a cell or tissue sample, fixing the cell or tissue sample, dehydrating, clearing, immobilizing the cell or tissue sample on a microscope slide, permeabilizing the cell or tissue sample, treating for antigen retrieval, staining, destaining, washing, and blocking. In one embodiment, the cell sample is produced from a cell block. In one embodiment, the fixing and dehydrating steps for the tissue sample are replaced with a freezing step.

In one embodiment, one or more slow off-rate aptamers are contacted with the histological or cytological sample before the staining step. In another embodiment, one or more slow off-rate aptamers containing detectable moieties/labels such as fluorophores or dyes are contacted with the histological or cytological sample in order to stain the target molecule.

In one embodiment, the one or more slow off-rate aptamers for use in the histological or cytological evaluation are mixed in a buffered solution that may further comprise blocking materials, competitors, detergents, stabilizers, carrier nucleic acid, polyanionic materials, etc.

In another embodiment, the one or more slow off-rate aptamers contacted with the histological or cytological sample may serve as the nucleic acid target in a nucleic acid amplification method. The nucleic acid amplification method may include PCR, q-beta replicase, rolling circle amplification, strand displacement, helicase dependent amplification, loop mediated isothermal amplification, ligase chain reaction, and restriction and circularization aided rolling circle amplification.

One embodiment describes a method for the diagnosis of a specific disease state said method comprising: a) obtaining a tissue or cell sample and dividing said sample into a plurality of tissue sections or cell preparations; b) contacting one of said tissue sections or cell preparations with a solution comprising one or more slow off-rate aptamers to one or more targets contained within said tissue or cell sample; c) optionally comparing the results obtained in step b) with a negative control prepared by contacting a second tissue section or cell preparation with a solution as in step b) that lacks said slow off-rate aptamer(s); d) optionally comparing the results obtained in step b) with a third tissue section or cell preparation prepared by staining said third tissue section or cell preparation for the morphological analysis appropriate to the tissue or cell type and disease state; and e) diagnosing said disease state.

In one embodiment, the one or more slow off-rate aptamers are produced with a detectable moiety and may be directly detected after reaction with their respective target or targets following an optional wash step to remove unreacted slow off-rate aptamer or slow off-rate aptamers. In other embodiments, the one or more slow off-rate aptamers interaction with their respective target or targets is detected after the two components of an element to support signal generation are reacted.

In another embodiment, the slow off-rate aptamers are selected, identified, produced, and/or synthesized using an optionally fixed tissue or cell specimen. Prior to the SELEX process, the fixed tissue may be treated to permeabilize sample membranes by methods equivalent to those used in the staining process. The method of fixation used in the SELEX process may be the same as the fixation method used on a tissue or cell sample in the actual histological/cytological procedure. The requirement is that the target that the slow off-rate aptamer is specific to be presented to the aptamer library in the selection process in the fixed configuration that will be present in the sample to be analyzed.

In another embodiment, the targets detected in the histological or cytological sample by the presence of its cognate slow off-rate aptamer may be used to guide the design of the therapeutic regimen or to predict the potential response to the therapeutic regimen available.

In one embodiment, kits for various histochemistry and cytology applications using aptamer reagents can be prepared based on the methods disclosed herein.

BRIEF DESCRIPTION OF THE FIGURES

FIG. 1 illustrates a number of different stains for histological slides, the material that is stained and the expected color of the stained material.

FIG. 3 illustrates representative aptamer template, primer, and complementary oligonucleotide sequences used in the disclosure. The oligonucleotides were prepared by standard solid-phase synthesis techniques. B=dT-biotin.

FIGS. 5A and 5B show oligonucleotides that were used to prepare the candidate mixtures or perform various steps in the selection process described in Example 2. The oligonucleotides were prepared by standard solid-phase synthesis techniques. BrdU (5-bromo-dUTP), anthraquinone (AQ), and psoralen (Psor) chromophores were purchased as phosphoramidites and added to the 5' terminus of the forward primer during synthesis. 4-Azido-2-nitro-aniline (ANA) was prepared as a para-nitro-phenyl carbonate derivative and coupled to a 5' hexylamine phosphoramidite after synthesis. Two candidate mixture sequences were used in this example, designated 1 and 2. B=dT-biotin. Template 1 (FIG. 5A) was only used with candidate mixtures containing 5'-BrdU, AQ, and ANA, and Template 2 (FIG. 5B) was only used with candidate mixtures containing 5'-Psor for Example 2.

FIG. 8 is a chart of over 500 targets for which aptamers have been identified. Many of these aptamers have been designed to have slow dissociation rates from their respective targets.

FIG. 11 illustrates the aptamer and primer constructs described in the disclosure. Cy3 represents a Cyanine 3 dye, PC a photocleavable linker, ANA a photoreactive crosslinking group, $(AB)_2$ a pair of biotin residues separated by dA residues, and $(T)_8$ a poly dT linker. Primer constructs are complementary to the complete 3' fixed region of the aptamer constructs.

FIG. 20A illustrates the nuclear fluorescence as HER2 SOMAmer is dissociated in the presence of 1 mM dextran sulfate. Data shown is mean+/−SD for n=5 nuclei, including the curve fit from nonlinear regression. Every fifth time point is shown for clarity. FIG. 20B illustrates membranous fluorescence as SOMAmers are dissociated in the presence of 1 mM dextran sulfate and 100 nM nonfluorescent HER2 SOMAmer. Data shown is mean+/−SD for n=5 regions of interest, including the curve fit from nonlinear regression.

FIG. 22A illustrates standard antibody immunofluorescence in human prostate tissue. FIG. 22B illustrates prostate tissue stained with 20 nM Qdot605-PSA aptamer+1 mM dextran sulfate, nuclei counterstained with DAPI. FIG. 22C illustrates aptamer staining of PSA in prostate tissue as in FIG. 22B, magnified, without DAPI counterstain. FIG. 22D illustrates prostate tissue as in FIGS. 22B and C with DAPI stain. FIG. 22E illustrates prostate tissue as in FIGS. 22B and C without DAPI stain.

DETAILED DESCRIPTION

Figure 2:
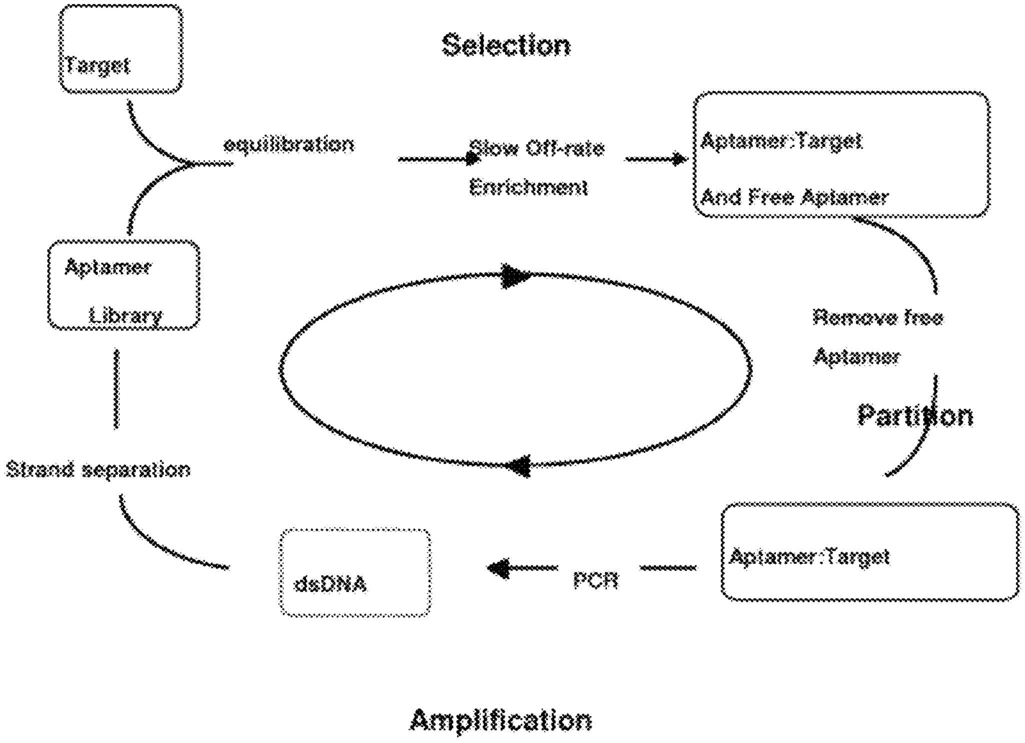
FIG. 2 illustrates an exemplary SELEX method which includes the step of incorporating a slow off-rate enrichment process.

The practice of the invention disclosed herein employs, unless otherwise indicated, conventional methods of chemistry, microbiology, molecular biology, and recombinant DNA techniques within the level of skill in the art. Such techniques are explained fully in the literature. See, e.g., Sambrook, et al. *Molecular Cloning: A Laboratory Manual* (Current Edition); *DNA Cloning: A Practical Approach*, vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition; Histology for Pathologists (S. E. Mills, Current Edition). All publications, published patent documents, and patent applications cited in this specification are indicative of the level of skill in the art(s) to which the invention pertains. All publications, published patent documents, and patent applications cited herein are hereby incorporated by reference to the same extent as though each individual publication, published patent document, or patent application was specifically and individually indicated as being incorporated by reference.

As used in this specification, including the appended claims, the singular forms "a," "an," and "the" include plural references, unless the content clearly dictates otherwise, and are used interchangeably with "at least one" and "one or more." Thus, reference to "an aptamer" includes mixtures of aptamers, reference to "a probe" includes mixtures of probes, and the like.

As used herein, the term "about" represents an insignificant modification or variation of the numerical values such that the basic function of the item to which the numerical value relates is unchanged.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but may include other elements not expressly listed or inherent to such process, method, product-by-process, or composition of matter.

As used herein, "nucleic acid ligand" "aptamer" and "clone" are used interchangeably to refer to a non-naturally occurring nucleic acid that has or may have a desirable action on a target molecule. A desirable action includes, but is not limited to, binding of the target, catalytically changing the target, reacting with the target in a way that modifies or alters the target or the functional activity of the target, covalently attaching to the target (as in a suicide inhibitor), and facilitating the reaction between the target and another molecule. In one embodiment, the action is specific binding affinity for a target molecule, such target molecule being a three dimensional chemical structure, other than a polynucleotide, that binds to the aptamer through a mechanism which is predominantly independent of Watson/Crick base pairing or triple helix binding, wherein the aptamer is not a nucleic acid having the known physiological function of being bound by the target molecule. Aptamers include nucleic acids that are identified from a candidate mixture of nucleic acids, the aptamer being a ligand of a given target, by the method comprising: (a) contacting the candidate mixture with the target, wherein nucleic acids having an increased affinity to the target relative to other nucleic acids in the candidate mixture may be partitioned from the remainder of the candidate mixture; (b) partitioning the increased affinity and/or slow off-rate nucleic acids from the remainder of the candidate mixture; and (c) amplifying the increased affinity, slow off-rate nucleic acids to yield a ligand-enriched mixture of nucleic acids, whereby aptamers to the target molecule are identified. It is recognized that affinity interactions are a matter of degree; however, in this context, the "specific binding affinity" of an aptamer for its target means that the aptamer binds to its target generally with a much higher degree of affinity than it binds to other, non-target, components in a mixture or sample. An "aptamer" or "nucleic acid ligand" is a set of copies of one type or species of nucleic acid molecule that has a particular nucleotide sequence. An aptamer can include any suitable number of nucleotides. "Aptamers" refer to more than one such set of molecules. Different aptamers may have either the same number or a different number of nucleotides. Aptamers may be DNA or RNA and may be single stranded, double stranded, or contain double stranded regions.

As used herein, "slow off-rate" or "slow rate of dissociation" or "slow dissociation rate" refers to the time it takes for an aptamers/target complex to begin to dissociate. This can be expressed as a half life, $t_{1/2}$, or the point at which 50% of the aptamer/target complex has dissociated. The off-rate or dissociation rate of a slow off-rate aptamer, expressed as $t_{1/2}$ values, can be ≥about 15 min., ≥about 30 min., ≥about 60 min., ≥about 90 min., ≥about 120 min. ≥about 150 min. ≥about 180 min. ≥about 210 min., and ≥about 240 min.

In one embodiment, a method for producing a synthetic library of nucleic acids comprises: 1) synthesizing the nucleic acids; 2) deprotecting the nucleic acids; 3) purifying the nucleic acids; and 4) analyzing the nucleic acids. In the synthesis step, a monomer mixture is prepared where the ratio of the various nucleotides in the mix is optimized to yield equal ratios of each nucleotide in the final product. One or more of the monomers in the mixture may comprise a modified nucleotide. Amidite protection groups are used in this procedure and in one embodiment, the monomer concentration is 0.1 M. During synthesis, the five prime protecting group is retained in the product nucleic acid. Synthesis is conducted on a solid support (controlled pore glass, CPG) and at least about 80 cycles are completed to synthesize the final product.

After the synthesis process, the nucleic acid product is deprotected. A 1.0 M aqueous lysine buffer, pH 9.0 is employed to cleave apurinic sites while the product is retained on the support (controlled pore glass, CPG). These cleaved truncated sequences are washed away with deionized (dI) water two times. 500 μL of dI water are added after the two washes in preparation for the deprotection step. This step involves the treatment with 1.0 mL of t-butylamine:methanol:water, 1:1:2, for 5 hours at 70° C., followed by freezing, filtration, and evaporation to dryness. The nucleic acid product is purified based on the hydrophobicity of the protecting group on a PRP-3 HPLC column (Hamilton). Appropriate column fractions are collected and pooled, desalted, and evaporated to dryness to remove the volatile elution buffers. The final product is washed with water by a centrifugation process and then re-suspended. Finally, the resuspended material is treated to deprotect the final product. Final product is characterized by base composition, primer extension, and sequencing gel.

A candidate mixture of nucleic acids, or a library of nucleic acids, may also be produced by an enzymatic method using a solid phase. In one embodiment, this method comprises the same basic steps described above. In this case the goal is the synthesis of an antisense library and these libraries are produced with a 5' biotin modification. All remaining synthetic processes are as described above. Once the synthetic library is prepared, the nucleic acids may be used in a primer extension mix containing one or more modified nucleotides to produce the final candidate mixture in a classic primer extension method.

Aptamers may be synthesized by the same chemistry that is used for the synthesis of a library. However, instead of a mixture of nucleotides, one nucleotide is introduced at each step in the synthesis to control the final sequence generated by routine methods. Modified nucleotides may be introduced into the synthesis process at the desired positions in the sequence. Other functionalities may be introduced as desired using known chemical modifications of nucleotides.

As used herein, "candidate mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. Modified nucleotides, such as nucleotides with photoreactive groups or other modifications, can be incorporated into the candidate mixture. In addition, a SELEX process can be used to produce a candidate mixture, that is, a first SELEX process experiment can be used to produce a ligand-enriched mixture of nucleic acids that is used as the candidate mixture in a second SELEX process experiment. A candidate mixture can also comprise nucleic acids with one or more common structural motifs. As used herein, a candidate mixture is also sometimes referred to as a "pool" or a "library." For example, an "RNA pool" refers to a candidate mixture comprised of RNA.

In various embodiments, each nucleic acid in a candidate mixture may have fixed sequences on either side of a randomized region, to facilitate the amplification process. The nucleic acids in the candidate mixture of nucleic acids can each further comprise fixed regions or "tail" sequences at their 5' and 3' termini to prevent the formation of high molecular weight parasites during the amplification process.

As used herein, "nucleic acid," "oligonucleotide," and "polynucleotide" are used interchangeably to refer to a polymer of nucleotides of any length, and such nucleotides may include deoxyribonucleotides, ribonucleotides, and/or analogs or chemically modified deoxyribonucleotides or ribonucleotides. The terms "polynucleotide," "oligonucleotide," and "nucleic acid" include double- or single-stranded molecules as well as triple-helical molecules.

If present, chemical modifications of a nucleotide can include, singly or in any combination, 2'-position sugar modifications, 5-position pyrimidine modifications (e.g., 5-(N-benzylcarboxyamide)-2'-deoxyuridine, 5-(N-isobutylcarboxyamide)-2'-deoxyuridine, 5-(N-tryptaminocarboxyamide)-2'-deoxyuridine, 5-(N-[1-(3-trimethylammonium)propyl]carboxyamide)-2'-deoxyuridine chloride, 5-(N-naphthylmethylcarboxamide)-2'-deoxyuridine, or 5-(N-[1-(2,3-dihydroxypropyl)]carboxyamide)-2'-deoxyuridine), modifications at exocyclic amines, substitution of 4-thiouridine, substitution of 5-bromo- or 5-iodo-uracil, backbone modifications, methylations, unusual base-pairing combinations such as the isobases, isocytidine and isoguanidine, and the like.

Figure 14:
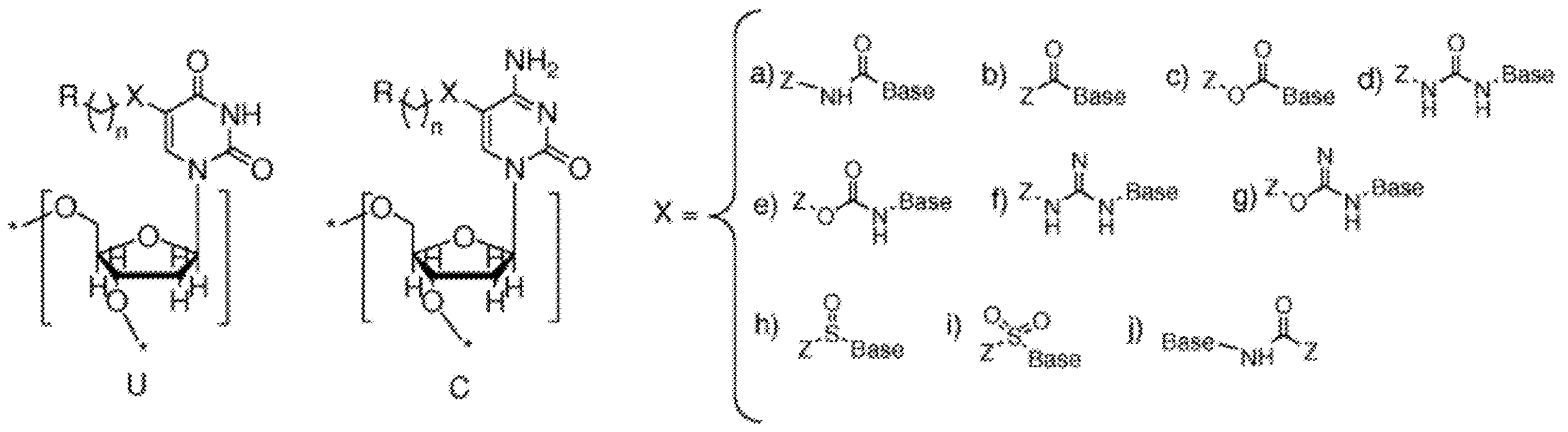
FIG. 14 describes the base modifications of nucleotides included in this disclosure. The R groups that may be used are described in addition to the linkers (X) that may be used between the nucleotide attachment point and the R group. The positions of attachment for the various "R" groups are also indicated on the respective R group.
Figure 14:
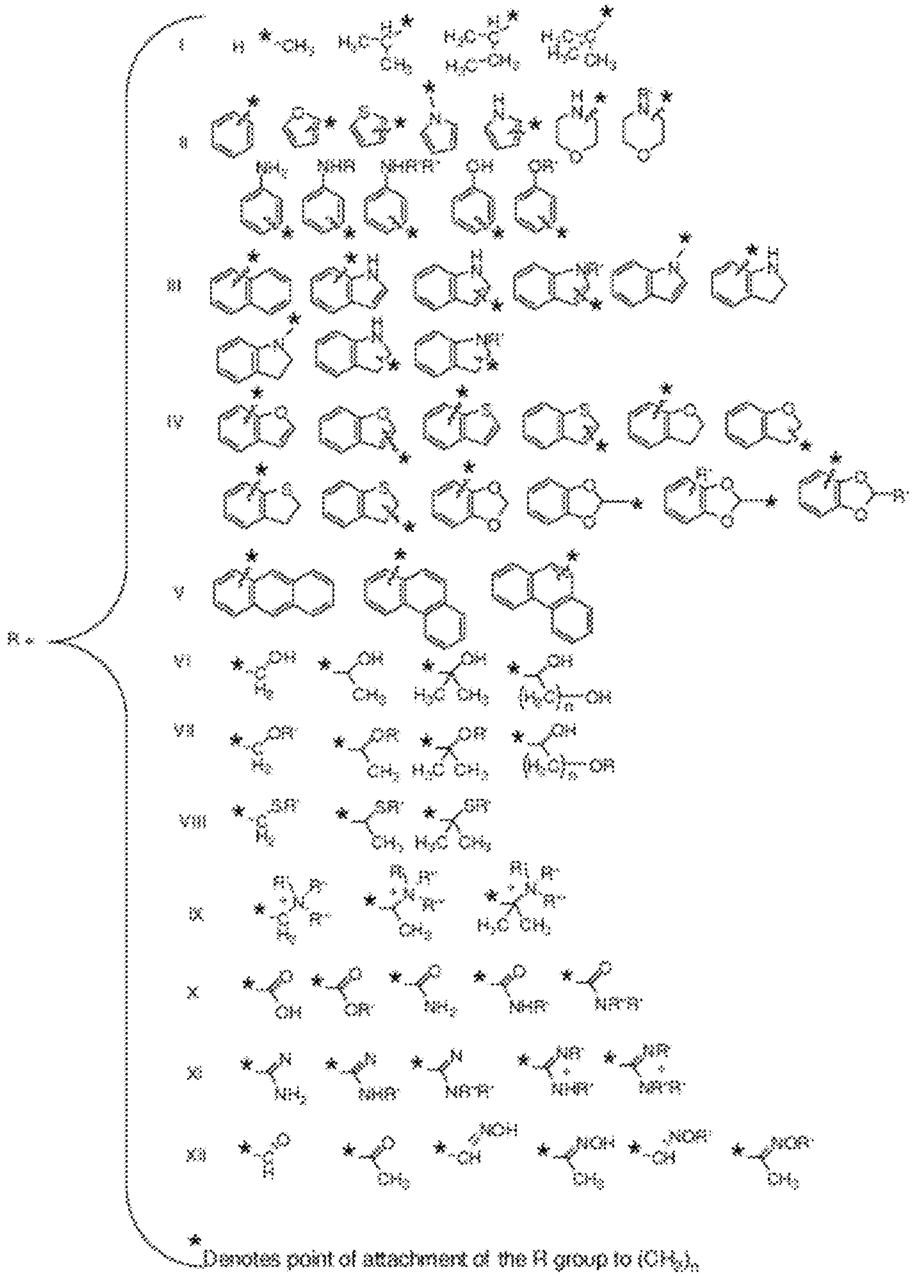

In one embodiment, the term "C-5 modified pyrimidine" refers to a pyrimidine with a modification at the C-5 position including, but not limited to those moieties illustrated in FIG. 14. Examples of a C-5 modified pyrimidine include those described in U.S. Pat. Nos. 5,719,273 and 5,945,527. Examples of a C-5 modification include substitution of deoxyuridine at the C-5 position with a substituent selected from: benzylcarboxyamide (alternatively benzylaminocarbonyl) (Bn), naphthylmethylcarboxyamide (alternatively naphthylmethylaminocarbonyl) (Nap), tryptaminocarboxyamide (alternatively tryptaminocarbonyl) (Trp), and isobutylcarboxyamide (alternatively isobutylaminocarbonyl) (iBu) as illustrated immediately below.

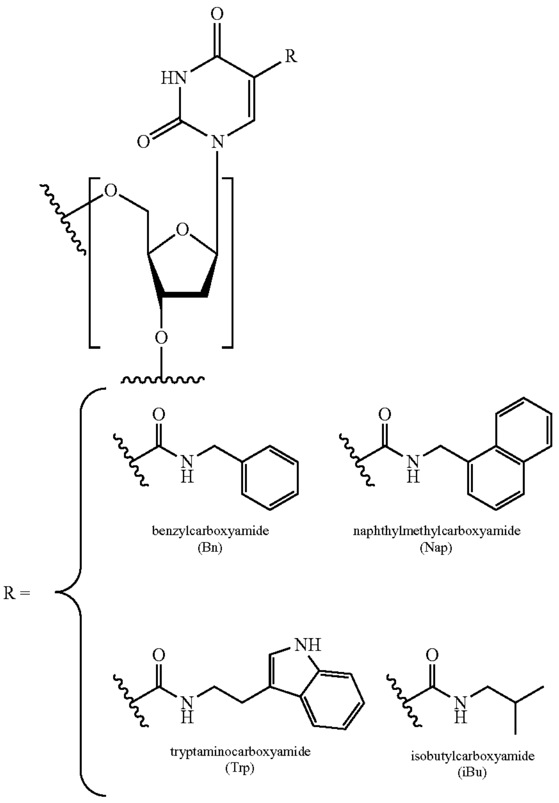

benzylcarboxyamide (Bn)

naphthylmethylcarboxyamide (Nap)

tryptaminocarboxyamide (Trp)

isobutylcarboxyamide (iBu)

As delineated above, representative C-5 modified pyrimidines include: 5-(N-benzylcarboxyamide)-2'-deoxyuridine (BndU), 5-(N-isobutylcarboxyamide)-2'-deoxyuridine (iBudU), 5-(N-tryptaminocarboxyamide)-2'-deoxyuridine (TrpdU) and 5-(N-naphthylmethylcarboxyamide)-2'-deoxyuridine (NapdU).

Modifications can also include 3' and 5' modifications, such as capping or pegylation. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present in a sugar may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, or organic capping group moieties of from about 1 to about 20 polyethylene glycol (PEG) polymers or other hydrophilic or hydrophobic biological or synthetic polymers. If present, a modification to the nucleotide structure may be imparted before or after assembly of a polymer. A sequence of nucleotides may be interrupted by non-nucleotide components. A polynucleotide may be further modified after polymerization, such as by conjugation with a labeling component.

Polynucleotides can also contain analogous forms of ribose or deoxyribose sugars that are generally known in the art, including 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. As noted above, one or more phosphodiester linkages may be replaced by alternative linking groups. These alternative linking groups include embodiments wherein phosphate is replaced by P(O)S ("thioate"), P(S)S ("dithioate"), $(O)NR_2$ ("amidate"), P(O)R, P(O)OR', CO or $CH_2$ ("formacetal"), in which each R or R' is independently H or substituted or unsubstituted alkyl (1-20 C) optionally containing an ether (—O—) linkage, aryl, alkenyl, cycloalky, cycloalkenyl or araldyl. Not all linkages in a polynucleotide need be identical. Substitution of analogous forms of sugars, purines, and pyrimidines can be advantageous in designing a final product, as can alternative backbone structures like a polyamide backbone, for example.

In one embodiment, the variable region of the aptamer includes nucleotides that include modified bases. Certain modified aptamers may be used in any of the described methods, devices, and kits. These modified nucleotides have been shown to produce novel aptamers that have very slow off-rates from their respective targets while maintaining high affinity to the target. In one embodiment, the C-5 position of the pyrimidine bases may be modified. Aptamers containing nucleotides with modified bases have a number of properties that are different than the properties of standard aptamers that include only naturally occurring nucleotides (i.e., unmodified nucleotides). In one embodiment, the method for modification of the nucleotides includes the use of an amide linkage. However, other suitable methods for modification may be used.

As used herein, "modified nucleic acid" refers to a nucleic acid sequence containing one or more modified nucleotides. In some embodiments it may be desirable that the modified nucleotides are compatible with the SELEX process.

"Polypeptide," "peptide," and "protein" are used interchangeably herein to refer to polymers of amino acids of any length. The polymer may be linear or branched, it may comprise modified amino acids, and/or it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can be single chains or associated chains. "Marker" is used to describe a target molecule, frequently a protein, that is a specific indicator or predictor of a specific disease or condition for which a diagnosis is desired.

As used herein, "photoreactive nucleotide" means any modified nucleotide that is capable of photocrosslinking with a target, such as a protein, upon irradiation with certain wavelengths of light. For example, photoaptamers produced by the photoSELEX process can include a photoreactive group selected from the following: 5-bromouracil (BrU), 5-iodouracil (IU), 5-bromovinyluracil, 5-iodovinyluracil, 5-azidouracil, 4-thiouracil, 5-bromocytosine, 5-iodocytosine, 5-bromovinylcytosine, 5-iodovinylcytosine, 5-azidocytosine, 8-azidoadenine, 8-bromoadenine, 8-iodoadenine, 8-azidoguanine, 8-bromoguanine, 8-iodoguanine, 8-azidohypoxanthine, 8-bromohypoxanthine, 8-iodohypoxanthine, 8-azidoxanthine, 8-bromoxanthine, 8-iodoxanthine, 5-bromodeoxyuridine, 8-bromo-2'-deoxyadenine, 5-iodo-2'-deoxyuracil, 5-iodo-2'-deoxycytosine, 5-[(4-azidophenacyl)thio]cytosine, 5-[(4-azidophenacyl)thio]uracil, 7-deaza-7-iodoadenine, 7-deaza-7-iodoguanine, 7-deaza-7-bromoadenine, and 7-deaza-7-bromoguanine. A "photoreactive pyrimidine" means any modified pyrimidine that is capable of photocrosslinking with a target upon irradiation of certain wavelengths. Exemplary photoreactive pyrimidines include 5-bromo-uracil (BrdU), 5-bromo-cytosine (BrdC), 5-iodo-uracil (IdU), and 5-iodo-cytosine (IdC). In various embodiments, the photoreactive functional group will absorb wavelengths of light that are not absorbed by the target or the non-modified portions of the oligonucleotide.

"SELEX" refers to a process that combines the selection of nucleic acids that interact with a target in a desirable manner (e.g., binding to a protein) with the amplification of those selected nucleic acids. Optional iterative cycling of the selection/amplification steps allows selection of one or a small number of nucleic acids that interact most strongly with the target from a pool that contains a very large number of nucleic acids. Cycling of the selection/amplification procedure is continued until a selected goal is achieved. The SELEX methodology is described in the SELEX Patents. In some embodiments of the SELEX process, aptamers that bind non-covalently to their targets are generated. In other embodiments of the SELEX process, aptamers that bind covalently to their targets are generated. In some embodiments the targets used in the SELEX process are fixed in the same manner that an analytical sample would be fixed during the use of the slow off-rate aptamer in the histological or cytological characterization of that analytical sample.

As used herein the term "amplification" or "amplifying" means any process or combination of process steps that increases the amount or number of copies of a molecule or class of molecules.

Figure 7:
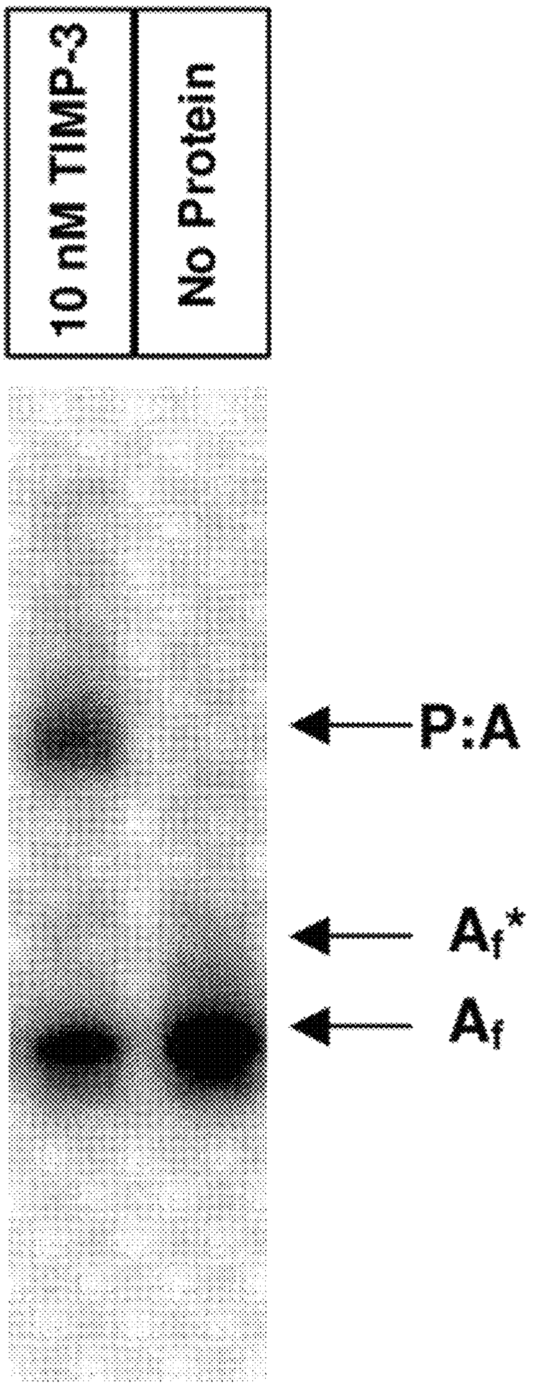
FIG. 7 illustrates a PAGE analysis of crosslink activity of TIMP-3 5'ANA/BndU enriched library using 5'-Fixed PhotoSELEX as described in Example 3. The gel illustrates the separation of free aptamer ($A_f$), intramolecular crosslinked aptamer ($A_f$*), and crosslinked protein:aptamer complexes (P:A).

"SELEX target" or "target molecule" or "target" refers herein to any compound upon which a nucleic acid can act in a desirable manner. A SELEX target molecule can be a protein, peptide, nucleic acid, carbohydrate, lipid, polysaccharide, glycoprotein, hormone, receptor, antigen, antibody, virus, pathogen, toxic substance, substrate, metabolite, transition state analog, cofactor, inhibitor, drug, dye, nutrient, growth factor, cell, tissue, any portion or fragment of any of the foregoing, etc., without limitation. Further the target may be modified in one or more fashion. For example, proteins may be modified by glycosylation, phosphorylation, acetylation, phospholipids, and so forth. The target may be modified to different levels. Slow off-rate aptamers could be produced to differentiate the type or level of modification. In one embodiment, a SELEX target does not include molecules that are known to bind nucleic acids, such as, for example, known nucleic acid binding proteins (e.g. transcription factors). Virtually any chemical or biological effector may be a suitable SELEX target. Molecules of any size can serve as SELEX targets. A target can also be modified in certain ways to enhance the likelihood or strength of an interaction between the target and the nucleic acid. A target can also include any minor variation of a particular compound or molecule, such as, in the case of a protein, for example, minor variations in amino acid sequence, disulfide bond formation, glycosylation, lipidation, acetylation, phosphorylation, or any other manipulation or modification, such as conjugation with a labeling component, which does not substantially alter the identity of the molecule. A "target molecule" or "target" is a set of copies of one type or species of molecule or multimolecular structure that is capable of binding to an aptamer. "Target molecules" or "targets" refer to more than one such set of molecules. Embodiments of the SELEX process in which the target is a peptide are described in U.S. Pat. No. 6,376,190, entitled "Modified SELEX Processes Without Purified Protein," incorporated herein by reference in its entirety. FIG. 7 lists over 500 targets for which aptamers have been produced including a variety of slow off-rate aptamers. The target may also be a "marker" or a molecule that is indicative of a specific disease state or condition and may be used in the diagnosis of that specific disease state or for selection of an appropriate therapeutic regimen or as an indication of potential therapeutic efficacy. Examples of such markers include prostate specific antigen for prostate cancer, CMBK for heart disease, CEA, CA125 for cancer, HPV16 and HPV18 for cervical cancer, etc. An example of a marker that is predictive of therapeutic efficacy is HER2.

"Tissue target" or "Tissue" refers to a certain subset of the SELEX targets described above. According to this definition, tissues are collections of macromolecules in a heterogeneous environment. As used herein, tissue refers to a single cell type, a collection of cell types, an aggregate of cells, or an aggregate of macromolecules. This differs from simpler SELEX targets which are typically isolated soluble molecules, such as proteins. In the one embodiment, tissues are insoluble macromolecules which are orders of magnitude larger than simpler SELEX targets. Tissues are complex targets made up of numerous macromolecules, each macromolecule having numerous epitopes that can be proteins, lipids, carbohydrates, etc., or combinations thereof. Tissues are generally a physical array of macromolecules that can be either fluid or rigid, both in terms of structure and composition. Extracellular matrix is an example of a more rigid tissue, both structurally and compositionally, while a membrane bilayer is more fluid in structure and composition. Tissues are generally not soluble and remain in solid phase, and thus partitioning can be accomplished relatively easily. Tissue includes, but is not limited to, an aggregate of cells usually of a particular kind together with their intercellular substance that form one of the structural materials commonly used to denote the general cellular fabric of a given organ, e.g., kidney tissue, brain tissue. The four general classes of tissues are epithelial tissue, connective tissue, nerve tissue, and muscle tissue.

Examples of tissues which fall within this definition include, but are not limited to, heterogeneous aggregates of macromolecules such as fibrin clots which are acellular; homgeneous or heterogeneous aggregates of cells; higher ordered structures containing cells which have a specific function, such as organs, tumors, lymph nodes, arteries, etc.; and individual cells. Tissues or cells can be in their natural environment, isolated, or in tissue culture. The tissue can be intact or modified. The modification can include numerous changes such as transformation, transfection, activation, and substructure isolation, e.g., cell membranes, cell nuclei, cell organelles, etc.

Sources of the tissue, cell or subcellular structures can be obtained from prokaryotes as well as eukaryotes. This includes human, animal, plant, bacterial, fungal and viral structures.

When a tissue SELEX process is used to identify target specific slow off-rate aptamers from a tissue/cell sample taken from a patient with a known disease, it may be of value to perform a secondary and optional counter selection. The counter selection provides the ability to discriminate between closely related but different tissue types. In this procedure the originally selected slow off-rate aptamers would be incubated with a tissue sample from a normal, or non-diseased donor. Any slow off-rate aptamers in this pre-screened candidate mixture that reacted with the normal tissue would be eliminated from subsequent selection. This additional step would insure that the final selected slow off-rate aptamer was highly specific. The normal tissue sample and the diseased tissue sample should be treated in the same manner (i.e., fixation).

As used herein, "competitor molecule" and "competitor" are used interchangeably to refer to any molecule that can form a non-specific complex with a non-target molecule. In this context, non-target molecules include free aptamers, where, for example, a competitor can be used to inhibit the aptamer from binding (re-binding), non-specifically, to another non-target molecule. A "competitor molecule" or "competitor" is a set of copies of one type or species of molecule. "Competitor molecules" or "competitors" refer to more than one such set of molecules. Competitor molecules include, but are not limited to oligonucleotides, polyanions (e.g., heparin, herring sperm DNA, salmon sperm DNA, tRNA, dextran sulfate, polydextran, abasic phosphodiester polymers, dNTPs, and pyrophosphate). In various embodiments, a combination of one or more competitor can be used.

As used herein, "non-specific complex" refers to a non-covalent association between two or more molecules other than an aptamer and its target molecule. A non-specific complex represents an interaction between classes of molecules. Non-specific complexes include complexes formed between an aptamer and a non-target molecule, a competitor and a non-target molecule, a competitor and a target molecule, and a target molecule and a non-target molecule.

As used herein, the term "slow off-rate enrichment process" refers to a process of altering the relative concentrations of certain components of a candidate mixture such that the relative concentration of aptamer affinity complexes having slow dissociation rates is increased relative to the concentration of aptamer affinity complexes having faster, less desirable dissociation rates. In one embodiment, the slow off-rate enrichment process is a solution-based slow off-rate enrichment process. In this embodiment, a solution-based slow off-rate enrichment process takes place in solution, such that neither the target nor the nucleic acids forming the aptamer affinity complexes in the mixture are immobilized on a solid support during the slow off-rate enrichment process. In various embodiments, the slow off-rate enrichment process can include one or more steps, including the addition of an incubation with a competitor molecule, dilution of the mixture, or a combination of these (e.g., dilution of the mixture in the presence of a competitor molecule). Because the effect of an slow off-rate enrichment process generally depends upon the differing dissociation rates of different aptamer affinity complexes (i.e., aptamer affinity complexes formed between the target molecule and different nucleic acids in the candidate mixture), the duration of the slow off-rate enrichment process is selected so as to retain a high proportion of aptamer affinity complexes having slow dissociation rates while substantially reducing the number of aptamer affinity complexes having fast dissociation rates. The slow off-rate enrichment process may be used in one or more cycles during the SELEX process. When dilution and the addition of a competitor are used in combination, they may be performed simultaneously or sequentially, in any order. The slow off-rate enrichment process can be used when the total target (protein) concentration in the mixture is low. In one embodiment, when the slow off-rate enrichment process includes dilution, the mixture can be diluted as much as is practical, keeping in mind that the nucleic acids are recovered for subsequent rounds in the SELEX process. In one embodiment, the slow off-rate enrichment process includes the use of a competitor as well as dilution, permitting the mixture to be diluted less than might be necessary without the use of a competitor.

In one embodiment, the slow off-rate enrichment process includes the addition of a competitor, and the competitor is a polyanion (e.g., heparin or dextran sulfate (dextran)). Heparin or dextran have been used in the identification of specific aptamers in prior SELEX selections. In such methods, however, heparin or dextran is present during the equilibration step in which the target and aptamer bind to form complexes. In such methods, as the concentration of heparin or dextran increases, the ratio of high affinity target/aptamer complexes to low affinity target/aptamer complexes increases. However, a high concentration of heparin or dextran can reduce the number of high affinity target/aptamer complexes at equilibrium due to competition for target binding between the nucleic acid and the competitor. By contrast, the presently described methods add the competitor after the target/aptamer complexes have been allowed to form and therefore does not affect the number of complexes formed. Addition of competitor after equilibrium binding has occurred between target and aptamer creates a non-equilibrium state that evolves in time to a new equilibrium with fewer target/aptamer complexes. Trapping target/aptamer complexes before the new equilibrium has been reached enriches the sample for slow off-rate aptamers since fast off-rate complexes will dissociate first.

In another embodiment, a polyanionic competitor (e.g., dextran sulfate or another polyanionic material) is used in the slow off-rate enrichment process to facilitate the identification of an aptamer that is refractory to the presence of the polyanion. In this context, "polyanionic refractory aptamer" is an aptamer that is capable of forming an aptamer/target complex that is less likely to dissociate in the solution that also contains the polyanionic refractory material than an aptamer/target complex that includes a non-polyanionic refractory aptamer. In this manner, polyanionic refractory aptamers can be used in the performance of analytical methods to detect the presence or amount or concentration of a target in a sample, where the detection method includes the use of the polyanionic material (e.g. dextran sulfate) to which the aptamer is refractory.

Thus, in one embodiment, a method for producing a polyanionic refractory aptamer is provided. In this embodiment, after contacting a candidate mixture of nucleic acids with the target, the target and the nucleic acids in the candidate mixture are allowed to come to equilibrium. A polyanionic competitor is introduced and allowed to incubate in the solution for a period of time sufficient to insure that most of the fast off-rate aptamers in the candidate mixture dissociate from the target molecule. Also, aptamers in the candidate mixture that may dissociate in the presence of the polyanionic competitor will be released from the target molecule. The mixture is partitioned to isolate the high affinity, slow off-rate aptamers that have remained in association with the target molecule and to remove any uncomplexed materials from the solution. The aptamer can then be released from the target molecule and isolated. The isolated aptamer can also be amplified and additional rounds of selection applied to increase the overall performance of the selected aptamers. This process may also be used with a minimal incubation time if the selection of slow off-rate aptamers is not needed for a specific application.

Thus, in one embodiment a modified SELEX process is provided for the identification or production of aptamers having slow (long) off-rates wherein the target and candidate mixture are contacted and incubated together for a period of time sufficient for equilibrium binding between the target and nucleic acids contained in the candidate mixture to occur. Following equilibrium binding an excess of competitor molecule, e.g., polyanion competitor, is added to the mixture and the mixture is incubated together with the excess of competitor molecule for a predetermined period of time. A significant proportion of aptamers having off-rates that are less than this predetermined incubation period will dissociate from the target during the predetermined incubation period. Re-association of these "fast" off-rate aptamers with the target is minimized because of the excess of competitor molecule which can non-specifically bind to the target and occupy aptamer binding sites on the target. A significant proportion of aptamers having longer off-rates will remain complexed to the target during the predetermined incubation period. At the end of the incubation period, partitioning nucleic acid-target complexes from the remainder of the mixture allows for the separation of a population of slow off-rate aptamers from those having fast off-rates. A dissociation step can be used to dissociate the slow off-rate aptamers from their target and allows for isolation, identification, sequencing, synthesis and amplification of slow off-rate aptamers (either of individual aptamers or of a group of slow off-rate aptamers) that have high affinity and specificity for the target molecule. As with conventional SELEX the aptamer sequences identified from one round of the modified SELEX process can be used in the synthesis of a new candidate mixture such that the steps of contacting, equilibrium binding, addition of competitor molecule, incubation with competitor molecule and partitioning of slow off-rate aptamers can be iterated/repeated as many times as desired.

The combination of allowing equilibrium binding of the candidate mixture with the target prior to addition of competitor, followed by the addition of an excess of competitor and incubation with the competitor for a predetermined period of time allows for the selection of a population of aptamers having off-rates that are much greater than those previously achieved.

Once a specific slow off-rate aptamer to the desired target is selected it may be produced synthetically or through cloning or any other method for producing the specific nucleic acid sequence.

Further specificity may be introduced by the process called "counter-SELEX" that effectively discards ligands that have ability to bind the target as well as closely related structural analogs of the target or targets within normal tissue or cell samples. In this embodiment, slow off-rate aptamers are selected for a specific tissue and then a counter selection is done against a related tissue which does not have certain characteristics for which the aptamer is desired. The counter selection can be done against a similar cell line or cell type, different cells, normal tissue, plasma or blood, a non-specific antibody or other available ligand. An example of this counter selection would be to first select using a tumor cell target (such as a malignant melanoma) and then counter select the resulting nucleic acids against a similar cell type which is not tumorogenic (such as normal human melanocytes). Aptamers that interact with both normal and neoplastic tissue will be removed by this negative selection and only those aptamers that specifically bind the tumor cells will be identified (or retained). The resulting aptamer would be specific for tumors.

This technique will provide the ability to identify aptamers that can discriminate between two closely related targets, i.e., between a cancerous cell and an untransformed cell of the same tissue type. The counter selection can also be done in vivo. Using this method one can not only generate aptamers to specific targets on complex tissue surfaces, but also be able to recognize the differences between normal and abnormal tissue of a particular type.

To generate a slow off-rate aptamer to a cell or tissue target, the cell or tissue sample is first mixed with a candidate mixture and equilibrium binding achieved. In order to achieve equilibrium binding, the candidate mixture is incubated with the target for at least about 5 minutes, or at least about 15 minutes, about 30 minutes, about 45 minutes, about 1 hour, about 2 hours, about 3 hours, about 4 hours, about 5 hours or about 6 hours. Once equilibrium binding is achieved the selection process may proceed.

In one embodiment, a competitor is used as an off-rate enhancement process. The predetermined incubation period of competitor molecule with the mixture of the candidate mixture and target may be selected as desired, taking account of factors such as the nature of the target and known off-rates (if any) of known aptamers for the target. Predetermined incubation periods may be chosen from: at least about 5 minutes, at least about 10 minutes, at least about 20 minutes, at least about 30 minutes, at least 45 about minutes, at least about 1 hour, at least about 2 hours, at least about 3 hours, at least about 4 hours, at least about 5 hours, at least about 6 hours.

In other embodiments, a dilution is used as an off-rate enhancement process and incubation of the diluted candidate mixture, target/aptamer complex may be undertaken for a predetermined period of time, which may be chosen from: at least about 5 minutes, at least about 10 minutes, at least about 20 minutes, at least about 30 minutes, at least about 45 minutes, at least about 1 hour, at least about 2 hours, at least about 3 hours, at least about 4 hours, at least about 5 hours, at least about 6 hours.

Embodiments of the present disclosure are concerned with the identification, production, synthesis and use of slow off-rate aptamers as well as uses of any specific aptamer. These are aptamers which have a dissociation half-life ($t_{1/2}$) from a non-covalent aptamer-target complex that is higher than that of aptamers normally obtained by conventional SELEX. For a mixture containing non-covalent complexes of aptamer and target, the $t_{1/2}$ represents the time taken for half of the aptamers to dissociate from the aptamer-target complexes. The $t_{1/2}$ of slow dissociation rate aptamers according to the present disclosure is chosen from one of: greater than or equal to about 15 minutes; between about 15 minutes and about 30 minutes; between about 30 minutes and about 240 minutes; between about 30 minutes to about 60 minutes; between about 60 minutes to about 90 minutes, between about 90 minutes to about 120 minutes; between about 120 minutes to about 150 minutes; between about 150 minutes to about 180 minutes; between about 180 minutes to about 210 minutes; between about 210 minutes to about 240 minutes.

A characterizing feature of an aptamer identified by a SELEX procedure is its high affinity for its target. An aptamer will have a dissociation constant ($K_d$) for its target that is chosen from one of: less than about 1 μM, less than about 100 nM, less than about 10 nM, less than about 1 nM, less than about 100 pM, less than about 10 pM, less than about 1 pM.

As used herein, the term "labeling agent," "label," or "detectable moiety," or "detectable element" or "detectable component" refers to one or more reagents that can be used to detect a target molecule/aptamer complex. A detectable moiety or label is capable of being detected directly or indirectly. In general, any reporter molecule that is detectable can be a label. Labels include, for example, (i) reporter molecules that can be detected directly by virtue of generating a signal, (ii) specific binding pair members that may be detected indirectly by subsequent binding to a cognate that contains a reporter molecule, (iii) mass tags detectable by mass spectrometry, (iv) oligonucleotide primers that can provide a template for amplification or ligation, and (v) a specific polynucleotide sequence or recognition sequence that can act as a ligand, such as, for example, a repressor protein, wherein in the latter two instances the oligonucleotide primer or repressor protein will have, or be capable of having, a reporter molecule, and so forth. The reporter molecule can be a catalyst, such as an enzyme, a polynucleotide coding for a catalyst, promoter, dye, fluorescent molecule, quantum dot, chemiluminescent molecule, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, a mass tag that alters the weight of the molecule to which it is conjugated for mass spectrometry purposes, and the like. The label can be selected from electromagnetic or electrochemical materials. In one embodiment, the detectable label is a fluorescent dye. Other labels and labeling schemes will be evident to one skilled in the art based on the disclosure herein.

A detectable moiety (element or component) can include any of the reporter molecules listed above and any other chemical or component that may be used in any manner to generate a detectable signal. The detectable moiety, or signal generating label, may be detected via a fluorescent signal, a chemiluminescent signal, or any other detectable signal that is dependent upon the identity of the moiety. In the case where the detectable moiety is an enzyme (for example, alkaline phosphatase), the signal may be generated in the presence of the enzyme substrate and any additional factors necessary for enzyme activity. In the case where the detectable moiety is an enzyme substrate, the signal may be generated in the presence of the enzyme and any additional factors necessary for enzyme activity. Suitable reagent configurations for attaching the detectable moiety to a target molecule include covalent attachment of the detectable moiety to the target molecule, non-covalent association of the detectable moiety with another labeling agent component that is covalently attached to the target molecule, and covalent attachment of the detectable moiety to a labeling agent component that is non-covalently associated with the target molecule.

Detectable moieties may be incorporated into an aptamer during synthesis by using labeled dNTPs, dyes that have been generated as phosphoramidites, or other chemistries that can be employed during oligonucleotide synthesis, or may be incorporated by modification of the final aptamer product after synthesis. Each aptamer may include multiple detectable moieties to enhance signal generation. When multiple targets from the same sample, for example a histological tissue section, are to be detected then each target specific aptamer may be produced with an unique detectable moiety for simultaneous analysis of multiple targets.

In some embodiments, the labeled aptamers make possible rapid and specific staining of tissue or cell samples. For example, in some instances specific target staining of tissue sections or cell preparations may be achieved in ≤about 15 minutes, ≤about 10 minutes, ≤about 5 minutes, and ≤about 1 minute. Rapid staining is particularly advantageous in the diagnosis of abnormal or diseased tissue in an intraoperative setting.

As used herein, "partitioning" means any process whereby one or more components of a mixture are separated from other components of the mixture. For example, aptamers bound to target molecules can be partitioned from other nucleic acids that are not bound to target molecules and from non-target molecules. More broadly stated, partitioning allows for the separation of all the nucleic acids in a candidate mixture into at least two pools based on their relative affinity and/or dissociation rate to the target molecule. Partitioning can be accomplished by various methods known in the art, including filtration, affinity chromatography, liquid-liquid partitioning, HPLC, etc. For example, nucleic acid-protein pairs can be bound to nitrocellulose filters while unbound nucleic acids are not. Columns that specifically retain nucleic acid-target complexes can also be used for partitioning. For example, oligonucleotides able to associate with a target molecule bound on a column allow the use of column chromatography for separating and isolating the highest affinity aptamers. Beads upon which target molecules are conjugated can also be used to partition aptamers in a mixture. If the beads are paramagnetic, the partitioning can be achieved through application of a magnetic field. Surface plasmon resonance technology can be used to partition nucleic acids in a mixture by immobilizing a target on a sensor chip and flowing the mixture over the chip, wherein those nucleic acids having affinity for the target can be bound to the target, and the remaining nucleic acids can be washed away. Liquid-liquid partitioning can be used as well as filtration gel retardation and density gradient centrifugation. Affinity tags on the target molecules can also be used to separate nucleic acid molecules bound to the tagged target from aptamers that are free in solution. For example, biotinylated target molecules, along with aptamers bound to them, can be sequestered from the solution of unbound nucleic acid sequences using streptavidin paramagnetic beads. Affinity tags can also be incorporated into the aptamer during preparation. When Tissue SELEX is used to produce aptamers specific to one or more targets in a biological tissue (tissue section or cell preparation), the non-specific nucleic acids in a candidate mixture may be separated from the target specific aptamers by washing the tissue sample with one or more series of buffered reagents.

As used herein, "photoSELEX" is an acronym for Photochemical Systematic Evolution of Ligands by Exponential enrichment and refers to embodiments of the SELEX process in which photocrosslinking aptamers are generated. In one embodiment of the photoSELEX process, a photoreactive nucleotide activated by absorption of light is incorporated in place of a native base in either RNA- or in ssDNA-randomized oligonucleotide libraries, the nucleic acid target molecule mixture is irradiated causing some nucleic acids incorporated in nucleic acid-target molecule complexes to crosslink to the target molecule via the photoreactive functional groups, and the selection step is a selection for photocrosslinking activity. The photoSELEX process is described in great detail in the PhotoSELEX Patents.

As used herein, "photoaptamer" and "photoreactive aptamer" are used interchangeably to refer to an aptamer that contains one or more photoreactive functional groups that can covalently bind to or "crosslink" with a target molecule. For example, a naturally occurring nucleic acid residue may be modified to include a chemical functional group that confers photoreactivity upon the nucleic acid residue upon exposure to a radiation source of an appropriate wavelength. In some embodiments, a photoreactive aptamer is identified initially. In other embodiments, an aptamer is first identified and is subsequently modified to incorporate one or more photoreactive functional groups, thereby generating a photoaptamer. In these embodiments, one or more photoreactive nucleic acid residues can be incorporated into an aptamer either by substituting a photoreactive nucleic acid residue in the place of one or more other nucleotides, such as one or more of the thymidine and/or cytidine nucleotides in the aptamer, for example, or by modifying one or more nucleic acid residues to include a photoreactive functional group.

In yet other embodiments, certain nucleotides may be modified to produce slow off-rate aptamers that bind and form a covalent crosslink to their target in the affinity complex. This method encompasses slow off-rate aptamers that bind and then may be linked to their respective targets. In various embodiments, the slow off-rate aptamers may contain photoreactive groups that are capable of photocrosslinking to the target molecule upon irradiation with light. In other embodiments, the slow off-rate aptamers are capable of bond formation with the target in the absence of irradiation. A tight ionic interaction between the slow off-rate aptamer and target may also occur upon irradiation. Other mechanisms for chemical crosslinking may also be used. The crosslinking of slow off-rate aptamer to its specific target maybe initiated by a crosslinking activator, such as irradiation, or a specific chemical agent. In one embodiment, photocrosslinking occurs due to exposure to electromagnetic radiation. Electromagnetic radiation includes ultraviolet light, visible light, X-rays, and gamma rays. A crosslinking step may be added to the analysis of a tissue or cell sample at any point in the assay procedure.

A photoreactive group can be any chemical structure that contains a photochromophore and that is capable of photocrosslinking with a target. Although referred to herein as a photoreactive groups, in some cases, as described below, irradiation is not necessary for covalent binding to occur between the slow off-rate aptamer and the target. In some embodiments, the photoreactive group will absorb light of a wavelength that is not absorbed by the target or the non-modified portions of the oligonucleotide. Photoreactive groups include 5-halo-uridines, 5-halo-cytosines, 7-halo-adenosines, 2-nitro-5-azidobenzoyls, diazirines, aryl azides, fluorinated aryl azides, benzophenones, amino-benzophenones, psoralens, anthraquinones, etc.

Exemplary photoreactive functional groups that may be incorporated by a photoaptamer include 5-bromouracil, 5-iodouracil, 5-bromovinyluracil, 5-iodovinyluracil, 5-azidouracil, 4-thiouracil, 5-thiouracil, 4-thiocytosine, 5-bromocytosine, 5-iodocytosine, 5-bromovinylcytosine, 5-iodovinylcytosine, 5-azidocytosine, 8-azidoadenine, 8-bromoadenine, 8-iodoadenine, 8-aziodoguanine, 8-bromoguanine, 8-iodoguanine, 8-azidohypoxanthine, 8-bromohypoxanthine, 8-iodohypoxanthine, 8-azidoxanthine, 8-bromoxanthine, 8-iodoxanthine, 5-[(4-azidophenacyl)thio]cytosine, 5-[(4-azidophenacyl)thio]uracil, 7-deaza-7-iodoadenine, 7-deaza-7-iodoguanine, 7-deaza-7-bromoadenine, and 7-deaza-7-bromoguanine.

In addition to these exemplary nucleoside-based photoreactive functional groups, other photoreactive functional groups that can be added to a terminal end of an aptamer using an appropriate linker molecule can also be used. Such photoreactive functional groups include benzophenone, anthraquinone, 4-azido-2-nitro-aniline, psoralen, derivatives of any of these, and the like.

A photoreactive functional group incorporated by a photoaptamer may be activated by any suitable method. In one embodiment, a photoaptamer containing a photoreactive functional group can be crosslinked to its target by exposing the photoaptamer and its bound target molecule to a source of electromagnetic radiation. Suitable types of electromagnetic radiation include ultraviolet light, visible light, X-rays, and gamma rays. Suitable radiation sources include sources that utilize either monochromatic light or filtered polychromatic light.

As used herein, the term "the affinity SELEX process" refers to embodiments of the SELEX process in which non-photocrosslinking aptamers to targets are generated. In some embodiments of the affinity SELEX process, the target is immobilized on a solid support either before or after the target is contacted with the candidate mixture of nucleic acids. The association of the target with the solid support allows nucleic acids in the candidate mixture that have bound and in the case where a slow off-rate enrichment process is used, stay bound to the target to be partitioned from the remainder of the candidate mixture. The term "bead affinity SELEX process" refers to particular embodiments of the affinity SELEX process where the target is immobilized on a bead, for example, before contact with the candidate mixture of nucleic acids. In some embodiments, the beads are paramagnetic beads. The term "filter affinity SELEX process" refers to embodiments where nucleic acid target complexes are partitioned from candidate mixture by virtue of their association with a filter, such as a nitrocellulose filter. This includes embodiments where the target and nucleic acids are initially contacted in solution, and contacted with the filter, and also includes embodiments where nucleic acids are contacted with target that is pre-immobilized on the filter. The term "plate affinity SELEX process" refers to embodiments where the target is immobilized on the surface of a plate, such as, for example, a multi-well microtiter plate. In some embodiments, the plate is comprised of polystyrene. In some embodiments, the target is attached to the plate in the plate affinity SELEX process through hydrophobic interactions.

The present disclosure describes improved SELEX methods for generating and using aptamers that are capable of binding to one or more targets in a cell or tissue sample. More specifically, the present disclosure describes methods for identifying aptamers and/or photoaptamers having slower rates of dissociation from their respective targets than aptamers obtained with previous SELEX methods. The disclosure further describes aptamers and/or photoaptamers obtained using the methods described herein and methods of using the same. Optionally it may be desirable to confirm the identity of the specific target selected by the tissue selection process by traditional biochemical isolation, purification, and characterization. These methods could include mass spectroscopy, 2-D electrophoresis, etc.

In one embodiment, a method is provided for identifying an aptamer having a slow rate of dissociation from its target, the method comprising (a) preparing a candidate mixture of nucleic acid sequences; (b) contacting the candidate mixture with a tissue or cell sample wherein nucleic acids with the highest relative affinities to the target of interest in said tissue or cell sample preferentially bind the target, forming nucleic acid-target complexes; (c) applying a slow off-rate enrichment process to allow the dissociation of nucleic acid-target complexes with relatively fast dissociation rates; (d) partitioning the remaining nucleic acid-target complexes from both free nucleic acids and non-target molecules in the candidate mixture; and (e) identifying an aptamer to the target of interest. The process may further include the iterative step of amplifying the nucleic acids that bind to the target to yield a mixture of nucleic acids enriched in sequences that are able to bind to the target yet produce nucleic acid-target complexes having slow dissociation rates. As defined above, the slow off-rate enrichment process can be selected from (a) diluting the candidate mixture containing the nucleic acid-target molecule complexes; (b) adding at least one competitor to the candidate mixture containing the nucleic acid-target molecule complexes, and diluting the candidate mixture containing the nucleic acid-target molecule complexes; (c) and adding at least one competitor to the candidate mixture containing the nucleic acid-target molecule complexes.

Optionally the tissue or cell sample is fixed prior to their use in the slow off-rate aptamer selection process. Chemical fixatives can alter target epitopes in a predictable and reproducible way that allows for selection of aptamers that are specific for the fixed form of the epitope.

In one embodiment, a method is provided for producing an aptamer having a slow rate of dissociation from its target, the method comprising (a) preparing a candidate mixture of nucleic acid sequences; (b) contacting the candidate mixture with a tissue or cell sample wherein nucleic acids with the highest relative affinities to the target preferentially bind the target, forming nucleic acid-target complexes; (c) applying a slow off-rate enrichment process to allow the dissociation of nucleic acid-target complexes with relatively fast dissociation rates; (d) partitioning the remaining nucleic acid-target complexes from both free nucleic acids and non-target molecules in the candidate mixture; and (e) producing an aptamer to the target. The process may further include the iterative step of amplifying the nucleic acids that bind to the target to yield a mixture of nucleic acids enriched in sequences that are able to bind to the target yet produce nucleic acid-target complexes having slow dissociation rates. As defined above, the slow off-rate enrichment process can be selected from (a) diluting the candidate mixture containing the nucleic acid-target complexes; (b) adding at least one competitor to the candidate mixture containing the nucleic acid-target complexes, and diluting the candidate mixture containing the nucleic acid-target complexes; (c) and adding at least one competitor to the candidate mixture containing the nucleic acid-target complexes.

In one embodiment, a method is provided for identifying an aptamer having a slow rate of dissociation from its target, the method comprising: (a) preparing a candidate mixture of nucleic acids; (b) contacting the candidate mixture with a tissue or cell sample, wherein nucleic acids having an increased affinity to the target relative to other nucleic acids in the candidate mixture bind the target, forming nucleic acid-target complexes; (c) incubating the candidate mixture and target together for a period of time sufficient to achieve equilibrium binding; (d) applying a slow off-rate enrichment process to allow the dissociation of nucleic acid-target complexes with relatively fast dissociation rates to the mixture of (c); (e) incubating the mixture of the candidate mixture, the nucleic acid-target complexes and the competitor molecule from (d) for a predetermined period of time; (f) partitioning the nucleic acid-target complexes from the candidate mixture; (g) dissociating the nucleic acid-target complexes to generate free nucleic acids; (h) amplifying the free nucleic acids to yield a mixture of nucleic acids enriched in nucleic acid sequences that are capable of binding to the target with increased affinity, whereby an aptamer to the target may be identified. As defined above, the slow off-rate enrichment process can be selected from (a) diluting the candidate mixture containing the nucleic acid-target complexes; (b) adding at least one competitor to the candidate mixture containing the nucleic acid-target complexes, and diluting the candidate mixture containing the nucleic acid-target complexes; (c) and adding at least one competitor to the candidate mixture containing the nucleic acid-target complexes.

In another embodiment, a method is provided for producing an aptamer having a slow rate of dissociation from its target, the method comprising: (a) preparing a candidate mixture of nucleic acids; (b) contacting the candidate mixture with a tissue or cell sample, wherein nucleic acids having an increased affinity to the target relative to other nucleic acids in the candidate mixture bind the target, forming nucleic acid-target complexes; (c) incubating the candidate mixture and target together for a period of time sufficient to achieve equilibrium binding; (d) applying a slow off-rate enrichment process to allow the dissociation of nucleic acid-target complexes with relatively fast dissociation rates to the mixture of (c); (e) incubating the mixture of the candidate mixture, the nucleic acid-target complexes and the competitor molecule from (d) for a predetermined period of time; (f) partitioning the nucleic acid-target complexes from the candidate mixture; (g) dissociating the nucleic acid-target complexes to generate free nucleic acids; (h) amplifying the free nucleic acids to yield a mixture of nucleic acids enriched in nucleic acid sequences that are capable of binding to the target with increased affinity, whereby an aptamer to the target may be produced. As defined above, the slow off-rate enrichment process can be selected from (a) diluting the candidate mixture containing the nucleic acid-target complexes; (b) adding at least one competitor to the candidate mixture containing the nucleic acid-target complexes, and diluting the candidate mixture containing the nucleic acid-target complexes; (c) and adding at least one competitor to the candidate mixture containing the nucleic acid-target complexes.

In another embodiment, a method is provided of identifying an aptamer having a slow rate of dissociation from its target, the method comprising: (a) preparing a candidate mixture of nucleic acids, wherein the candidate mixture comprises modified nucleic acids in which one, several or all pyrimidines in at least one, or each, nucleic acid of the candidate mixture is chemically modified at the 5-position; (b) contacting the candidate mixture with a cell or tissue sample, wherein nucleic acids having an increased affinity to the target relative to other nucleic acids in the candidate mixture bind the target, forming nucleic acid-target complexes; (c) partitioning the increased affinity nucleic acids from the remainder of the candidate mixture; and (d) amplifying the increased affinity nucleic acids to yield a mixture of nucleic acids enriched in nucleic acid sequences that are capable of binding to the target with increased affinity, whereby an aptamer to the target may be identified.

In another embodiment, a method is provided for producing an aptamer having a slow rate of dissociation from its target, said method comprising preparing or synthesizing an aptamer that includes a nucleic acid sequence identified by the following process: (a) preparing a candidate mixture of nucleic acids, wherein the candidate mixture comprises modified nucleic acids in which one, several or all pyrimidines in at least one, or each, nucleic acid of the candidate mixture is chemically modified at the 5-position; (b) contacting the candidate mixture with a tissue or cell sample, wherein nucleic acids having an increased affinity to the target relative to other nucleic acids in the candidate mixture bind the target, forming nucleic acid-target complexes; (c) partitioning the increased affinity nucleic acids from the remainder of the candidate mixture; and (d) amplifying the increased affinity nucleic acids to yield a mixture of nucleic acids enriched in nucleic acid sequences that are capable of binding to the target with increased affinity, whereby an aptamer to the target is identified.

In another embodiment, a non-covalent complex of an aptamer and its target is provided, wherein the dissociation half-life ($t_{1/2}$) of the aptamer from the target is chosen from one of: greater than or equal to about 15 minutes; between about 15 minutes and about 30 minutes; between about 30 minutes and about 240 minutes; about 30 minutes to about 60 minutes; about 60 minutes to about 90 minutes; about 90 minutes to about 120 minutes; about 120 minutes to about 150 minutes; about 150 minutes to about 180 minutes; about 180 minutes to about 210 minutes; about 210 minutes to about 240 minutes.

In another embodiment, a non-covalent complex of an aptamer and a target is provided, wherein the aptamer has a $K_d$ for the target of about 100 nM or less, wherein the dissociation half-life ($t_{1/2}$) of the aptamer from the target is greater than or equal to about 15 minutes, and wherein one, several or all pyrimidines in the nucleic acid sequence of the aptamer are modified at the 5-position of the base. The modifications may be selected from the group of compounds shown in FIG. 14, these modifications are referred to as "base modified nucleotides". Aptamers may be designed with any combination of the base modified pyrimidines desired.

Improved methods for performing SELEX with modified nucleotides, including nucleotides which contain photoactive groups or nucleotides which contain placeholders for photoactive groups are disclosed in U.S. application Ser. No. 12/175,388, entitled "Improved SELEX and PHOTOSELEX" filed Jul. 17, 2008, which is incorporated herein by reference in its entirety. In another embodiment, the candidate mixture of nucleic acid molecules includes nucleic acids containing modified nucleotide bases that may aid in the formation of modified nucleic acid-target complexes with relatively slow dissociation rates.

The various methods and steps described herein can be used to generate an aptamer capable of either (1) binding to a target molecule or (2) binding to a target molecule and subsequently forming a covalent linkage with the target molecule upon irradiation.

Aptamers identified according to the methods described herein are useful in a range of diagnostic and therapeutic methods. Slow off-rate aptamers will bind to the target for a longer duration. This is useful in diagnostic methods where the binding of an aptamer to the target may be used to detect the presence, absence, amount or quantity of the target molecule and a prolonged interaction of the aptamer and target facilitates such detection. A similar advantage may be afforded where slow off-rate aptamers are used in imaging methods, in vitro or in vivo. A prolonged interaction of aptamer and target also provides for improved therapeutic methods of treatment where the prolonged interaction may allow for an improved therapeutic effect, e.g. owing to the longer activation or inhibition of the target molecule or downstream signaling cascade. These slow off-rate aptamers and aptamers with high affinity may be used in cytological and histological molecular detection and identification methods.

Accordingly, in various embodiments, slow off-rate aptamers obtained, identified or produced by the described methods can be used in a variety of methods of medical treatment or methods of diagnosis (in vitro or in vivo). In one embodiment, slow off-rate aptamers can be used in a method of treatment of disease. In one embodiment, slow off-rate aptamers can be used in a method for diagnosis of disease in vivo. In another embodiment, slow off-rate aptamers can be used in vitro for the diagnosis of disease. In another embodiment, a slow off-rate aptamer can be used in the manufacture of a therapeutic (e.g. pharmaceutical composition) or the manufacture of a diagnostic agent for use in a method of treatment or diagnosis of disease. Diagnostic or therapeutic applications of slow off-rate aptamers may involve a diagnostic or therapeutic outcome that depends on the specific and/or high affinity binding of the slow off-rate aptamer to its target. Slow off-rate aptamers may also be used in target validation and high throughput screening assays in the drug development process.

In one embodiment, slow off-rate aptamers are suitable reagents for molecular imaging in vivo. In this embodiment, a slow off-rate aptamer may be used in vivo to detect the presence of a pathology, disease process, or other condition in the body of an individual (e.g., a human or an animal), where the binding of the aptamer to its target indicates the presence of the disease process or other condition. For example, an aptamer to the VEGF receptor may be used in vivo to detect the presence of cancer in a particular area (e.g., a tissue, an organ, etc.) of the body of an individual, as the VEGF receptor is abundantly expressed within tumors and their neovasculature, or an aptamer to the EGF receptor may be used in vivo to detect the presence of cancer in a particular area (e.g., a tissue, an organ, etc.) of the body of an individual, as the EGF receptor is often expressed at high levels on tumor cells. That is, the molecular target will be the extracellular domain (ECD) of an induced receptor, as such targets are located outside of the cells and are accessible through the vasculature. Additionally, the ECDs tend to be localized at the site of pathology, even though some small fraction of the specific ECD may be shed through biological processes, including cell death.

The obvious candidates for molecular imaging, high affinity monoclonal antibodies, have not become the reagent of choice for this application. Molecular imaging reagents have precise requirements. They must have high binding activity for their intended target, and low binding activity for other targets in a human or animal. Slow off-rate aptamers have unique advantages that render them desirable for use in molecular imaging in vivo. On the one hand, they are selected to have slow dissociation rate constants, thus allowing residence in vivo on the intended target for a substantial length of time (at least about 15 minutes). On the other hand, slow off-rate aptamers are expected to have very fast clearance from the vasculature. Slow dissociation rate constants and fast clearance from the vasculature are two desired properties for molecular imaging in vivo. From a kinetic prospective, good in vivo molecular imaging reagents must stay localized at the site of the pathology while the free reagent concentration in the surrounding vasculature becomes low. This is a signal-to-noise constraint. Suitable signal-to-noise ratios may be obtained by accumulation of signal at the site of pathology in excess of the signal in the vasculature, or may be obtained by retention of a signal at the site of the pathology while the vasculature concentration is diminished.

Aptamers that do not have slow off-rate properties, of about the same molecular weight and net charge as slow off-rate aptamers, have been studied in animals and humans for more than a decade. Generally, it has been found that these aptamers clear from the vasculature quickly, usually by entering the kidney and/or the liver and then being further metabolized for excretion. Such aptamers show so-called "first pass" clearance unless high molecular weight adducts (such as, for example, PEG) are linked to the aptamers. Experiments have been done with an aptamer whose target is tenascin C, an extracellular protein (not an ECD) found at high concentrations in some tumors. In those experiments, the tenascin C-specific aptamer cleared quickly and was able to be retained at the site of the tumor because the extracellular local concentration of tenascin C is very high. Slow off-rate aptamers, by contrast, will maintain the fast clearance rate of aptamers but offer a kinetic advantage due to their slow dissociation rates, rendering them suitable for use with targets whose presence at the site of interest (e.g., the site of pathology) may be somewhat sparse (ECDs on tumors, for example).

Alternative reagents for molecular imaging do not share the two slow off-rate aptamer properties (i.e., slow dissociation rate and fast clearance from the body). Monoclonal antibodies often have high affinity and specificity, and may have slow dissociation rate constants; however, monoclonal antibodies have very slow clearance rates from the vasculature. Short peptides, identified through, for example, phage display, may have fast clearance but poor affinity and specificity and fast dissociation rates from their intended targets. Affibodies, a particular peptide version of an antibody mimetic, may have reasonable affinity and specificity and may have faster clearance than monoclonal antibodies, yet in order to achieve slow dissociation rates from their targets, affibodies are often made into dimers and higher order multimers, slowing their clearance at the same time that their dissociation rates are enhanced.

Slow off-rate aptamers may be used for molecular imaging in vivo with one or more low molecular weight adducts to both protect the slow off-rate aptamer from nucleases in the body and detect the intended target once bound by the slow off-rate aptamer. For example, slow off-rate aptamers may be attacked by nucleases in the blood, typically exonucleases (for DNA) that are easily blocked by using exonuclease refractive adducts at the 5' and 3' terminal positions of the slow off-rate aptamer, or endonucleases (for RNA) that are easily blocked by incorporating endonuclease refractive pyrimidines (such as, for example, 2' fluoro nucleotides) in the slow off-rate aptamer. Detection of the slow off-rate aptamer-target complex may be achieved by attaching a detection moiety to the slow off-rate aptamer. In some embodiments, the detection moiety for these purposes may include cages for radioactive molecules (e.g., technetium 99), clusters of iron for magnetic resonance detection, isotopes of fluorine for PET imaging, and the like. The modifications made to the slow off-rate aptamer to protect the integrity of the slow off-rate aptamer in the body and enable detection of the intended target should be designed such that they do not interfere with the slow off-rate aptamer's interaction with its target and do not cause the slow off-rate aptamer to clear too slowly from the vasculature.

Diagnostic or assay devices, e.g. columns, test strips or biochips, having one or more slow off-rate aptamers adhered to a solid surface of the device are also provided. The aptamer(s) may be positioned so as to be capable of binding target molecules that are contacted with the solid surface to form aptamer-target complexes that remain adhered to the surface of the device, thereby capturing the target and enabling detection and optionally quantitation of the target. An array of slow off-rate aptamers (which may be the same or different) may be provided on such a device.

In another embodiment, complexes including a slow off-rate aptamer and a target molecule are provided. In other embodiments, a class of aptamers characterized by having high affinity for their corresponding target molecules and slow dissociation rates ($t_{1/2}$) from a non-covalent complex of the aptamer and target is provided.

The basic SELEX process generally begins with the preparation of a candidate mixture of nucleic acids of differing sequence. The candidate mixture generally includes nucleic acid sequences that include two fixed regions (i.e., each of the members of the candidate mixture contains the same sequences in the same location) and a variable region. Typically, the fixed sequence regions are selected such that they assist in the amplification steps described below, or enhance the potential of a given structural arrangement of the nucleic acids in the candidate mixture. The variable region typically provides the target binding region of each nucleic acid in the candidate mixture, and this variable region can be completely randomized (i.e., the probability of finding a base at any position being one in four) or only partially randomized (e.g., the probability of finding a base at any location can be selected at any level between 0 and 100 percent). The prepared candidate mixture is contacted with the selected target under conditions that are favorable for binding to occur between the target and members of the candidate mixture. Under these conditions, the interaction between the target and the nucleic acids of the candidate mixture generally forms nucleic acid-target pairs that have the strongest relative affinity between members of the pair. The nucleic acids with the highest affinity for the target are partitioned from those nucleic acids with lesser affinity to the target. The partitioning process is conducted in a manner that retains the maximum number of high affinity candidates. Those nucleic acids selected during partitioning as having a relatively high affinity to the target are amplified to create a new candidate mixture that is enriched in nucleic acids having a relatively high affinity for the target. By repeating the partitioning and amplifying steps above, the newly formed candidate mixture contains fewer and fewer unique sequences, and the average degree of affinity of the nucleic acid mixture to the target will generally increase. Taken to its extreme, the SELEX process will yield a candidate mixture containing one or a very small number of unique nucleic acids representing those nucleic acids from the original candidate mixture that have the highest affinity to the target molecule. However, this basic SELEX process does not select for aptamers that have slow off-rates from their targets.

The SELEX Patents and the PhotoSELEX Patents describe and elaborate on this process in great detail. These patents include descriptions of the various targets that can be used in the process; methods for the preparation of the initial candidate mixture; methods for partitioning nucleic acids within a candidate mixture; and methods for amplifying partitioned nucleic acids to generate enriched candidate mixtures. The SELEX Patents also describe aptamer solutions obtained to a number of different types of target molecules, including protein targets wherein the protein is and is not a nucleic acid binding protein. With reference to FIG. 2 the modified SELEX process disclosed herein includes the introduction of a slow off-rate enrichment process following equilibration of the candidate mixture of nucleic acids with the target or targets and a partitioning step prior to subsequent steps in the SELEX process. Introduction of a slow off-rate enrichment process to the basic SELEX process provides a means for enrichment of aptamer affinity complexes with slow dissociation rates from a set of nucleic acid-target complexes that includes a variety of dissociation rates. Thus, the modified SELEX process provides a method for identifying aptamers that bind target molecules and, once bound, have relatively slow rates of dissociation (also referred to herein as "off-rates") from the target molecule.

As used herein "binding" generally refers to the formation of a non-covalent association between the ligand and the target, although such binding is not necessarily reversible. The terms "nucleic acid-target complex" or "complex" or "affinity complex" are used to refer to the product of such non-covalent binding association.

In various embodiments, the slow off-rate aptamers can be single- or double-stranded RNA or DNA oligonucleotides. The aptamers can contain non-standard or modified bases. Further, the aptamers can contain any type of modification. As used herein, a "modified base" may include a relatively simple modification to a natural nucleic acid residue, which modification confers a change in the physical properties of the nucleic acid residue. Such modifications include, but are not limited to, modifications at the 5-position of pyrimidines, substitution with hydrophobic groups, e.g., benzyl, iso-butyl, indole, or napthylmethyl, or substitution with hydrophilic groups, e.g., quaternary amine or guanidinium, or more "neutral" groups, e.g., imidazole and the like. Additional modifications may be present in the ribose ring, e.g., 2'-position, such as 2'-amino (2'-$NH_2$) and 2'-fluoro (2'-F), or the phosphodiester backbone, e.g., phosphorothioates or methyl phosphonates.

In various embodiments, a candidate mixture containing a randomized set of nucleic acid sequences containing modified nucleotide bases is mixed with a quantity of the target molecule and allowed to establish binding equilibrium with the target molecule. Generally, only some of those nucleic acids that bind with high affinity to the target molecule will efficiently partition with the target.

In various embodiments, the candidate mixture includes nucleic acid sequences having variable regions that include modified groups. The modified groups can be modified nucleotide bases. The variable region can contain fully or partially random sequences; it can also contain sub-portions of a fixed sequence that is incorporated within the variable region. The nucleotides within the fixed regions can also contain modified nucleotide bases, or they can contain the standard set of naturally occurring bases.

In some embodiments, amplification occurs after members of the test mixture have been partitioned, and it is the nucleic acid that is amplified. For example, amplifying RNA molecules can be carried out by a sequence of three reactions: making cDNA copies of selected RNAs, using the polymerase chain reaction to increase the copy number of each cDNA, and transcribing the cDNA copies to obtain RNA molecules having the same sequences as the selected RNAs. Any reaction or combination of reactions known in the art can be used as appropriate, including direct DNA replication, direct RNA amplification and the like, as will be recognized by those skilled in the art. The amplification method may result in the proportions of the amplified mixture being representative of the proportions of different sequences in the mixture prior to amplification. It is known that many modifications to nucleic acids are compatible with enzymatic amplification. Modifications that are not compatible with amplification can be made after each round of amplification, if necessary.

The nucleic acid candidate mixture can be modified in various ways to enhance the probability of the nucleic acids having facilitating properties or other desirable properties, particularly those that enhance the interaction between the nucleic acid and the target. Contemplated modifications include modifications that introduce other chemical groups that have the correct charge, polarizability, hydrogen bonding, or electrostatic interaction to enhance the desired ligand-target interactions. The modifications that may enhance the binding properties, including the affinity and/or dissociation rates, of the nucleic acid, for example, include hydrophilic moieties, hydrophobic moieties, rigid structures, functional groups found in proteins such as imidazoles, primary alcohols, carboxylates, guanidinium groups, amino groups, thiols and the like. Modifications can also be used to increase the survival of aptamer-target complexes under stringent selection pressures that can be applied to produce slow off-rate aptamers to a wide range of targets. In one embodiment, BndU (5-(N-benzylcarboxyamide)-dU) is used in the generation of the candidate mixtures used to produce slow off-rate aptamers, although other modified nucleotides are well suited to the production of such aptamers. Other modified nucleotides are shown in FIG. 14. A modified nucleotide candidate mixture for the purpose of this application is any RNA or DNA candidate mixture that includes both naturally occurring and other than the naturally occurring nucleotides. Suitable modifications include modifications on every residue of the nucleic acid, on a single residue of the nucleic acid, on random residues, on all pyrimidines or all purines, on all occurrences of a specific base (i.e., G, C, A, T or U) in the nucleic acid, or any other modification scheme that may be suitable for a particular application. It is recognized that modification is not a prerequisite for facilitating activity or binding ability of the aptamers. Aptamers may include modified dUTP and dCTP residues.

Candidate mixtures for slow off-rate aptamers may comprise a set of pyrimidines having a different modification at the C-5 base position. The C-5 modification may be introduced through an amide linkage, directly, or indirectly, or through another type of linkage. These candidate mixtures are used in a SELEX process to identify slow off-rate aptamers. This process may be also include the use of the slow off-rate enrichment process. Candidate mixtures may be produced enzymatically or synthetically.

As described above, the nucleotides can be modified in any number of ways, including modifications of the ribose and/or phosphate and/or base positions. Certain modifications are described in U.S. Pat. No. 5,660,985 entitled "High Affinity Nucleic Acid Ligands Containing Modified Nucleotides," U.S. Pat. No. 5,428,149 entitled "Method for Palladium Catalyzed Carbon-Carbon Coupling and Products," U.S. Pat. No. 5,580,972 entitled "Purine Nucleoside Modifications by Palladium Catalyzed Methods," all of which are incorporated by reference herein. In one embodiment, modifications are those wherein another chemical group is attached to the 5-position of a pyrimidine or the 2' position of a sugar. There is no limitation on the type of other chemical group that can be incorporated on the individual nucleotides. In some embodiments, the resulting modified nucleotide is amplifiable or can be modified subsequent to the amplification steps (see, e.g., U.S. Pat. No. 6,300,074 entitled "Systematic evolution of ligands by exponential enrichment: Chemi-SELEX".

In yet other embodiments, certain nucleotides are modified to produce aptamers that bind and form a covalent crosslink to their target molecule upon photo-activation of the affinity complex. This method encompasses aptamers that bind, photocrosslink, and/or photoinactivate target molecules. In various embodiments, the aptamers contain photoreactive groups that are capable of photocrosslinking to the target molecule upon irradiation with light. In other embodiments, the aptamers are capable of bond formation with the target in the absence of irradiation.

A photoreactive group can be any chemical structure that contains a photochromophore and that is capable of photocrosslinking with a target molecule. Although referred to herein as a photoreactive group, in some cases, as described below, irradiation is not necessary for covalent binding to occur between the aptamer and the target. In some embodiments, the photoreactive group will absorb light of a wavelength that is not absorbed by the target or the non-modified portions of the oligonucleotide. Photoreactive groups include 5-halo-uridines, 5-halo-cytosines, 7-halo-adenosines, 2-nitro-5-azidobenzoyls, diazirines, aryl azides, fluorinated aryl azides, benzophenones, amino-benzophenones, psoralens, anthraquinones, etc.

The photoreactive groups generally form bonds with the target upon irradiation of the associated nucleic acid-target pair. In some cases, irradiation is not required for bond formation to occur. The photocrosslink that typically occurs will be the formation of a covalent bond between the associated aptamer and the target. However, a tight ionic interaction between the aptamer and target may also occur upon irradiation.

In one embodiment, photocrosslinking occurs due to exposure to electromagnetic radiation. Electromagnetic radiation includes ultraviolet light, visible light, X-ray, and gamma ray.

In various other embodiments, a limited selection of oligonucleotides using a SELEX method is followed by selection using a photoSELEX method. The initial SELEX selection rounds are conducted with oligonucleotides containing photoreactive groups. After a number of SELEX rounds, photoSELEX is conducted to select oligonucleotides capable of binding the target molecule. In another embodiment, the production of an aptamer that includes a cleavable or releasable section (also described as an element or component) in the aptamer sequence is described. These additional components or elements are structural elements or components that introduce additional functionality into the aptamer and are thus functional elements or components. The aptamer is further produced with one or more of the following additional components (also described as a functional or structural element or component or moiety in any combination of these terms): a labeled or detectable component, a spacer component, and a specific binding tag or immobilization element or component.

As noted above, the present disclosure provides methods for identifying aptamers that bind one or more targets of interest within a cell or tissue sample and once bound have slow rates of dissociation or off-rates. The slow off-rates obtained with this method can exceed a half-life of about one hour and as much as about 240 minutes, that is, once a set of nucleic acid-target complexes is generated, half of the complexes in the set remain bound after one hour. Because the effect of a slow off-rate enrichment process depends upon the differing dissociation rates of aptamer affinity complexes, the duration of the slow off-rate enrichment process is chosen so as to retain a high proportion of aptamer affinity complexes with slow dissociation rates while substantially reducing the number of aptamer affinity complexes with fast dissociation rates. For example, incubating the mixture for relatively longer periods of time after imposing the slow off-rate enrichment process will select for aptamers with longer dissociation rates than aptamers selected using slow off-rate enrichment process having shorter incubation periods.

In various embodiments, the candidate mixture is mixed with a quantity of the cell or tissue sample and allowed to establish binding equilibrium with the target or targets of interest. Prior to partitioning the target bound nucleic acids from those free in solution, a slow off-rate enrichment process is imposed to enrich the bound population for slow dissociation rates. As noted above, the slow off-rate enrichment process can be applied by the addition of a competitor molecule, by sample dilution, by a combination of sample dilution in the presence of a competitor molecule. Thus, in one embodiment, the slow off-rate enrichment process is applied by introducing competitor molecules into the mixture containing the nucleic acid-target complexes and incubating the mixture for some period of time before partitioning free from bound nucleic acids. The amount of competitor molecules is generally at least one order of magnitude higher than that of the nucleic acid molecules and may be two or more orders of magnitude higher. In another embodiment, the slow off-rate enrichment process is applied by diluting the sample mixture of nucleic acid-target complexes several fold (e.g. at least about one of 2×, 3×, 4×, 5×) in volume and incubating the mixture for some period of time before partitioning free from bound nucleic acids. The dilution volume is generally at least one order of magnitude higher, and may be about two or more orders of magnitude higher, than the original volume. In yet another embodiment, a combination of both competitor molecules and dilution is used to apply the slow off-rate enrichment process. In another embodiment, candidate mixtures that have been shown to result in an increased frequency of slow dissociation aptamers are used to select a number of candidate aptamers. These aptamers are screened to identify slow dissociation rate aptamers.

In another embodiment, a slow off-rate aptamer that includes a cleavable or releasable section in the fixed region of the aptamer is produced. The aptamer can also be produced with one or more of the following additional components: a labeled component, a spacer component, and a specific binding tag. Any or all of these elements may be introduced into a single stranded aptamer. In one embodiment, the element is introduced at the 5' end of the aptamer. In another embodiment, one or more of these elements is included by creating a partially double stranded aptamer, where one strand contains the various elements desired as well as a sequence complementary to one of the fixed sequence sections of the second strand containing the variable target binding region.

A "releasable" or "cleavable" element or moiety or component refers to a functional group where certain bonds in the functional group can be broken to produce 2 separate components. In various embodiments, the functional group can be cleaved by irradiating the functional group (photocleavable) at the appropriate wavelength or by treatment with the appropriate chemical or enzymatic reagents. In another embodiment, the releasable element may be a disulfide bond that can be treated with a reducing agent to disrupt the bond. The releasable element allows an aptamer/target affinity complex that is attached to a solid support to be separated from the solid support, such as by elution of the complex. The releasable element may be stable to the conditions of the rest of the assay and may be releasable under conditions that will not disrupt the aptamer/target complex.

Figure 9A:
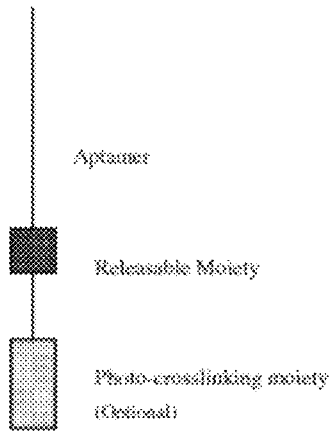
FIGS. 9A to 9D illustrate aptamer constructs that contain a variety of different and optional functionalities including immobilization tags, labels, photocrosslinking moieties, spacers, and releasable moieties.
Figure 9B:
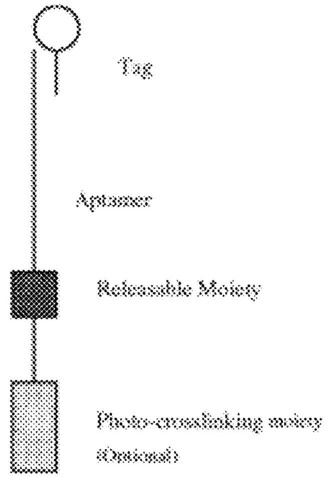
Figure 9C:
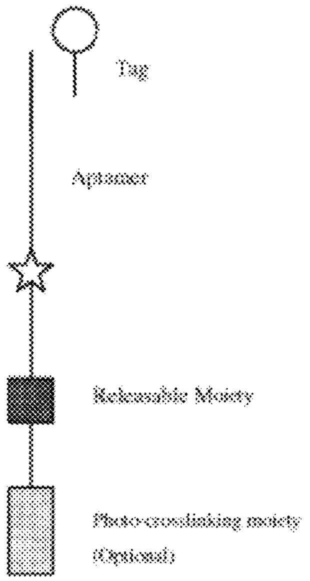
Figure 9D:
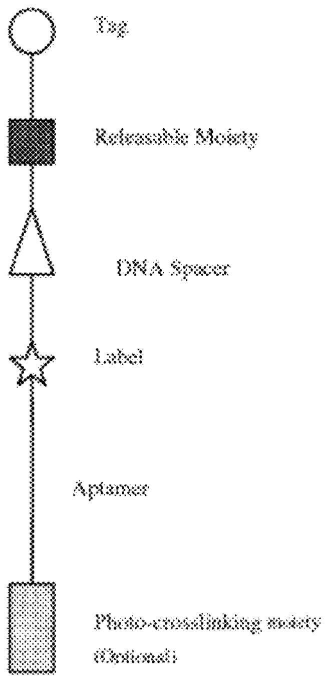
Figure 10A:
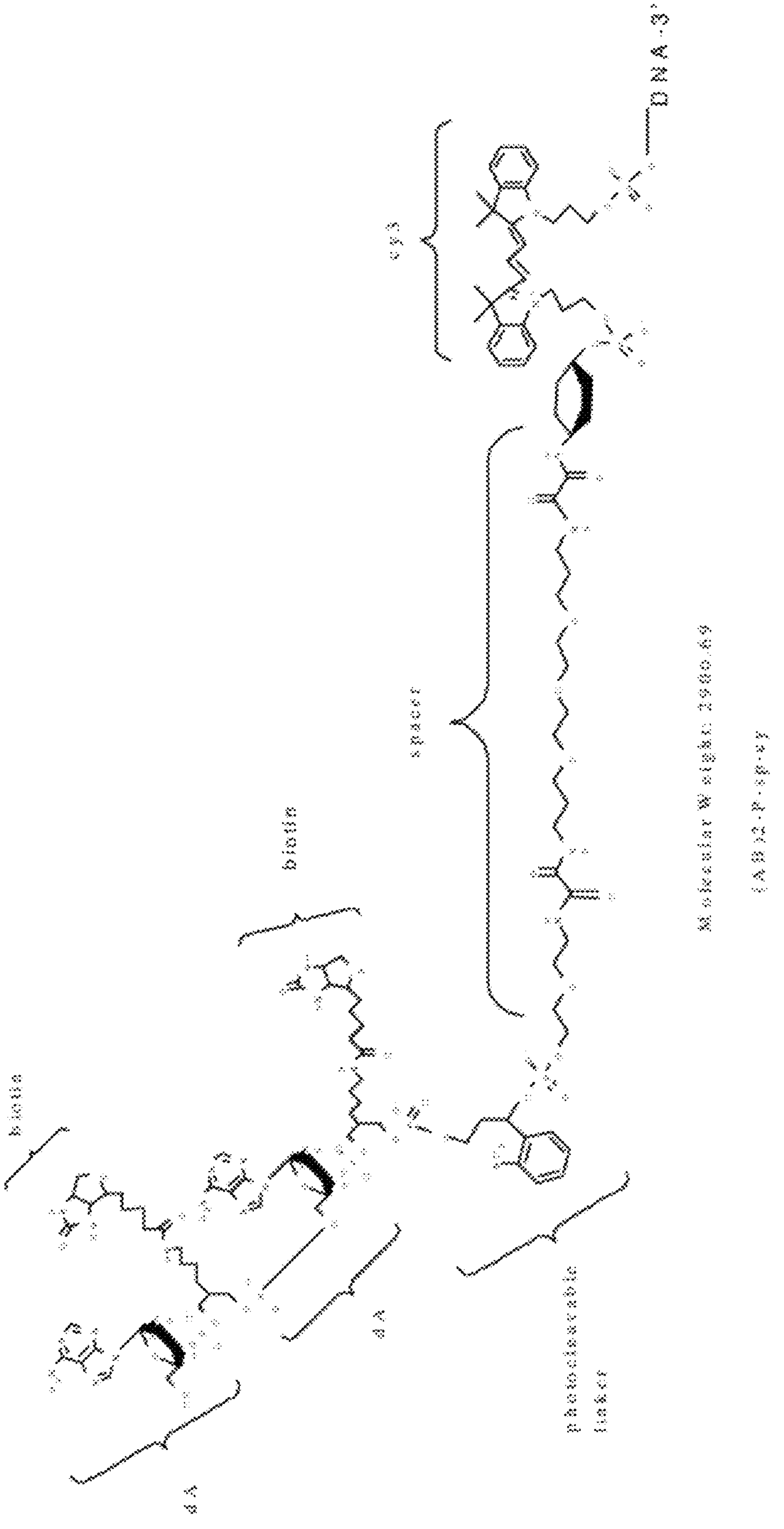
FIGS. 10A to 10F illustrate examples of aptamer constructs including a cleavable or releasable element, a tag (for example biotin), a spacer, and a label (for example Cy3).
Figure 10B:
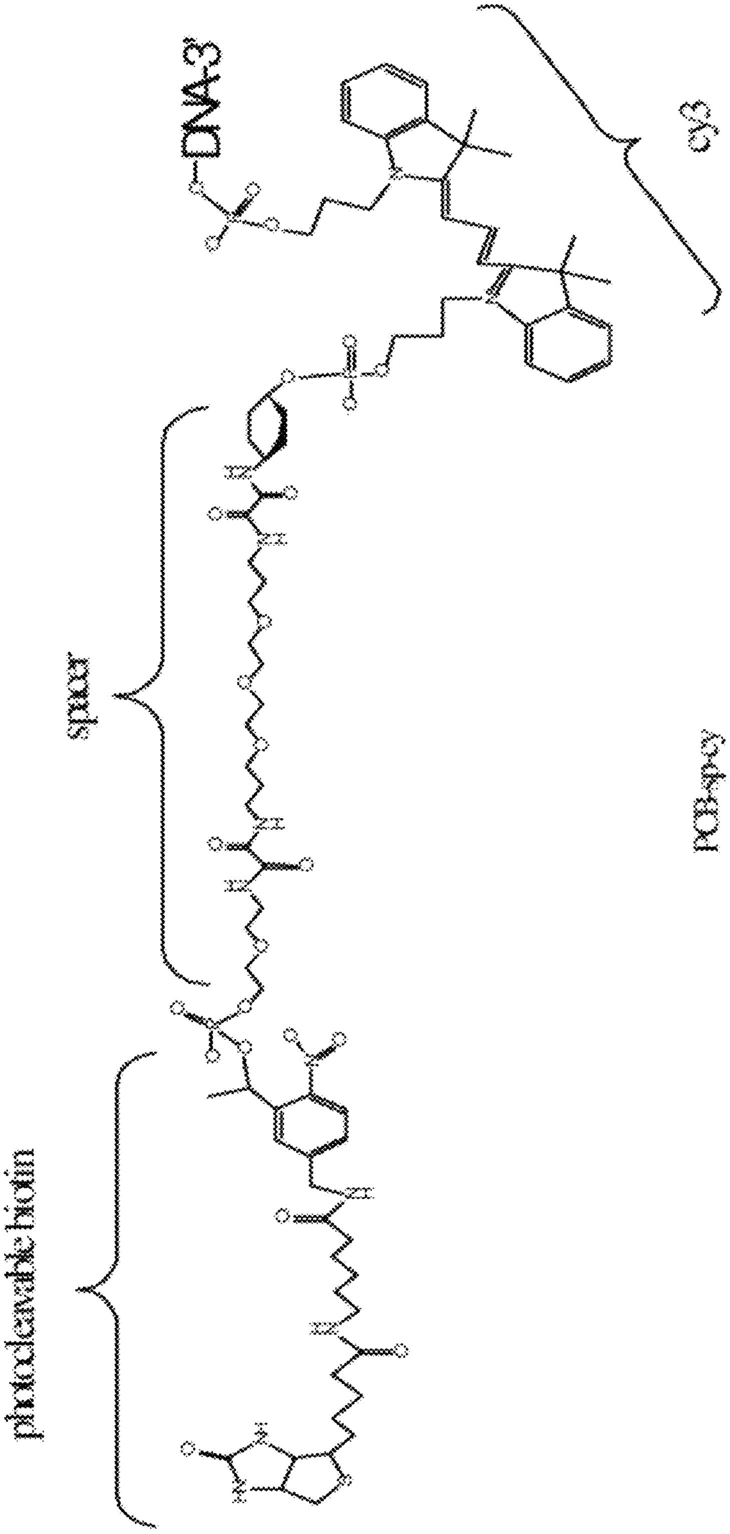
Figure 10C:
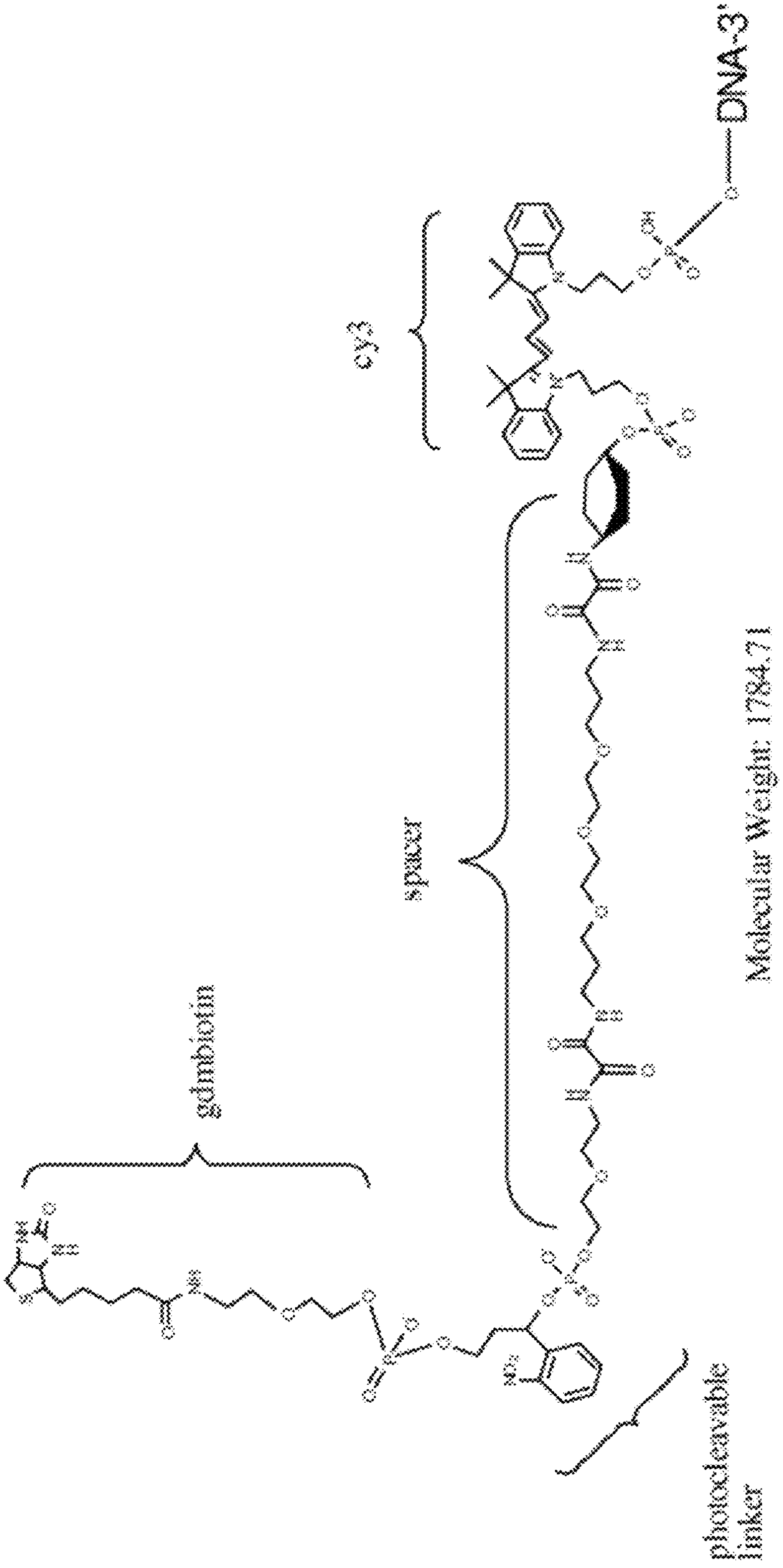
Figure 10D:
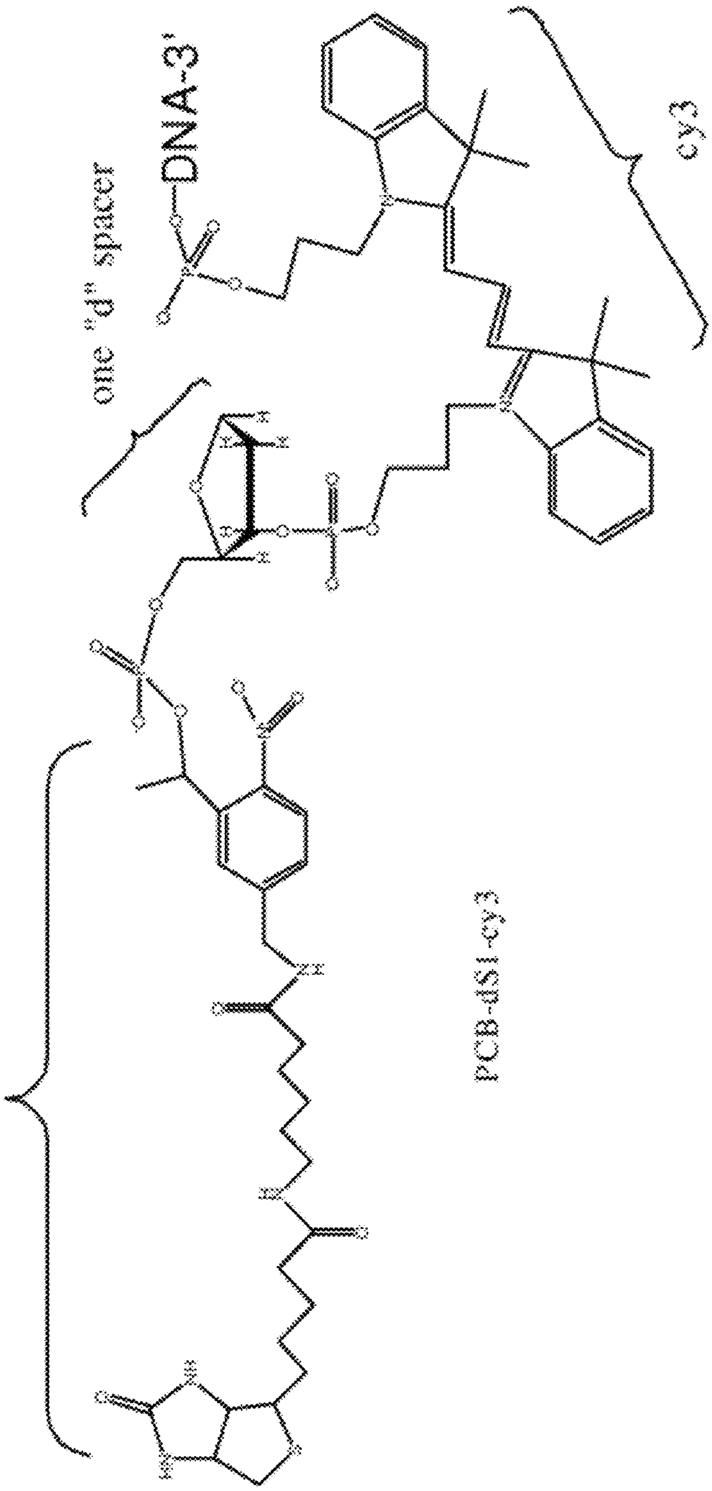
Figure 10E:
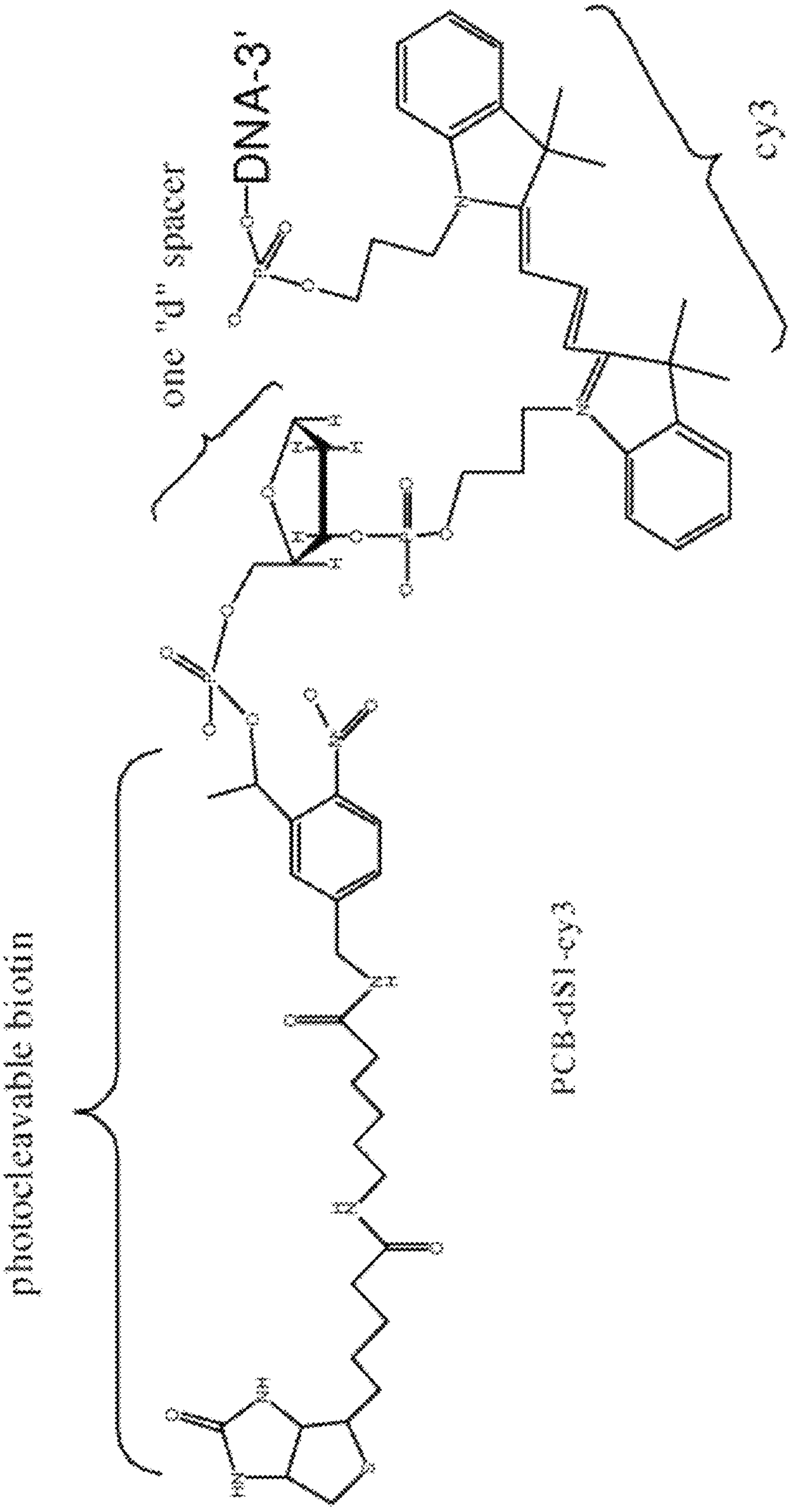
Figure 10F:
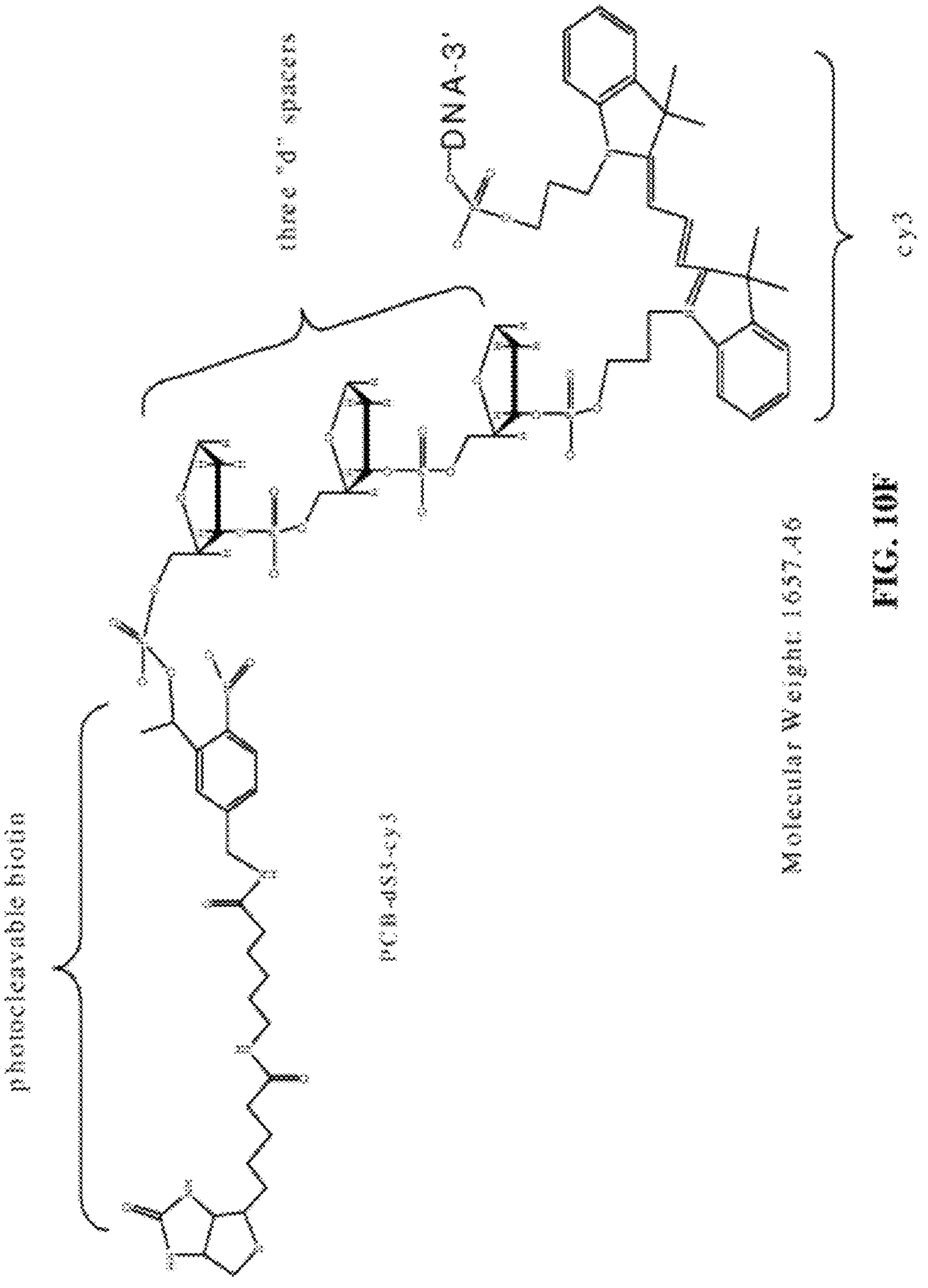

As disclosed herein, an aptamer can further comprise a "tag" or "immobilization component or element" or "specific binding component or element" which refers to a component that provides a means for attaching or immobilizing an aptamer (and any target molecule that is bound to it) to a solid support. A "tag" is a set of copies of one type or species of component that is capable of associating with a probe. "Tags" refers to more than one such set of components. The tag can be attached to or included in the aptamer by any suitable method. Generally, the tag allows the aptamer to associate, either directly or indirectly, with a probe or receptor that is attached to the solid support. The probe may be highly specific in its interaction with the tag and retain that association during all subsequent processing steps or procedures. A tag can enable the localization of an aptamer affinity complex (or optional covalent aptamer affinity complex) to a spatially defined address on a solid support. Different tags, therefore, can enable the localization of different aptamer covalent complexes to different spatially defined addresses on a solid support. A tag can be a polynucleotide, a polypeptide, a peptide nucleic acid, a locked nucleic acid, an oligosaccharide, a polysaccharide, an antibody, an affybody, an antibody mimic, a cell receptor, a ligand, a lipid, biotin, any fragment or derivative of these structures, any combination of the foregoing, or any other structure with which a probe (or linker molecule, as described below) can be designed or configured to bind or otherwise associate with specificity. Generally, a tag is configured such that it does not interact intramolecularly with either itself or the aptamer to which it is attached or of which it is a part. If SELEX is used to identify an aptamer, the tag may be added to the aptamer either pre- or post-SELEX. The tag is included on the 5'-end of the aptamer post-SELEX, or the tag is included on the 3'-end of the aptamer post-SELEX, or the tags may be included on both the 3' and 5' ends of the aptamers in a post-SELEX process. As illustrated in FIG. 9D, a fluorescent dye (such as Cy3), the photocleavable and biotin moieties are all added to the end of the aptamer. Because of potential interactions between the photocleavable moiety and the dye, a spacer is inserted between these two moieties. All constructs can be synthesized using standard phosphoramidite chemistry. Representative aptamer constructs are shown in FIG. 10A through FIG. 10F. The functionality can be split between the 5' and 3' end or combined on either end. In addition to photocleavable moieties, other cleavable moieties can be used, including chemically or enzymatically cleavable moieties. A variety of spacer moieties can be used and one or more biotin moieties can be included. Tags (also referred to as immobilization or specific binding elements or components) other than biotin can also be incorporated. Suitable construction reagents include biotin phosphoramidite, PC Linker (Glen Research PN 10-4920-02); PC biotin phosphoramidite (Glen Research PN 10-4950-02); dSpacer CE phosphoramidite (Glen Research PN 10-1914-02); Cy3 phosphoramidite (Glen Research PN 10-5913-02); and Arm26-Ach Spacer Amidite (Fidelity Systems PN SP26Ach-05). This type of tag on a target specific slow off-rate aptamer may be used to introduce secondary reagents, such as a label, into a tissue or cell sample. For example if the slow off-rate aptamer contains a biotin tag, a labeled avidin molecule could be introduced to generate signal.

In one embodiment, base modifications of the nucleotides are used in the production of the variable region of the aptamer. These modified nucleotides have been shown to produce aptamers that have very slow off-rates from their targets. In the methods of the present disclosure the candidate mixture may comprise modified nucleic acids in which one, several (e.g. one of, or at least one of, 2, 3, 4, 5, 6, 7, 8, 9, 10, 11, 12, 13, 14, 15, 16, 17, 18, 19, 20, 21, 22, 23, 24, 25, 26, 27, 28, 29, 30) or all pyrimidines in at least one, or each, nucleic acid of the candidate mixture is chemically modified at the 5-position. Optionally, all C residues in the nucleic acids of the candidate mixture are chemically modified at the 5-position. Optionally, all T residues in the nucleic acids of the candidate mixture are chemically modified at the 5-position. Optionally, all U residues in the nucleic acids of the candidate mixture are chemically modified at the 5-position.

A "cytological specimen or sample" may include a wide range of specimen types. These include abdominal and pelvic washings, body cavity fluids (pleural, peritoneal), urine, gastric/esophageal washings, fine needle aspirates (FNA), breast fluid, CSF, cyst fluid, synovial fluid, and bronchial washings. Smears may be prepared from FNA specimens or brush collected specimens as is done for PAP Smears.

A "cytology protocol" generally consists of sample collection, sample fixation, sample immobilization, and staining. "Cell preparation" may include all of the processing steps after sample collection including the use of one or more slow off-rate aptamer for the staining of the prepared cells.

Sample collection may involve directly placing the sample in an untreated transport container, placing the sample in a transport container containing some type of media, or placing the sample directly onto a slide (immobilization) without any treatment or fixation.

Sample immobilization may be improved by applying a portion of the collected specimen to a glass slide that is treated with polylysine, gelatin, or a silane. Slides may be prepared by smearing a thin and even layer of cells across the slide. Care is taken to minimize mechanical distortion and drying artifacts. Liquid specimens may be processed in a cell block method or liquid specimens may be mixed 1:1 with the fixative solution for 10 minutes at room temperature.

Cell blocks may be prepared from residual effusions, sputum, urine sediments, gastrointestinal fluids, cell scraping, or fine needle aspirates. Cells are concentrated or packed by centrifugation or membrane filtration. A number of methods for cell block preparation have been developed. Representative procedures include the fixed sediment, bacterial agar, or membrane filtration methods. In the fixed sediment method, the cell sediment is mixed with a fixative like Bouin's, picric acid, or buffered formalin and then the mixture is centrifuged to pellet the fixed cells. The supernatant is removed, drying the cell pellet as completely as possible. The pellet is collected and wrapped in lens paper and then placed in a tissue cassette. The tissue cassette is placed in a jar with additional fixative and processed as a tissue sample. Agar method is very similar but the pellet is removed and dried on paper towel and then cut in half. The cut side is placed in a drop of melted agar on a glass slide and then the pellet is covered with agar making sure that no bubbles form in the agar. The agar is allowed to harden and then any excess agar is trimmed away. This is placed in a tissue cassette and the tissue process completed. Alternatively, the pellet may be directly suspended in 2% liquid agar at 65° C. and the sample centrifuged. The agar cell pellet is allowed to solidify for an hour at 4° C. The solid agar may be removed from the centrifuge tube and sliced in half. The agar is wrapped in filter paper and then the tissue cassette. Processing from this step on is as above. The centrifugation steps may be replaced in any these procedures with a membrane filtration step. Any of these processes may be used to generate a "cell block sample".

Cell blocks may be prepared using specialized resins including Lowicryl resins, L R White, L R Gold, Unicryl, and MonoStep. These resins have low viscosity and can be polymerized, at low temperatures and ultra violet (UV) light. The embedding process relies on progressively cooling the sample during the dehydration steps, transferring the sample to the resin and polymerizing a block at the final low temperature at the appropriate UV wavelength.

Cell block sections may be stained with hematoxylin-eosin for cytomorphological examination while additional sections are used for examination for specific markers.

Whether the process is cytological or histological, the sample may be fixed prior to additional processing to prevent sample degradation. This step is called "fixation" and describes a wide range of materials and procedures that may be used interchangeably. The sample fixation protocol and reagents are best selected empirically based on the targets to be detected and the specific cell/tissue type to be analyzed. Sample fixation relies on reagents such as ethanol, polyethylene glycol, methanol, formalin, or isopropanol. The samples should be fixed as soon after collection and affixation to the slide as possible. However, the fixative selected can introduce structural changes into various molecular targets making their subsequent detection more difficult. The fixation and immobilization processes and their sequence can modify the appearance of the cell and these changes must be anticipated and recognized by the cytotechnologist. Fixatives can cause shrinkage of certain cell types and cause the cytoplasm to appear granular or reticular. Many fixatives function by crosslinking cellular components. This can damage or modify specific epitopes, generate new epitopes, cause molecular associations, and reduce membrane permeability. Formalin fixation is one of the most common cytological/histological approaches. Formalin forms methyl bridges between neighboring proteins or within proteins. Precipitation or coagulation is also used for fixation and ethanol is frequently used in this type of fixation. A combination of crosslinking and precipitation can also be used for fixation. A strong fixation process is best at preserving morphological information while a weaker fixation process is best the preservation of molecular targets.

A representative fixative would be 50% absolute ethanol, 2 mM polyethylene glycol (PEG), 1.85% formaldehyde. Variations on this formulation include ethanol (50% to 95%), methanol (20%-50%), and formalin (formaldehyde) only. Another common fixative is 2% PEG 1500, 50% ethanol, and 3% methanol. Slides are place in the fixative for 10 to 15 minutes at room temperature and then removed and allowed to dry. Once slides are fixed they can be rinsed with a buffered solution like PBS.

A wide range of dyes can be used to differentially highlight and contract or "stain" cellular, sub-cellular, and tissue features or morphological structures. Hematoylin is used to stain nuclei a blue or black color. Orange G-6 and Eosin Azure both stain the cell's cytoplasm. Orange G stains keratin and glycogen containing cells yellow. Eosin Y is used to stain nucleoli, cilia, red blood cells, and superficial epithelial squamous cells. Romanowsky stains are used for air dried slides and are useful in enhancing pleomorphism and distinguishing extracellular from intra-cytoplasmic material.

The staining process may involve a treatment to increase the permeability of the cells to the stain. Treatment of the cells with a detergent may be used to increase permeability. To increase cell and tissue permeability fixed samples may be further treated with solvents, saponins, or non-ionic detergents. Enzymatic digestion may also improve the accessibility of specific targets in a tissue sample.

After staining the sample is dehydrated using a succession of alcohol rinses with increasing alcohol concentration. The final wash is done with xylene or a xylene substitute, such as a citrus terpene, that has a refractive index close to that of the coverslip to be applied to the slide. This final step is referred to as clearing. Once the sample is dehydrated and cleared a mounting medium is applied. The mounting medium is selected to have a refractive index close to the glass and is capable of bonding the coverslip to the slide. It will also prevent the additional drying, shrinking, or fading of the cell sample.

Regardless of the stains or processing steps used the final evaluation of the cytological specimen is made by some type of microscopy and a visual inspection of the morphology and determination of the marker presence or absence. Microscopic methods utilized include brightfield, phase contract, fluorescence, and differential interference contrast.

If secondary tests are required on the sample after examination, the coverslip may be removed and the slide destained. Destaining involves using the original solvent systems used in staining the slide originally without the added dye and in a reverse order to the original staining procedure. Destaining may also be completed by soaking the slide in an acid alcohol until the cells are colorless. Once colorless the slides are rinsed well in a water bath and the second staining procedure applied.

In addition, specific molecular differentiation may be possible in conjunction with the cellular morphological analysis through the use of specific molecular reagents such as antibodies or nucleic acid probes. This improves the accuracy of diagnostic cytology. Micro-dissection may be used to isolate a subset of cells for additional evaluation, in particular, for genetic evaluation of abnormal chromosomes, gene expression, or mutations.

In histology, tissue specimens may be collected from epithelium, connective tissues, cartilage, bone, muscle, nerves, vessels, heart, lymphatic system, respiratory tract, urinary tract, endocrine system, and reproductive system.

Preparation of a tissue sample for histological evaluation involves fixation, dehydration, infiltration, embedding, and sectioning. The fixation reagents used in histology are very similar or identical to those used in cytology and have the same issues of preserving morphological features at the expense of molecular ones such as individual proteins. Time can be saved if the tissue sample is not fixed and dehydrated but instead is frozen and then sectioned while frozen. This is a more gentle processing step and can preserve more individual markers. However, freezing is not acceptable for long term storage of a tissue sample as subcellular information is lost due to the introduction of ice crystals. Ice in the frozen tissue sample also prevents the sectioning process from producing a very thin slice and thus some microscopic resolution and imaging of subcellular structures can be lost. In addition to formalin fixation, osmium tetroxide is used to fix and stain phospholipids (membranes).

Dehydration of tissues is accomplished with successive washes of increasing alcohol concentration. Clearing requires a material that is miscible with alcohol and the embedding material and involves a stepwise process starting at 50:50 alcohol:clearing reagent and then 100% clearing agent (xylene or xylene substitute). Infiltration involves incubating the tissue with a liquid form of the embedding agent (warm wax, nitrocellulose solution) first at 50:50 embedding agent: clearing agent and the 100% embedding agent. Embedding is completed by placing the tissue in a mold or cassette and filling with melted embedding agent such as wax, agar, or gelatin. The embedding agent is allowed to harden. The harden tissue sample may then be sliced into thin section for staining and subsequent examination.

Prior to staining, the tissue section is dewaxed and rehydrated. Xylene is used to dewax the section, one or more changes of xylene may be used, and the tissue is rehydrated by successive washes in alcohol of decreasing concentration. Prior to dewax the tissue section may be heat immobilized to a glass slide at 80° C. for 20 minutes. Histology stains are listed in FIG. 1.

Laser capture micro-dissection allows the isolation of a subset of cells for further analysis from a tissue section.

As in cytology, to enhance the visualization of the microscopic features, the tissue section or slice may be stained with a variety of stains. A large menu of stains are available to enhance or identify specific features.

To further increase the interaction of immunological reagents with cytological/histological samples a number of techniques for "antigen retrieval" have been developed. The first such technique relied on high temperature heating of a fixed sample. This method is also referred to as heat-induced epitope retrieval or HIER. A variety of heating techniques have been used, including steam heating, microwaving, autoclaving, water baths, and pressure cooking or a combination of these methods of heating. Antigen retrieval solutions include water, citrate, or normal saline buffers. The key to antigen retrieval is the time at high temperature but lower temperatures for longer times have also been successfully used. Another key to antigen retrieval is the pH of the heating solution. Low pH was found to provide the best immunostaining but also gave rise to backgrounds that required the use of a second tissue section as a negative control. The most consistent benefit (increased immunostaining without increase in background) was found with a high pH solution regardless of the buffer composition. The antigen retrieval process for a specific target should be empirically optimized for that target using heat, time, pH, and buffer composition as variables for process optimization. Using the microwave antigen retrieval method has allowed for sequential staining of different targets with antibody reagents. But the time required to antibody and enzyme complexes between staining steps has also been shown to degrade cell membrane antigens. Microwave heating methods have improved in situ hybridization methods as well.

To initiate the antigen retrieval process, the section is first dewaxed and hydrated. The slide is then placed in 10 mM sodium citrate buffer pH 6.0 in a dish or jar. A representative procedure uses an 1100 W microwave and microwaves the slide at 100% power for 2 minutes followed by microwaving the slides using 20% power for 18 minutes after checking to be sure the slide remains covered in liquid. The slide is then allowed to cool in the uncovered container and then rinsed with distilled water. HIER may be used in combination with an enzymatic digestion to improve the reactivity of the target to immunochemical reagents.

One such enzymatic digestion protocol uses proteinase K. A 20 μg/ml concentration of proteinase K is prepared in 50 mM Tris Base, 1 mM EDTA, 0.5% Triton X-100, pH 8.0 buffer. The process first involves dewaxing sections in 2 changes of xylene, 5 minutes each. Then the sample is hydrated in 2 changes of 100% ethanol for 3 minutes each, 95% and 80% ethanol for 1 minute each and then rinsed in distilled water. Sections are covered with Proteinase K working solution and incubated 10-20 minutes at 37° C. in humidified chamber (optimal incubation time may vary depending on tissue type and degree of fixation). The sections are cooled at room temperature for 10 minutes and then rinsed in PBS Tween 20 for 2×2 min. If desired sections may be blocked to eliminate potential interference from endogenous compounds and enzymes. The section is then incubated with primary antibody at appropriate dilution in primary antibody dilution buffer for 1 hour at room temperature or overnight at 4° C. The section is then rinsed with PBS Tween 20 for 2×2 min. Additional blocking may be performed if required for the specific application followed by additional rinsing with PBS Tween 20 for 3×2 min and then finally the immunostaining protocol completed.

A simple treatment with 1% SDS at room temperature has also been demonstrated to improve immunohistochemical staining. Antigen retrieval methods have been applied to slide mounted sections as well as free floating sections. Another treatment option is to place the slide in a jar containing citric acid and 0.1 Nonident P40 at pH 6.0 and heating to 95° C. The slide is then washed with a buffer solution like PBS.

For immunological staining of tissues it may be useful to block non-specific association of the antibody with tissue proteins by soaking the section in a protein solution like serum or non-fat dry milk.

An "slow off-rate aptamer treated sample" is intended to mean any cytological or histological slide or section that may be treated with one or more slow off-rate aptamers to one or more targets to be detected. The treatment process may include placing the slide or section in one or more buffer or reagent at one or more temperatures for a period of time sufficient to complete the desired interaction between the slow off-rate aptamer and target, the slow off-rate aptamer and subsequent detection moiety, partitioning, blocking reactions, or other process steps.

Blocking reactions may include the need to reduce the level of endogenous biotin; eliminate endogenous charge effects; inactivate endogenous nucleases; and/or inactivate endogenous enzymes like peroxidase and alkaline phosphatase. Endogenous nucleases may be inactivated by degradation with proteinase K, by heat treatment, use of a chelating agent such as EDTA or EGTA, the introduction of carrier DNA or RNA, treatment with a chaotrope such as urea, thiourea, guanidine hydrochloride, guanidine thiocyanate, lithium perchlorate, etc, or diethyl pyrocarbonate. Alkaline phosphatase may be inactivated by treated with 0.1N HCl for 5 minutes at room temperature or treatment with 1 mM levamisole. Peroxidase activity may be eliminated by treatment with 0.03% hydrogen peroxide. Endogenous biotin may be blocked by soaking the slide or section in an avidin (streptavidin, neutravidin may be substituted) solution for at least 15 minutes at room temperature. The slide or section is then washed for at least 10 minutes in buffer. This may be repeated at least three times. Then the slide or section is soaked in a biotin solution for 10 minutes. This may be repeated at least three times with a fresh biotin solution each time. The buffer wash procedure is repeated. All slides or sections used for a single diagnostic purposes should be treated with the same blocking protocol. Blocking protocols should be minimized to prevent damaging either the cell or tissue structure or the target or targets of interest but one or more of these protocols could be combined to "block" a slide or section prior to reaction with one or more slow off-rate aptamers.

In one embodiment, a cytological sample may be collected, applied to a glass slide, fixed, stained for the structural/morphological features appropriate to the sample collected and disease state to be diagnosed, microscopically examined, and then may be reacted with one or slow off-rate aptamers to the desired target or targets. The method may further include one or more of the following steps; an antigen retrieval step; treating to increase the cell permeability (permeabilizing); one or more blocking step; dehydrating; clearing; wash steps; and/or a destaining step. The sequence of the individual steps may be interchanged as needed. The slow off-rate aptamers may optionally be designed to crosslink with their specific target.

In one embodiment, a cytological sample may be collected, applied to a glass slide, fixed, stained for the structural/morphological features appropriate to the sample collected and disease state to be diagnosed, microscopically examined, and then may be reacted with one or crosslinking slow off-rate aptamers or photoaptamers to the desired target or targets. The method may further include one or more of the following steps; an antigen retrieval step; treating to increase the cell permeability (permeabilizing); dehydrating; clearing; one or more blocking step; wash steps; and/or a destaining step. The sequence of the individual steps may be interchanged as needed but includes an additional step to activate the crosslinking process.

In another embodiment sections from a cell block procedure may be utilized. When a cell block is used the sample may be prepared as if it were a tissue sample. One section may be stained as is appropriate to the cell type and disease state to be diagnosed. Another section may be treated with the one or more slow off-rate aptamers for detection of specific target or targets. And another section may be treated with the same reagents and sequence as the slow off-rate aptamer treated section in the absence of the one or more slow off-rate aptamers to serve as a negative control section. Optionally these slow off-rate aptamers may be crosslinking slow off-rate aptamers or photoaptamers. These procedures may be applied to tissue sections.

In some embodiments, once the slow off-rate aptamer(s) is allowed to equilibrate with the tissue or cell sample to form an slow off-rate aptamer target affinity complex, a kinetic challenge may be used. If a kinetic challenge is introduced, non-specific complexes between the slow off-rate aptamer and any non-target molecules are unlikely to re-form following their dissociation. Since non-specific complexes generally dissociate more rapidly than an slow off-rate aptamer affinity complex, a kinetic challenge reduces the likelihood that an slow off-rate aptamer will be involved in a non-specific complex with a non-target. An effective kinetic challenge can provide the assay with additional specificity, beyond that of the initial slow off-rate aptamer binding event and any subsequent optional covalent interaction. Thus, the kinetic challenge offers a second determinant of specificity. In one embodiment, 10 mM dextran sulfate is added to the slow off-rate aptamer affinity complexes that are tissue or cell associated, and is incubated for about 15 minutes. In another embodiment, the kinetic challenge is initiated in the presence of 10 mM dextran sulfate. In the case of a kinetic challenge that uses a competitor, the competitor can also be any molecule that can form a non-specific complex with a free slow off-rate aptamer, for example to prevent that slow off-rate aptamer from rebinding non-specifically to a non-target molecule. Such competitor molecules include polycations (e.g., spermine, spermidine, polylysine, and polyarginine) and amino acids (e.g., arginine and lysine). When a competitor is used as the kinetic challenge a fairly high concentration is utilized relative to the anticipated concentration of total protein or total slow off-rate aptamer present in the sample. In one embodiment, about 10 mM dextran sulfate is used as the competitor in a kinetic challenge. In one embodiment, the kinetic challenge comprises adding a competitor to the tissue or cell sample containing the slow off-rate aptamer affinity complex, and incubating the sample for a time of greater than or equal to about 30 seconds, about 1 minute, about 2 minutes, about 3 minutes, about 4 minutes, about 5 minutes, about 10 minutes, about 30 minutes, and about 60 minutes. In another embodiment, the kinetic challenge comprises adding a competitor to the tissue or cell sample containing the slow off-rate aptamer affinity complex and incubating for a time such that the ratio of the measured level of slow off-rate aptamer affinity complex to the measured level of the non-specific complex is increased.

In some embodiments, the kinetic challenge is performed by contacting the test sample with binding buffer or any other solution that does not significantly increase the natural rate of dissociation of slow off-rate aptamer affinity complexes. The dilution can be about 2×, about 3×, about 4×, about 5×, or any suitable greater dilution. Larger dilutions provide a more effective kinetic challenge by reducing the concentration of total protein and slow off-rate aptamer after dilution and, therefore, the rate of their re-association. In one embodiment, the slow off-rate aptamer affinity complex is effectively diluted by addition of the diluent and incubated for a time ≥about 30 seconds, ≥about 1 minute, ≥about 2 minutes, ≥about 3 minutes, ≥about 4 minutes, ≥about 5 minutes, ≥about 10 minutes, ≥about 30 minutes, and ≥about 60 minutes. In another embodiment, the slow off-rate aptamer affinity complex is effectively diluted by addition of a diluent and incubated for a time such that the ratio of the measured level of slow off-rate aptamer affinity complex to the measured level of the non-specific complex is increased.

In some embodiments, the kinetic challenge is performed in such a manner that the effect of sample dilution and the effect of introducing a competitor are realized simultaneously. For example, a tissue or cell sample can be effectively diluted by addition of a large volume of competitor. Combining these two kinetic challenge strategies may provide a more effective kinetic challenge than can be achieved using one strategy. In one embodiment, the effective dilution can be about 2×, about 3×, about 4×, about 5×, or any suitable greater dilution and the competitor is about 10 mM dextran sulfate. In one embodiment, the competitor is about 1 mM dextran sulfate. In one embodiment, the kinetic challenge comprises contacting the tissue or cell sample containing the slow off-rate aptamer affinity complex with a volume of diluent, adding a competitor to the mixture containing the slow off-rate aptamer affinity complex, and incubating the mixture containing the slow off-rate aptamer affinity complex for a time greater than or equal to about 30 seconds, about 1 minute, about 2 minutes, about 3 minutes, about 4 minutes, about 5 minutes, about 10 minutes, about 30 minutes, and about 60 minutes. In another embodiment, the kinetic challenge comprises diluting the mixture containing the slow off-rate aptamer affinity complex, adding a competitor to the mixture containing the slow off-rate aptamer affinity complex and incubating the mixture containing the slow off-rate aptamer affinity complex for a time such that the ratio of the measured level of slow off-rate aptamer affinity complex to the measured level of the non-specific complex is increased. In one embodiment, the crosslinking step is introduced into the procedure following the kinetic challenge step. In another embodiment, the crosslinking step is introduced into the procedure following a kinetic challenge step and a wash step.

In another embodiment a tissue specimen is collected, frozen or fixed, dehydrated, infiltrated with an embedding media, embedded in the embedding media, sliced, mounted, cleared, stained for the appropriate features for the sample collected and the disease state to be diagnosed, microscopically examined, and then reacted with one or more slow off-rate aptamers to the desired target or targets. The method may further include one or more of the following steps; an antigen retrieval step; treating to increase the tissue permeability (permeabilizing); one or more blocking step; dehydrating; wash steps; and/or a destaining step. The sequence of the individual steps may be interchanged as needed. All processes up to the first microscopic examination may be completed on free floating tissue section. Optionally these slow off-rate aptamers may be crosslinking slow off-rate aptamers or photoaptamers.

In another embodiment multiple tissue sections are used in the diagnostic procedure. One section is stained as is appropriate to the tissue type and disease state to be diagnosed for evaluation of the morphological structures and features of the tissue. Another section is treated with the one or more slow off-rate aptamers for detection of specific target or targets in a buffered solution. And another section is treated with the same reagents and sequence as the slow off-rate aptamer treated section in the absence of the one or more slow off-rate aptamers to serve as a negative control section where the slow off-rate aptamer reaction step is replaced by treatment with the buffered solution used in the slow off-rate aptamer reaction step.

In another embodiment the slide mounted smear, cell block, or tissue section may be treated to dewax the sample and then may be rehydrated prior to staining. The stain selected will be appropriate to the sample and disease state to be diagnosed. Prior to microscopic evaluation, the slide mounted sample may be covered with a coverslip. When the microscopic evaluation of the morphological or structural features is complete, then the coverslip may be removed and the sample may be optionally treated with a reagent, such as acid alcohol, to destain the sample. If a destaining protocol is used the sample should be washed several times with deionized water. To prepare the sample for reaction with one or more target specific slow off-rate aptamers, a blocking protocol may optionally be used. One embodiment uses dextran sulfate ($DexSO_4$) or another polyanionic compound as a blocking agent. Other polyanionic materials could include heparin, herring sperm DNA, salmon sperm DNA, tRNA, polydextran, abasic phosphodiester polymers, dNTPs, and pyrophosphate. In one embodiment the slow off-rate aptamer rinse solution may contain a polyanionic material like dextran sulfate. A buffered solution of one or more slow off-rate aptamers at a concentration of 1-20 nM of each slow off-rate aptamer may be used. The slow off-rate aptamer solution may be applied to the sample and incubated at room temperature or 37° C. for a period of time selected (empirically) to maximize reaction, or binding, with the specific target or targets of interest. Incubation times may be as long as 18 hours. The buffered slow off-rate aptamer solution may contain a variety of other materials such as a non-specific polynucleotide to minimize non-specific interaction of the slow off-rate aptamer/s with nucleic acid binding sites in or on the tissue or cell sample. The buffered slow off-rate aptamer solution may then be rinsed from the sample using an slow off-rate aptamer rinse solution. The coverslip may be reapplied and the sample examined microscopically for the detection one or more specific detectable moiety that may be introduced to the sample through the slow off-rate aptamer.

In another embodiment, the detectable moiety introduced to the sample through the binding of the slow off-rate aptamer may be a fluorescent, chemiluminescent, or colorimetric detectable moiety that is directly attached to the slow off-rate aptamer. When more than one slow off-rate aptamer is used in the buffered slow off-rate aptamer solution, each slow off-rate aptamer may include a detectable moiety with an unique wavelength of detection and/or excitation. Thus multiple targets may be detected simultaneously. Optionally these slow off-rate aptamers may be designed to crosslink to their specific target.

In other embodiments, the targets may be detected sequentially. In this embodiment, once the morphological evaluation with a traditional stain is complete, the sample may be reacted with a first slow off-rate aptamer to a specific first target and the first detectable moiety may be introduced by the presence of the first slow off-rate aptamer if the specific first target is present in the sample. Then the sample may be treated with conditions of heat, buffer, pH, ionic strength sufficient to cause the first slow off-rate aptamer/first target pair to dissociate. The first slow off-rate aptamer may then be washed from the sample and a second slow off-rate aptamer specific to a second target reacted with the sample. The second detectable moiety may then be detected if the second target is present in the sample. This cycle may be completed until the all desired targets have been evaluated.

In another embodiment, the slow off-rate aptamer or slow off-rate aptamers may be designed with an element to support signal generation. In one embodiment, the element to support signal generation may be an enzyme attached to the slow off-rate aptamer, or attached via a tag, such that it does not interfere with binding of the slow off-rate aptamer to the target. Once the slow off-rate aptamer has bound to the specific target and excess slow off-rate aptamer, or slow off-rate aptamers, has been removed, the enzyme may be reacted with its specific substrate to produce a detectable signal at the site where the enzyme may be immobilized. A precipitating, colorimetric or fluorescent substrate may be used. In another embodiment, the enzyme attached to the slow off-rate aptamer may be used to increase the signal. In another embodiment, the element to support signal generation consists of two components. The first component of the element to support signal generation is designed into the slow off-rate aptamer and is ligand like biotin that reacts with a corresponding receptor like avidin, the second component of the element to support signal generation. The second component may be attached to the detectable moiety.

In another embodiment, the slow off-rate aptamer reacted with a specific target in the sample may be used in combination or serve as the nucleic acid target in a variety of nucleic acid amplification methods including PCR, rolling circle amplification, q-beta replicase, strand displacement, helicase dependent amplification, loop mediated isothermal amplification, ligase chain reaction, restriction and circularization aided rolling circle amplification, etc. For example, the target immobilized slow off-rate aptamer may serve as a template for a PCR reaction to produce multiple copies of a PCR product in a solution covering the sample. Detection of the PCR product could be completed a wide variety of methods by hybridization of a labeled PCR product to an array, by real time PCR measurement, by gel electrophoresis, sequencing methods, etc.

In another embodiment, the tissue or cell sample is reacted with one or more slow off-rate aptamers prior to any morphological staining procedure.

One embodiment for the use of slow off-rate aptamers in a cytological evaluation would be the combination of a PAP smear evaluation with slow off-rate aptamers specific to molecular targets from the high risk HPV16 and/or 18 strains. In this case the slow off-rate aptamers may be designed to react with E6 or E7 proteins or to E6 or E7 and one of L1 or E2 or L2 proteins. A representative PAP smear staining protocol utilizes a combination of dyes, Harris hematoxylin, orange G6, and EA 50. EA 50 is a combination dye that contains eosin Y, Bismarck brown, and fast green. Hematoxylin stains nuclei blue, the other dyes react with keratin to stain the cell cytoplasm from green to blue or pink depending on the keratin content. The staining protocol may be started with the hematoxylin (5 minutes). Each staining step may be followed with a number of washes (for example 3) before the next step. Washing cycles may be eliminated after the alcohol treatment step. The slide may then be treated with 0.1% HCl solution for 1 minute, then with 0.02% ammonium water for 1 minute, 95% reagent grade ethanol for 2 minutes for 2 cycles, Orange G6 for 2 minutes, 95% reagent grade ethanol for 2 minutes and 2 cycles, EA 50 for 3 minutes, and finally 95% reagent grade ethanol for 2 minutes and 2 cycles. The slides may be dehydrated with alcohol and cleared with xylene and then a mounting medium applied and a coverslip may be applied. Slides may then be examined microscopically. The coverslip may then be removed and the slide may be treated with one or more rinses of acid alcohol to remove the dyes used for the morphological examination. Once the smear is destained, the slide could be covered with a reaction solution containing the slow off-rate aptamer (or slow off-rate aptamers) and incubated from 30 minutes to overnight. The incubation period should be selected to optimize slow off-rate aptamer association with its specific target while minimizing background staining.

A reaction or buffered solution could independently contain 0.005-40 nM of one or more slow off-rate aptamers each specific to a target of interest. For example, the slow off-rate aptamer concentration could be ≤ any of the following concentrations; 0.005 nM, 1 nM, 2 nM, 4 nM, 8 nM, 16 nM, 32 nM, 35 nM, or 40 nM by slow off-rate aptamer in the mix. The reaction solution could contain a buffer such SB17 (40 mM HEPES, pH 7.5, 125 mM NaCl, 5 mM KCl, 5 mM $MgCl_2$, 1 mM EDTA, 0.05% TWEEN-20) or other buffer selected empirically to minimize the changes in cells or tissues or promote slow off-rate aptamer diffusion into the section (tissue or cell). The reaction solution may further contain materials to minimize non-specific binding of the slow off-rate aptamer to sample derived nucleic acids including for example herring sperm DNA, etc. Additional components could include dextran sulfate, a carrier protein like casein, etc. An optional kinetic challenge step could be utilized.

In one embodiment, tissue sections or cells from a number of related tumor types may be used to select and produce slow off-rate aptamers that react with a desired tumor marker. Because the marker in the different tissue sections may be crosslinked or associated with different materials in the different tissue sections it may be possible to select and produce slow off-rate aptamers that differentiate the presence of that particular marker in the specific, localized environment that is unique to that tumor type. Thus it may be possible to identify a panel of slow off-rate aptamers that can be used to differentiate, for example, anaplastic oligodendrogliom, astrocytomas, and oligoastrocytomas. Optionally these slow off-rate aptamers may be photoaptamers or crosslinking aptamers.

In another embodiment, the slow off-rate aptamers selected and produced to differentiate tumor types, may be produced such that each slow off-rate aptamer in a reaction mixture contains an unique fluorescent or other type of label that would produce a specific signal unique to that slow off-rate aptamer. Detection of an unique combination of labels would be used to provide the differentiation of the type of tumor. Each slow off-rate aptamer could also be produced with multiple copies of the fluorescent or other label to increase signal generated upon interaction of the slow off-rate aptamer and its specific target in a tissue section or cell preparation. Signal generating labels may be selected to be clearly visible in stained cells or tissues eliminating the need to destain the sample before reaction with the slow off-rate aptamer or slow off-rate aptamers. Optionally these slow off-rate aptamers may be photoaptamers or crosslinking aptamers.

In another embodiment, the tissue section or cells may be reacted with slow off-rate aptamers selected and produced to a specific tumor marker. In addition to the slow off-rate aptamer or slow off-rate aptamers to the tumor marker, the tissue section or cells may be reacted with one or more slow off-rate aptamers that are specific to one or more hormone or other type of tumor specific marker that may be produced by the tumor and help identify the tumor type and origin.

In another embodiment, the tissue section or cells may be reacted with one or more slow off-rate aptamer selected and produced to one or more marker that may be used to establish the prognosis for the disease. In one embodiment, the tissue section or cells may be reacted with one or more slow off-rate aptamer selected and produced to one or more marker that may be used to support selection of appropriate therapeutic agents. For example, the presence of a high level of a specific glycosyl hydrolase, YKL-40, in a glioma may indicate a poorer prognosis than in a glioma that has less YKL-40. Differential expression of the YKL-40 level may be established by the level of slow off-rate aptamer staining observed in the tissue section or cell preparation relative to a control material.

In any of the embodiments for the analysis of a tissue or cell sample, after initial incubation of the one or more slow off-rate aptamers with the sample, the slow off-rate aptamer or slow off-rate aptamers may be optionally crosslinked to their corresponding targets by exposure to the appropriate crosslinking activator.

In another embodiment, a histological or cytological reagent is provided that may consist of one or more slow off-rate aptamers specific to one or more targets that are indicative of a specific disease state. Targets may include tumor specific markers, hormones, or other molecules. In addition to the slow off-rate aptamers, the reagent may consist of buffers, salts, detergents, blocking reagents, competitors, and stabilizers.

Another aspect of the present disclosure relates to kits useful for conveniently performing any of the methods disclosed herein to analyze test samples. To enhance the versatility of the disclosed methods, the reagents can be provided in packaged combination, in the same or separate containers, so that the ratio of the reagents provides for substantial optimization of the method and assay. The reagents may each be in separate containers or various reagents can be combined in one or more containers depending upon the cross-reactivity and stability of the reagents.

A kit comprises, in packaged combination, at least one aptamer and at least one competitor to reduce non-specific binding. The kit may also include washing solutions such as buffered aqueous medium for sample dilution as well as slide washing, sample preparation reagents, and so forth. In addition the kit may contain reagents suitable for performing the desired kinetic challenge during the analytical method. The relative amounts of the various reagents in the kits can be varied widely to provide for concentrations of the reagents that substantially optimize the reactions that need to occur during the assay and to further substantially optimize the sensitivity of the assay. Under appropriate circumstances, one or more of the reagents in the kit can be provided as a dry powder, usually lyophilized, including excipients, which upon dissolution will provide a reagent solution having the appropriate concentrations for performing a method or assay in accordance with the present disclosure. The kit can further include a written description of a method in accordance with any of the methods as described herein.

In one embodiment, a kit for the detection and/or quantification of one or more targets that may be present in a test sample includes at least one aptamer having specific affinity for a target, and at least one polyanionic competitor to reduce non-specific binding.

In another embodiment, a kit for the detection and/or quantification of one or more targets that may be present in a test sample includes at least one aptamer having specific affinity for a target that has a covalently attached a detection moiety/label, and at least one polyanionic competitor to reduce non-specific binding.

In another embodiment, a kit for the detection and/or quantification of one or more targets that may be present in a test sample includes at least one aptamer having specific affinity for a target and a covalent moiety that can be stained by a secondary staining reagent, and at least one polyanionic competitor to reduce non-specific binding.

In addition, any of the above-described kits may contain reagents and materials for the performance of a kinetic challenge during the detection method of the kit.

The method of the instant disclosure is illustrated generally in Examples 1-11. Example 1 describes the general affinity SELEX method using a candidate mixture comprised of modified nucleotides. Example 2 describes a photo SELEX method using a candidate mixture comprised of modified nucleotides and a 5'-terminal photoreactive group, and the improved SELEX method in which dilution is used to provide the slow off-rate enrichment process to the equilibrated aptamer:target mixture. Example 3 extends the method described in Example 2 by the addition of a competitor to the dilution step. Example 4 illustrates the effectiveness of the slow off-rate enrichment process. The average dissociation half-life value ($t_{1/2}$) for aptamers using the modified nucleotides 5-(N-benzylcarboxyamide)-dUTP (BndUTP), 5-(N-isobutylcarboxyamide)-dUTP (iBudUTP), or 5-(N-tryptaminocarboxyamide)-dUTP (TrpdUTP) selected in the absence of a slow off-rate enrichment process was 20 minutes with some aptamers having a $t_{1/2}$ value of up to one hour. This is substantially longer than what has been previously described with natural bases or other modified nucleotides. The average for aptamers selected with a slow off-rate enrichment process was over 85 minutes. More specifically, with reference to FIG. 4B, it can be seen that introduction of a slow off-rate enrichment process produced aptamers with $t_{1/2}$ values of ≥about 15 min., ≥about 30 min., ≥about 60 min., ≥about 90 min., ≥about 120 min., ≥about 150 min., ≥about 180 min., ≥about 210 min., and ≥about 240 min. These dissociation rates for aptamer:target complexes are unprecedented.

Example 5 describes the generation of slow off-rate aptamers using a NapdU (5-(N-naphthylmethylcarboxyamide)-dU) candidate mixture.

Example 6 describes the generation of a slow off-rate aptamer to a peptide target.

Example 7 illustrates the utility of slow off-rate aptamers relative to conventional aptamers.

Example 8 illustrates the generation of slow off-rate aptamers using a BndU candidate mixture.

Example 9 describes the generation and histological applications of slow off-rate BndU aptamers to Her2 (ErbB-2).

Example 10 describes the generation and histological applications of slow off-rate BndU aptamers to epidermal growth factor receptor (EGFR/ErbB-1).

Example 11 describes the generation and histological applications of slow off-rate BndU aptamers to Prostate Specific Antigen (PSA).

EXAMPLES

The following examples are provided for illustrative purposes only and are not intended to limit the scope of the invention as defined in the appended claims.

Example 1

Incorporation of Modified Nucleotides in Nucleic Acid Libraries Leads to Higher Affinity Enriched Libraries in Affinity SELEX A. Preparation of Candidate Mixtures Candidate mixtures were prepared with dATP, dGTP, 5-methyl-dCTP (MedCTP) and either dTTP or one of three dUTP analogs: 5-(N-benzylcarboxyamide)-dUTP (BndUTP), 5-(N-isobutylcarboxyamide)-dUTP (iBudUTP), or 5-(N-tryptaminocarboxyamide)-dUTP (TrpdUTP). Candidate mixtures were prepared by polymerase extension of a primer annealed to a biotinylated template (FIG. 3). For each candidate mixture composition, 4.8 nmol forward PCR primer and 4 nmol template were combined in 100 μL 1×KOD DNA Polymerase Buffer (Novagen), heated to 95° C. for 8 minutes, and cooled on ice. Each 100 μL primer:template mixture was added to a 400 μL extension reaction containing 1×KOD DNA Polymerase Buffer, 0.125 U/μL KOD XL DNA Polymerase, and 0.5 mM each dATP, MedCTP, dGTP, and dTTP or dUTP analog, and incubated at 70° C. for 30 minutes. Double-stranded product was captured via the template strand biotins by adding 1 mL streptavidin-coated magnetic beads (MagnaBind Streptavidin, Pierce, 5 mg/mL in 1M NaCl+0.05% TWEEN-20) and incubating at 25° C. for 10 minutes with mixing. Beads were washed three times with 0.75 mL SB1T Buffer (40 mM HEPES, pH 7.5, 125 mM NaCl, 5 mM KCl, 1 mM $MgCl_2$, 1 mM $CaCl_2$, 0.05% TWEEN-20). The aptamer strand was eluted from the beads with 1.2 mL 20 mM NaOH, neutralized with 0.3 mL 80 mM HCl and buffered with 15 μL 1 M HEPES, pH 7.5. Candidate mixtures were concentrated with a Centricon-30 to approximately 0.2 mL, and quantified by UV absorbance spectroscopy.

B. Immobilization of Target Proteins

Target proteins were purchased with poly His tags, such as, $(His)_6$ tags (R&D Systems) and immobilized on $Co^{+2}$-NTA paramagnetic beads (MyOne TALON, Invitrogen, or hereinafter referred to as Talon beads). Target proteins were diluted to 0.2 mg/mL in 0.5 mL B/W Buffer (50 mM Na-phosphate, pH 8.0, 300 mM NaCl, 0.01% TWEEN-20), and added to 0.5 mL TALON beads (pre-washed three times with B/W Buffer and resuspended to 10 mg/mL in B/W Buffer). The mixture was rotated for 30 minutes at 25° C. and stored at 4° C. until use. TALON beads coated with $(His)_6$ peptide were also prepared and stored as above. Prior to use, beads were washed 3 times with B/W Buffer, once with SB1T, and resuspended in SB1T.

C. Aptamer Selection Scheme

Affinity selections were performed separately with each candidate mixture, comparing binding between target protein beads (signal, S) and $(His)_6$ beads (background, B). For each sample, a 0.5 μM candidate DNA mixture was prepared in 40 μL SB1T. 1 μL $(His)_6$-complement oligo (1 mM) (FIG. 3) was added to the DNA, along with 10 μL of a protein competitor mixture (0.1% HSA, 10 μM casein, and 10 μM prothrombin in SB1T).

Binding reactions were performed by adding 50 μL target protein-coated beads or $(His)_6$-coated beads (5 mg/mL in SB1T) to the DNA mixture and incubating 37° C. for 15 minutes with mixing. The DNA solution was removed and the beads were washed 5 times at 37° C. with SB1T containing 0.1 mg/mL herring sperm DNA (Sigma-Aldrich). Unless indicated, all washes were performed by re-suspending the beads in 100 μL wash solution, mixing for 30 seconds, separating the beads with a magnet, and removing the wash solution. Bound aptamers were eluted from the beads by adding 100 μL SB1T+2 M Guanidine-HCl and incubating at 37° C. for 5 minutes with mixing. The aptamer eluate was transferred to a new tube after magnetic separation. After the first two selection rounds, the final two of five target beads washes were done for 5 minutes instead of 30 seconds.

Primer beads were prepared by immobilizing biotinylated reverse PCR primer to streptavidin-coated paramagnetic beads (MyOne-Streptavidin C1 (SA beads), Invitrogen). 5 mL SA beads (10 mg/mL) were washed once with NaClT (5 M NaCl, 0.01% TWEEN-20), and resuspended in 5 mL biotinylated reverse PCR primer (5 μM in NaClT). The sample was incubated at 25° C. for 15 minutes, washed twice with 5 mL NaClT, resuspended in 12.5 mL NaClT (4 mg/mL), and stored at 4° C.

25 μL primer beads (4 mg/mL in NaClT) were added to the 100 μL aptamer solution in Guanidine Buffer and incubated at 50° C. for 15 minutes with mixing. The aptamer solution was removed, and the beads were washed 5 times with SB1T. Aptamer was eluted from the beads by adding 85 μL 20 mM NaOH, and incubating at 37° C. for 1 minute with mixing. 80 μL aptamer eluate was transferred to a new tube after magnetic separation, neutralized with 20 μL 80 mM HCl and buffered with 1 μL 0.5M Tris-HCl pH 7.5.

D. Aptamer Amplification and Purification

Selected aptamer DNA was amplified and quantified by QPCR. 48 μL DNA was added to 12 μL QPCR Mix (5×KOD DNA Polymerase Buffer, 25 mM $MgCl_2$, 10 μM forward PCR primer, 10 μM biotinylated reverse PCR primer, 5×SYBR Green I, 0.125 U/μL KOD XL DNA Polymerase, and 1 mM each dATP, dCTP, dGTP, and dTTP) and thermal cycled in an ABI5700 QPCR instrument with the following protocol: 1 cycle of 99.9° C., 15 seconds, 55° C., 10 seconds, 70° C., 30 minutes; 30 cycles of 99.9° C., 15 seconds, 72° C., 1 minute. Quantification was done with the instrument software and the number of copies of DNA selected with target beads and $(His)_6$ beads were compared to determine signal/background ratios.

Following amplification, the PCR product was captured on SA beads via the biotinylated antisense strand. 1.25 mL SA beads (10 mg/mL) were washed twice with 0.5 mL 20 mM NaOH, once with 0.5 mL SB1T, resuspended in 2.5 mL 3 M NaCl, and stored at 4° C. 25 μL SA beads (4 mg/mL in 3 M NaCl) were added to 50 μL double-stranded QPCR product and incubated at 25° C. for 5 minutes with mixing. The beads were washed once with SB1T, and the "sense" strand was eluted from the beads by adding 200 μL 20 mM NaOH, and incubating at 37° C. for 1 minute with mixing. The eluted strand was discarded and the beads were washed 3 times with SB1T and once with 16 mM NaCl.

Aptamer sense strand was prepared with the appropriate nucleotide composition by primer extension from the immobilized antisense strand. The beads were resuspended in 20 μL primer extension reaction mix (1× Primer Extension Buffer (120 mM Tris-HCl pH 7.8 @ 20, 10 mM KCl, 7 mM $MgSO_4$, 6 mM $(NH_4)_2SO_4$, 0.001% BSA, and 0.01% Triton X100), 5 μM forward PCR primer, 0.125 U/μL KOD XL DNA Polymerase, 0.5 mM each dATP, MedCTP, dGTP, and either dTTP or dUTP analog) and incubated at 68° C. for 30 minutes with mixing. The beads were washed 3 times with SB1T, and the aptamer strand was eluted from the beads by adding 85 μL 20 mM NaOH, and incubating at 37° C. for 1 minute with mixing. 80 μL aptamer eluate was transferred to a new tube after magnetic separation, neutralized with 20 μL 80 mM HCl and buffered with 5 μL 0.1 M HEPES, pH 7.5.

E. Selection Stringency and Feedback

The relative target protein concentration of the selection step was lowered each round in response to the S/B ratio as follows, where signal S and background B are defined in Section C above:

$$\text{If } S/B<10, [P](i+l)=[P]i$$

$$\text{If } 10\leq S/B<100, [P](i+l)=[P]i/3.2$$

$$\text{If } S/B\geq 100, [P](i+l)=[P]i/10$$

where [P]=protein concentration and i=current round number.

Target protein concentration was lowered by adjusting the mass of target protein beads (and $(His)_6$ beads for background determination) added to the selection step.

After each selection round, the convergence state of the enriched DNA mixture was determined. 5 μL double-stranded QPCR product was diluted to 200 μL with 4 mM $MgCl_2$ containing 1×SYBR Green I. Samples were overlaid with 75 μL silicon oil and analyzed for convergence using a $C_0t$ analysis which measures the hybridization time for complex mixtures of double stranded oligonucleotides. The sample was thermal cycled with the following protocol: 3 cycles of 98° C., 1 minute, 85° C., 1 minute; 1 cycle of 93° C., 1 minute, 85° C., 15 minutes. During the 15 minutes at 85° C., fluorescent images were measured at 5-second intervals. The fluorescence intensity was plotted as a function of log (time) to evaluate the diversity of the sequences.

F. Measurement of Equilibrium Binding Constant (Kd)

Equilibrium binding constants of the enriched libraries were measured using TALON bead partitioning. DNA was renatured by heating to 95° C. and slowly cooling to 37° C. Complexes were formed by mixing a low concentration of radiolabled DNA (~$1\times10^{-11}$ M) with a range of concentrations of target protein ($1\times10^{-7}$ M to $1\times10^{-12}$ M final) in SB1 Buffer, and incubating at 37° C. A portion of each reaction was transferred to a nylon membrane and dried to determine total counts in each reaction. A small amount of 5 mg/mL TALON beads was added to the remainder of each reaction and mixed at 37° C. for one minute. A portion was passed through a MultiScreen HV Plate (Millipore) under vacuum to separate protein-bound complexes from unbound DNA and washed with 100 µL SB1 Buffer. The nylon membranes and MultiScreen HV Plates were phosphorimaged and the amount of radioactivity in each sample quantified using a FUJI FLA-3000. The fraction of captured DNA was plotted as a function of protein concentration and a non-linear curve-fitting algorithm was used to extract equilibrium binding constants ($K_d$ values) from the data. Table 1 shows the $K_d$ values determined for each enriched candidate mixture to a set of targets. NT indicates that the enriched library for a particular base composition did not appear to have changed from the original candidate mixture, as determined by $C_0t$ analysis, and was therefore Not Tested (NT).

Table 1 shows the equilibrium binding constants ($K_d$) for enriched pools to fifteen different protein targets and four different DNA libraries: naturally occurring bases (dT), 5-(N-benzylcarboxyamide) (BndU), 5-(N-isobutylcarboxyamide) (iBudU) or 5-(N-tryptaminocarboxyamide) (TrpdU). The use of modified bases in the SELEX process produces a significantly higher percentage of desirable high affinity aptamers. It was observed that only 2 of the 14 aptamers produced with the normal nucleotides have the desired slow dissociation rates. Slow off-rate aptamers produced with the modified nucleotides were identified 9 of 14, 7 of 14, and 14 of 14 for BndUTP, iBudUTP, and TrpdUTP, respectively.

TABLE 1

Equilibrium binding constants ($K_d$) of the enriched libraries selected with different modified nucleotides, reported in units of molarity.

| Target Protein | dTTP | BndUTP | iBudUTP | TrpdUTP |
|---|---|---|---|---|
| 4-1BB | >$1.0 \times 10^{-7}$ | $5.6. \times 10^{-9}$ | >$1.0. \times 10^{-7}$ | $3.9. \times 10^{-9}$ |
| B7 | >$1.0. \times 10^{-7}$ | $1.1. \times 10^{-8}$ | NT | $7.2. \times 10^{-9}$ |
| B7-2 | >$1.0. \times 10^{-7}$ | NT | >$1.0. \times 10^{-7}$ | $5.7. \times 10^{-9}$ |
| CTLA-4 | >$1.0. \times 10^{-7}$ | NT | NT | $1.4. \times 10^{-9}$ |
| E-Selectin | >$1.0. \times 10^{-7}$ | >$1.0. \times 10^{-7}$ | >$1.0. \times 10^{-7}$ | $1.9. \times 10^{-9}$ |
| Fractalkine | NT | >$1.0. \times 10^{-7}$ | NT | $5.1. \times 10^{-11}$ |
| GA733-1 protein | $8.9. \times 10^{-9}$ | $2.8. \times 10^{-9}$ | $4.7. \times 10^{-9}$ | $4.5. \times 10^{-10}$ |
| Gp130 | >$1.0. \times 10^{-7}$ | $5.9. \times 10^{-9}$ | $2.2. \times 10^{-8}$ | $1.2. \times 10^{-9}$ |
| HMG-1 | >$1.0. \times 10^{-7}$ | NT | $2.2. \times 10^{-8}$ | $4.9. \times 10^{-9}$ |
| IR | >$1.0. \times 10^{-7}$ | $1.9. \times 10^{-9}$ | $1.2. \times 10^{-8}$ | $2.2. \times 10^{-10}$ |
| OPG | $3.7. \times 10^{-8}$ | $4.6. \times 10^{-9}$ | $9.5. \times 10^{-9}$ | $1.7. \times 10^{-10}$ |
| PAI-1 | >$1.0. \times 10^{-7}$ | $3.7. \times 10^{-10}$ | $9.1. \times 10^{-10}$ | $4.3. \times 10^{-10}$ |
| P-Cadherin | >$1.0. \times 10^{-7}$ | $3.5. \times 10^{-9}$ | $5.2. \times 10^{-9}$ | $2.7. \times 10^{-9}$ |
| sLeptin R | >$1.0. \times 10^{-7}$ | $2.3. \times 10^{-9}$ | NT | $4.6. \times 10^{-10}$ |

NT = not tested.

Example 2

Figure 6:
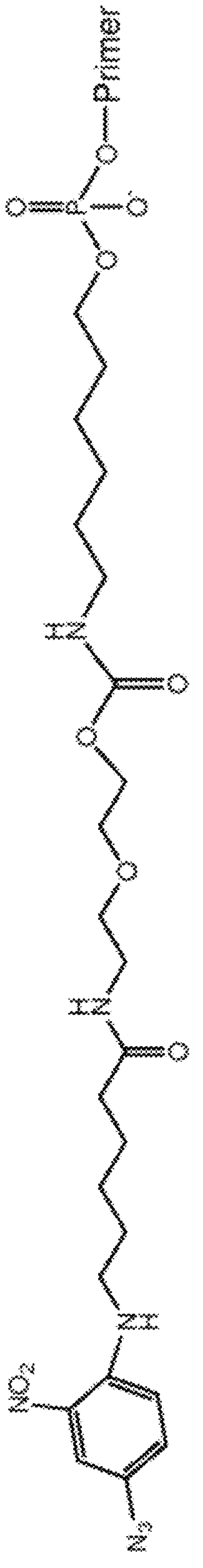
FIG. 6 illustrates the chemical structures of the chromophores coupled to the 5' terminus of the forward primer as illustrated in FIGS. 5A and 5B.

Generation of PhotoAptamers using 5'-Fixed PhotoSELEX and Slow Off-Rate Enrichment Process by Dilution A. Preparation of Candidate Mixtures Candidate mixtures containing dATP, dCTP, dGTP, and BndUTP were prepared by polymerase extension of a primer annealed to a biotinylated template (FIG. 5A-B). For each template, four different forward primers were used, each possessing a unique chromophore at the 5' terminus (see FIG. 6 for the chromophore structures). For each candidate mixture, 11 nmol forward primer (with 5' chromophore) and 10 nmol template were combined in 250 µL Primer Extension Buffer (120 mM Tris-HCl pH 7.8, 10 mM KCl, 6 mM $(NH_4)_2SO_4$, 7 mM $MgSO_4$, 0.1 mg/mL BSA, 0.1% Triton X-100), heated to 95° C. for 5 minutes, and cooled on ice. 125 µL each primer: template mixture was added to a 1 mL extension reaction containing Primer Extension Buffer, 0.125 U/µL KOD XL DNA Polymerase, and 0.5 mM each dATP, dCTP, dGTP, and BndUTP, and incubated at 70° C. for 30 minutes. Each 1 mL reaction was split into four 250 µL aliquots and chilled on ice. Double-stranded product was captured via the template strand biotins by adding 1 mL streptavidin-coated magnetic beads (MagnaBind-Streptavidin, Pierce, 5 mg/mL in 1M NaCl+0.05% TWEEN-20) to each 250 µL aliquot and incubating at 25° C. for 60 minutes with mixing. Beads were washed three times with 0.5 mL SB17T Buffer (40 mM HEPES, pH 7.5, 125 mM NaCl, 5 mM KCl, 5 mM $MgCl_2$, 1 mM EDTA, 0.05% TWEEN-20). The aptamer strand was eluted from the beads with 1 mL 20 mM NaOH, neutralized with 0.25 mL 80 mM HCl and buffered with 10 µL 1 M HEPES, pH 7.5. Candidate mixtures were concentrated with a Centricon-30 to approximately 0.2 mL, and quantified by UV absorbance spectroscopy.

B. Preparation of Target Proteins

Untagged target proteins were biotinylated by covalent coupling of NHS-PEO4-biotin (Pierce) to lysines residues. Proteins (300 pmol in 50 µL) were exchanged into SB17T with a Sephadex G-25 microspin column. NHS-PEO4-biotin was added to 1.5 mM and the reaction was incubated at 4° C. for 16 hours. Unreacted NHS-PEO4-biotin was removed with a Sephadex G-25 microspin column.

C. Aptamer Selection with Slow Off-Rate Enrichment Process and Photocros Slinking Selections were performed separately with each candidate mixture, comparing binding between samples with target protein (signal S) and samples without target protein (background B). The first three rounds were performed with selection for affinity (no photocrosslinking); the second and third included slow off-rate enrichment process. Rounds four through eight included both slow off-rate enrichment process and photocrosslinking.

For each sample, a 90 µL DNA mixture was prepared in SB17T with 10-20 pmoles candidate mixture (100 pmoles in the first round) and 100 pmoles reverse primer. Samples were heated to 95° C. for 3 minutes and cooled to 37° C. at a rate of 0.1 C/second. Samples were combined with 10 µL protein competitor mixture (0.1% HSA, 10 µM casein, and 10 µM prothrombin in SB17T), added to 0.5 mg SA beads (prewashed twice with 20 mM NaOH and once with SB17T), and incubated at 37° C. for 5 minutes with mixing. Beads were removed by magnetic separation.

Binding reactions were performed by adding 10 µL target protein (0.5 µM in SB17T) or SB17T to 40 µL DNA mixture and incubating at 37° C. for 30 minutes.

When slow off-rate enrichment process was employed, samples were diluted 20× by adding 950 μL SB17T (pre-heated to 37° C.), and incubated at 37° C. for 30 minutes prior to capturing complexes.

Complexes were captured on SA beads via protein biotins by adding 0.25 mg MyOne-SA beads (Invitrogen) and incubating at 37° C. for 15 minutes with mixing. Free DNA was removed by washing the beads five times with SB17T. Unless indicated, all washes were performed by resuspending the beads in 100 μL wash solution, mixing for 30 seconds at 25° C., separating the beads with a magnet, and removing the wash solution. The aptamer strand was eluted from the beads by adding 85 μL 20 mM NaOH, and incubating at 37° C. for 1 minute with mixing. 80 μL aptamer eluate was transferred to a new tube after magnetic separation, neutralized with 20 μL 80 mM HCl, and buffered with 1 μL 0.5 M Tris-HCl, pH 7.5.

When photo-selection was employed, the 50 μL binding reactions, (or 1 mL binding reactions after optional slow off-rate enrichment process by dilution) were irradiated from above with a high-pressure mercury lamp (Optical Associates, Inc. model 0131-0003-01, 500 W, with 310 nm mirror set). Candidate mixtures possessing a BrdU chromophore were irradiated for 37 seconds, those possessing an ANA chromophore were irradiated for 60 seconds, and those possessing an AQ or psoralen chromophore were irradiated for 10 minutes. An additional filter (5 mm plate glass) was used for the ANA, AQ and psoralen chromophores to eliminate unnecessary, but potentially damaging wavelengths below 320 nm. Complexes were captured as above, and non-crosslinked DNA was removed by washing the beads once with 4 M guanidine-HCl+0.05% TWEEN-20 at 50° C. for 10 minutes, once with 20 mM NaOH at 25° C. for 2 minutes, twice with SB17T, and once with 16 mM NaCl. Crosslinked DNA was not removed from the bead surface for the amplification steps.

D. Aptamer Amplification and Purification

Selected aptamer DNA was amplified and quantified by QPCR. 48 μL DNA was added to 12 μL QPCR Mix (5×KOD DNA Polymerase Buffer, 25 mM MgCl2, 10 μM forward PCR primer, 10 μM biotinylated reverse PCR primer, 5×SYBR Green I, 0.125 U/μL KOD XL DNA Polymerase, and 1 mM each dATP, dCTP, dGTP, and dTTP) and thermal cycled in an a Bio-Rad MyIQ QPCR instrument with the following protocol: 1 cycle of 99.9° C., 15 sec, 55° C., 10 sec, 68° C., 30 min, 30 cycles of 99.9° C., 15 seconds, 72° C., 1 minute. Quantification was done with the instrument software and the number of copies of DNA selected with and without target protein were compared to determine signal/background ratios.

When photo-selection was employed, a cDNA copy of the selected DNA was prepared by primer extension on the bead surface. Washed beads were resuspended in 20 μL cDNA extension mix (Primer Extension Buffer containing 5 μM reverse PCR primer, 0.5 mM each dATP, dCTP, dGTP, and dTTP, and 0.125 U/μL KOD XL DNA Polymerase) and incubated at 68° C. for 30 minutes with mixing. The beads were washed 3 times with SB17T, and the aptamer strand was eluted by from the beads by adding 85 μL 20 mM NaOH, and incubating at 37° C. for 1 minute with mixing. 80 μL aptamer eluate was transferred to a new tube after magnetic separation, neutralized with 20 μL 80 mM HCl and buffered with 1 μL 0.5 M Tris-HCl pH 7.5. The cDNA was amplified and quantified by QPCR as above for the 30 cycles of 99.9° C., 15 seconds, 72° C., 1 minute.

Following amplification, the PCR product was captured on SA beads via the biotinylated antisense strand. 1.25 mL SA beads (10 mg/mL) were washed twice with 0.5 mL 20 mM NaOH, once with 0.5 mL SB17T, resuspended in 1.25 mL 3 M NaCl+0.05% Tween, and stored at 4° C. 25 μL SA beads (10 mg/mL in 3 M NaClT) were added to 50 μL double-stranded QPCR product and incubated at 25° C. for 5 minutes with mixing. The beads were washed once with SB17T, and the "sense" strand was eluted from the beads by adding 200 μL 20 mM NaOH, and incubating at 37° C. for 1 minute with mixing. The eluted strand was discarded and the beads were washed 3 times with SB17T and once with 16 mM NaCl.

Aptamer sense strand was prepared with the appropriate chromophore by primer extension from the immobilized antisense strand. The beads were resuspended in 20 μL primer extension reaction mixture (1× Primer Extension Buffer, 1.5 mM MgCl2, 5 μM forward primer with appropriate 5' chromophore, 0.5 mM each dATP, dCTP, dGTP, and BndUTP, and 0.125 U/μL KOD XL DNA Polymerase) and incubated at 68° C. for 30 minutes with mixing. The beads were washed 3 times with SB17T, and the aptamer strand was eluted from the beads by adding 85 μL 20 mM NaOH, and incubating at 37° C. for 1 minute with mixing. 80 μL aptamer eluate was transferred to a new tube after magnetic separation, neutralized with 20 μL 80 mM HCl and buffered with 5 μL 0.1 M HEPES, pH 7.5.

E. Selection Stringency and Feedback

Target protein was adjusted at each round as described in Example 1. After each round of selection, the convergence state of the enriched pool was determined as described in Example 1.

F. Equilibrium Binding Constants of Enriched Libraries

The binding affinity was determined as described in Example 1 above, but with SA capture beads. The following table, Table 2, summarizes the equilibrium binding constants (Kd) obtained using the photoSELEX protocol with slow off-rate enrichment process.

TABLE 2

Equilibrium binding constants ($K_d$) of the enriched libraries selected with different chromophores, reported in units of molarity. Measurements were not made on libraries that failed to converge (indicated with an x).

| Target Protein | BrdU | AQ | ANA | Psor |
|---|---|---|---|---|
| β-catenin | $2.7. \times 10^{-8}$ | $3.6. \times 10^{-9}$ | $1.1. \times 10^{-9}$ | $1.6. \times 10^{-9}$ |
| bFGF | $3.1. \times 10^{-8}$ | $5.7. \times 10^{-10}$ | $7.1. \times 10^{-10}$ | $5.1. \times 10^{-10}$ |
| CMP-SAS | x | $6.2. \times 10^{-9}$ | $7.3. \times 10^{-9}$ | $4.9. \times 10^{-8}$ |
| endostatin | $1.3. \times 10^{-9}$ | $8.7. \times 10^{-10}$ | $8.8. \times 10^{-10}$ | $1.3. \times 10^{-9}$ |
| IL-6 | $1.0. \times 10^{-9}$ | $5.4. \times 10^{-10}$ | $4.0. \times 10^{-10}$ | x |
| myelo-peroxidase | $6.0. \times 10^{-10}$ | $2.8. \times 10^{-10}$ | $5.0. \times 10^{-10}$ | $1.5. \times 10^{-10}$ |
| SDF-1β | $8.1. \times 10^{-10}$ | $5.7. \times 10^{-10}$ | $3.8. \times 10^{-10}$ | x |
| TIMP-1 | $5.2. \times 10^{-9}$ | $7.3. \times 10^{-9}$ | $8.9. \times 10^{-9}$ | x |
| VEGF | $7.2. \times 10^{-10}$ | $4.2. \times 10^{-9}$ | $5.5. \times 10^{-10}$ | x |
| vWF | $2.6. \times 10^{-8}$ | $8.8. \times 10^{-9}$ | $8.1. \times 10^{-9}$ | x |

G. Crosslink Activity Assay

The crosslink yield of enriched libraries was determined by measuring the percent of DNA crosslinked to protein under conditions of saturating protein and light. Radiolabeled DNA (50 pM) was mixed with reverse primer (16 nM) in SB17T, heated to 95° C. for 3 minutes, and cooled to 37° C. at 0.1° C./second. Target protein was added to the DNA mix to a final concentration of 10 nM and incubated at 37° C. for 30 minutes. Control samples with no protein were simultaneously prepared. Samples were crosslinked with the chromophore-specific conditions described above, but with a saturating dose (6 minutes for BrdU, 10 minutes for ANA, and 30 minutes for AQ and Psor). Samples were analyzed by denaturing PAGE, FIG. 7, and quantified and the results are tabulated in Table 3.

TABLE 3

Crosslink yields of the enriched libraries selected with different chromophores, reported in units of percent of total DNA crosslinked to protein. Measurements were not made on libraries that failed to converge (indicated with an x).

| Target Protein | BrdU | AQ | ANA | Psor |
|---|---|---|---|---|
| β-catenin | 15 | 9 | 8 | 1 |
| bFGF | 4 | 9 | 15 | 4 |
| CMP-SAS | x | 3 | 5 | 2 |
| Endostatin | 2 | 1 | 18 | 3 |
| IL-6 | 0 | 5 | 9 | |
| Myeloperoxidase | 4 | 13 | 9 | 8 |
| SDF-1β | 8 | 10 | 17 | x |
| TIMP-1 | 1 | 4 | 2 | x |
| VEGF | 1 | 1 | 4 | x |
| vWF | 2 | 2 | 7 | x |

Example 3

Generation of Slow off-Rate Aptamers Using a Slow off-Rate Enrichment Process with a Competitor A. Preparation of Candidate Mixtures Candidate mixtures containing dATP, dCTP, dGTP, and BndUTP were prepared by polymerase extension of a primer annealed to a biotinylated template for 94 protein targets. 55 nmol forward primer (with 5' ANA chromophore) and 55 nmol template were combined in 0.5 mL Primer Extension Buffer (120 mM Tris-HCl pH 7.8, 10 mM KCl, 6 mM $(NH_4)_2SO_4$, 7 mM $MgSO_4$, 0.1 mg/mL BSA, 0.1% Triton X-100), heated to 95° C. for 5 minutes, 70° C. for 5 minutes, 48° C. for 5 minutes, and cooled on ice. The primer:template mixture was added to a 5.5 mL extension reaction containing Primer Extension Buffer, 0.125 U/μL KOD XL DNA Polymerase, and 0.5 mM each dATP, dCTP, dGTP, and BndUTP, and incubated at 70° C. for 60 minutes. After completion of the extension reaction, the solution was chilled on ice. Double-stranded product was captured via the template strand biotins by adding 25 mL streptavidin-coated magnetic beads (MagnaBind-Streptavidin, Pierce, 5 mg/mL in 1 M NaCl+0.05% TWEEN-20) to the primer extension product and incubating 25° C. for 15 minutes with rotating. Beads were washed three times with 40 mL SB17T Buffer (40 mM HEPES, pH 7.5, 125 mM NaCl, 5 mM KCl, 5 mM $MgCl_2$, 1 mM EDTA, 0.05% TWEEN-20). The aptamer strand was eluted from the beads with 35.2 mL 20 mM NaOH for 5 minutes with shaking. The eluted strand was neutralized with 8.8 mL 80 mM HCl and buffered with 400 μL 1 M HEPES, pH 7.3. Candidate mixtures were concentrated with a Centricon-30 to approximately 0.7 mL, and quantified by UV absorbance spectroscopy.

B. Preparation of Target Proteins

Untagged target proteins were biotinylated as described in Example 2.

C. Aptamer Selection with Slow Off-Rate Enrichment Process and Photocros Slinking Selections were performed separately as described in Example 2, with the addition of 10 mM dextran sulfate as a competitor for aptamer rebinding during the slow off-rate enrichment process in rounds six through nine.

The slow off-rate enrichment process was employed in three different ways. In rounds two and three, samples were diluted 20× by adding 950 μL SB17T (preheated to 37° C.), and incubated at 37° C. for 30 minutes prior to capturing complexes. In rounds four and five, samples were diluted 20× by adding 950 μL SB17T (preheated to 37° C.), and incubated at 37° C. for 30 minutes prior to crosslinking. In rounds six and seven, samples were diluted 20× by adding 950 μL SB17T (preheated to 37° C.). 50 μL of each diluted sample was diluted again by transferring to 950 μL SB17T+10 mM 5000K dextran sulfate (preheated to 37° C.) to give an overall 400× dilution, and incubated at 37° C. for 60 minutes prior to crosslinking. In rounds eight and nine, samples were diluted 20× by adding 950 μL SB17T (preheated to 37° C.), and 50 μL of each sample was diluted again by transferring to 950 μL SB17T (preheated to 37° C.) to give 400× dilution. Finally, 50 μL of each 400× diluted sample was diluted again by transferring to 950 μL SB17T+10 mM 5000K dextran sulfate (preheated to 37° C.) to give an overall 8000× dilution, and incubated at 37° C. for 60 minutes prior to crosslinking. Complexes were captured and washed as described in Example 2. When photo-crosslinking was employed, the 1 mL binding reactions after the slow off-rate enrichment process were irradiated from above with an array of 470 nm LEDs for 60 seconds prior to complex capture as in Example 2.

D. Aptamer Amplification and Purification

Amplification and purification were performed as in Example 2.

E. Selection Stringency and Feedback

Target protein was adjusted at each round as described in Example 1, except in rounds six and eight. In order to maximize signal after these large dilutions, the target protein was increased to 100 nM for rounds six and eight. After each round of selection, the convergence state of the enriched pool was determined as described in Example 1.

F. Dissociation Rate Constant Determination Protocol.

The rate constant for aptamer:protein complex dissociation (koff) was determined for each aptamer by measuring the fraction of pre-formed aptamer:protein complexes that remain bound after dilution as a function of time. Radiolabeled aptamer (50 pM) was equilibrated in SB17T-0.002 (SB17T with TWEEN-20 reduced to 0.002%) at 37° C. with protein at a concentration 10× greater than the measured $K_d$ value. Samples were diluted 100× with SB17T-0.002 at 37° C. and aliquots were removed at various time points and partitioned to separate free aptamer from protein:aptamer complexes. Partitioning was accomplished by adding ZORBAX resin (Agilent) to the sample, capturing complexes on the resin, passing the sample through a DuraPore membrane under vacuum, and washing the resin with SB17T-0.002. For proteins not efficiently captured with ZORBAX resin, the assay was performed with biotinylated protein in SB17T and partitioning was accomplished by capturing complexes with SA beads. The amount of complex remaining at each time point was determined by quantifying the radiolabeled aptamer on the resin with a FUJI FLA-3000 phosphorimager. The fraction of complex was plotted as a function of time and the dissociation rate constant (koff) and dissociation half-life value ($t_{1/2}$) was determined by fitting the data to an analytic expression for bimolecular dissociation kinetics using non-linear regression.

G. Kinetic Properties of some Aptamers

The following table, Table 4, summarizes the dissociation half-life values ($t_{1/2}$) obtained for aptamers selected against 10 targets using this protocol.

TABLE 4

| Dissociation half-life values ($t_{1/2}$) of aptamers using the competitor slow off-rate enrichment step protocol. | |
|---|---|
| Target Protein | $t_{1/2}$ (min) |
| bFGF R | 66 |
| C3 | 164 |
| catalase | 58 |
| FGF-17 | 91 |
| group IB phospholipase A2 | 40 |
| HB-EGF | 49 |
| HCC-4 | 143 |
| IL-6 sR | 114 |
| SAP | 186 |
| uPA | 85 |

Example 4

Figure 4A:
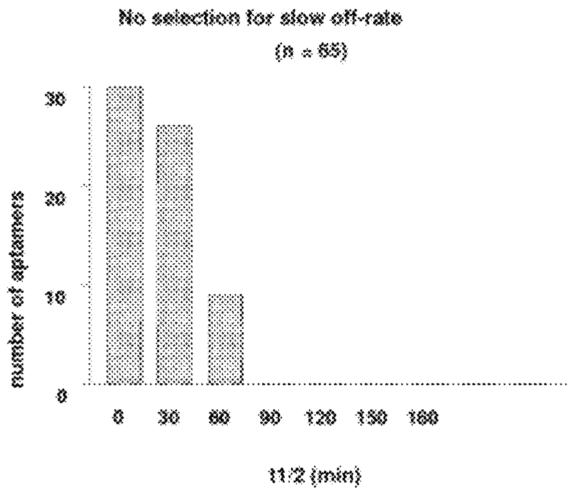
FIG. 4 illustrates histograms of dissociation rate constants for affinity aptamers selected without (FIG. 4A) and with (FIG. 4B) a slow off-rate enrichment process as described in Example 2.
Figure 4B:
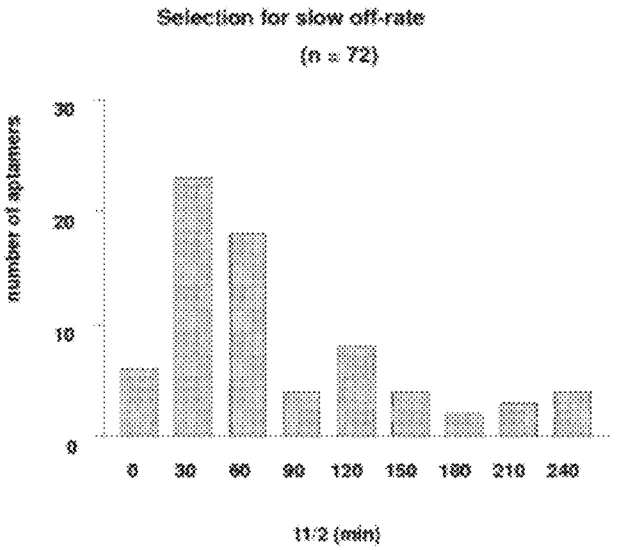

The Slow Off-Rate Enrichment Process Increases the Dissociation Half-Life of Selected Aptamers Dissociation half-life values ($t_{1/2}$) were measured and plotted for 65 aptamers that were selected by either the affinity SELEX method described in Example 1 or photo SELEX methods described in U.S. Pat. No. 6,458,539, entitled "Photoselection of Nucleic Acid Ligands" without a slow off-rate enrichment process (FIG. 4A). $t_{1/2}$ values were also measured and plotted for 72 aptamers that were selected by the slow off-rate enrichment process described in Example 2 with a slow off-rate enrichment process by dilution or dilution with competitor (FIG. 4B). The average $t_{1/2}$ value for aptamers using the modified nucleotides 5-(N-benzylcarboxyamide)-dUTP (BndUTP), 5-(N-isobutylcarboxyamide)-dUTP (iBudUTP), or 5-(N-tryptaminocarboxyamide)-dUTP (Trp-dUTP) selected in the absence of a slow off-rate enrichment process was 20 minutes with some aptamers having a $t_{1/2}$ value of up to one hour. This is substantially longer than what has been previously described with natural bases or other modified nucleotides. The average for aptamers selected with a slow off-rate enrichment process was over 85 minutes, with some aptamers having a $t_{1/2}$ value in excess of four hours.

Example 5

Generation of Aptamers from a NapdU Random Library

A. Preparation of Candidate Mixtures

Candidate mixtures containing dATP, dCTP, dGTP, and NapdU were prepared as described in Example 3 but without the 5'-ANA photoreactive group.

B. Immobilization of Target Proteins

Target proteins contained a $(His)_6$ tag and were captured with Talon beads as described in Example 1.

C. Aptamer Selection with Slow Off-Rate Enrichment Process

Aptamer selection was performed as described in Example 3, but without photocrosslinking.

D. Aptamer Amplification and Purification

Amplification and purification were performed as described in Example 3.

E. Selection Stringency and Feedback

Selection stringency and feedback were performed as described in Example 3.

F. Aptamer Properties

The equilibrium binding constant ($K_d$) of four aptamers from this selection are listed in Table 5.

TABLE 5

| Equilibrium binding constants ($K_d$) of NapdU aptamers | |
|---|---|
| Target Protein | $K_d$ (M) |
| bFGF | $1.1. \times 10^{-9}$ |
| Endostatin | $2.0. \times 10^{-10}$ |
| TIMP-3 | $1.5. \times 10^{-10}$ |
| VEGF | $7.2. \times 10^{-10}$ |

Example 6

Generation of Slow Off-Rate Aptamers for a Peptide Target Using a Slow Off-Rate Enrichment Process with a Competitor A. Preparation of Candidate Mixtures Candidate mixtures containing dATP, dCTP, dGTP, and BndUTP were prepared by polymerase extension of a primer with a 5' ANA chromophore and purified as described in Example 3.

B. Aptamer Selection with Slow Off-Rate Enrichment Process and Photocros Slinking Aptamer selection was performed as described in Example 3 with the 29 amino acid biotinylated target peptide SMAP29 (Sheep Myeloid Antibacterial Peptide MAP-29, Anaspec).

C. Aptamer Amplification and Purification

Amplification and purification were performed as described in Example 3.

D. Selection Stringency and Feedback

Selection stringency and feedback were performed as described in Example 3.

E. Aptamer Properties

Figure 13A:
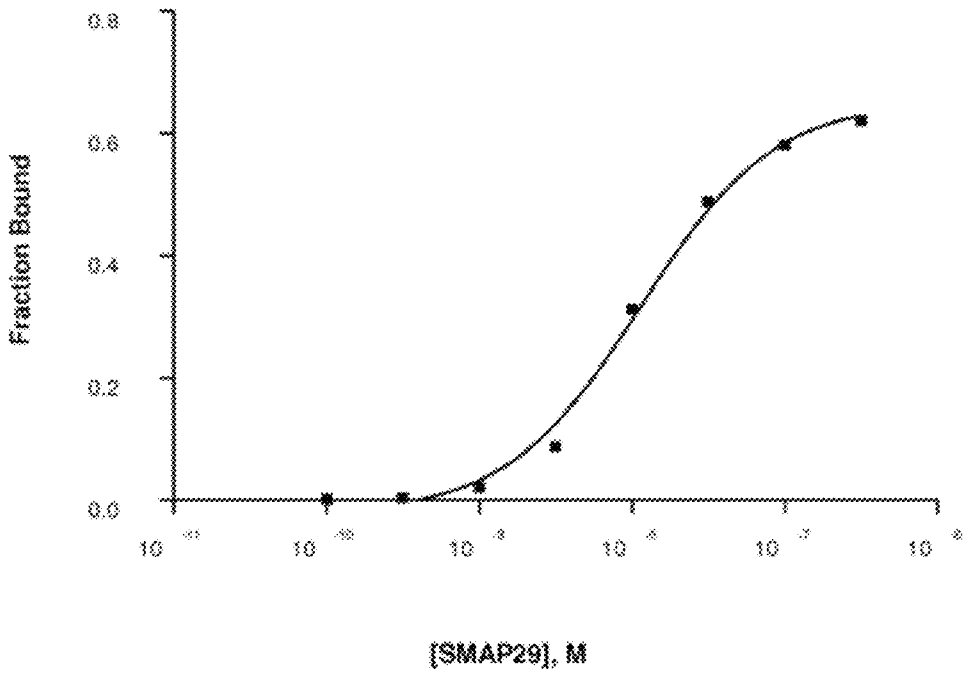
FIGS. 13A and 13B illustrate performance curves for a slow off-rate aptamer where the target was a peptide.
Figure 13B:
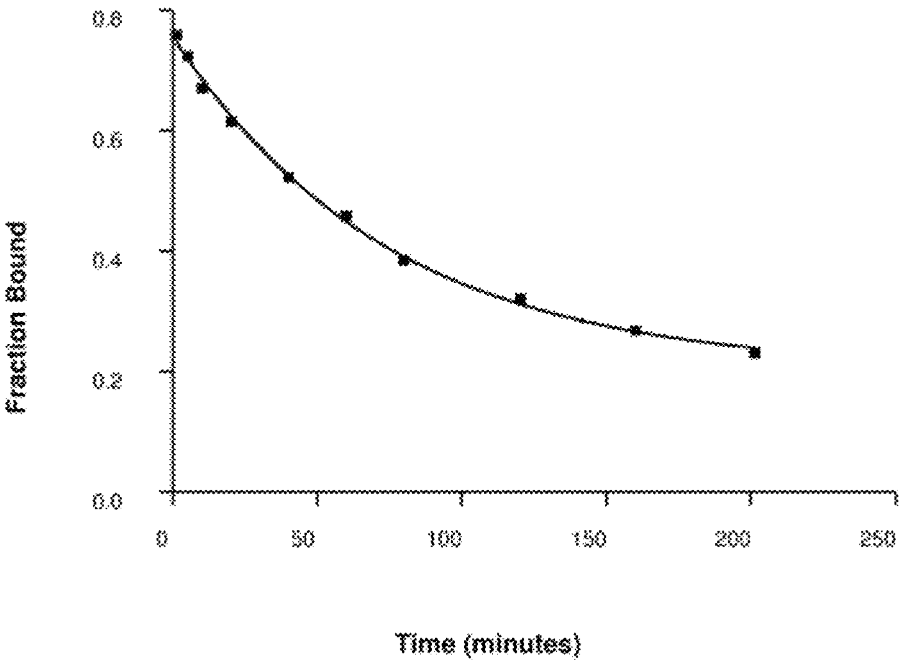

The equilibrium binding constant ($K_d$) of an aptamer from this selection was $1.2.\times10^{-8}$M (measured according to the protocol described in Example 1). The dissociation half-life ($t_{1/2}$) of this aptamer was 69 minutes (measured according to the protocol described in Example 3). Results are shown in FIG. 13A and FIG. 13B.

Example 7

Protein Measurements in Test Samples were Enabled by Aptamers with Slow Off-Rates A. Preparation of Aptamer/Primer Mixtures and Test Samples Aptamers with a biotin Cy3 detection label (4 nM each) were mixed with a 3× excess of capture probe (oligonucleotide complementary to the 3' fixed region of the aptamer containing a biotin tag and photocleavable element) in 1× SB17T and heated at 95° C. for 4 minutes, then 37° C. for 13 minutes, and diluted 1:4 in 1× SB17T. 55 µL of aptamer/primer mix was added to a microtiter plate (Hybaid # AB-0407) and sealed with foil. Test samples were prepared in a microtiter plate by mixing known concentrations of protein analytes in SB17T and diluting serially with SB17T.

B. Sample Equilibration

55 µL of aptamer/primer mix was added to 55 µL of test sample and incubated at 37° C. for 15 minutes in a foil-sealed microtiter plate. The final concentration of each aptamer in the equilibration mixture was 0.5 nM. After equilibration, all subsequent steps of this method were performed at room temperature unless otherwise noted.

C. Aptamer Capture and Free Protein Removal

A DuraPore filtration plate (Millipore HV cat# MAHVN4550) was washed once with 100 μL 1× SB17T by vacuum filtration, 133.3 μL 7.5% Streptavidin-agarose resin (Pierce) was added to each well and washed twice with 200 μL 1× SB17T. 100 μL of equilibrated samples was transferred to the Durapore plate containing the Streptavidin-agarose resin and incubated on a thermomixer (Eppendorf) at 800 rpm for 5 minutes. The resin was washed once with 200 μL 1× SB17T+100 μM biotin and once with 200 μL 1× SB17T.

D. Protein Tagging with Biotin

100 μL of 1.2 mM NHS-PEO4-biotin in SB17T, prepared immediately before use, was added to the resin with captured aptamer and aptamer:protein complexes and incubated on a thermomixer at 800 rpm for 20 minutes. The resin was washed five times with 200 μL 1× SB17T by vacuum filtration.

E. Slow Off-Rate Enrichment Process & Photocleavage

The drip director was removed from underside of the DuraPore plate and the plate was placed over a 1 mL microtiter collection plate. The resin was washed once with 200 μL 1× SB17T by centrifugation at 1000×g for 30 sec. 80 μL of 1× SB17T+10 mM dextran sulfate was added to the resin and irradiated with a BlackRay Mercury Lamp on a thermomixer at 800 rpm for 10 minutes. The DuraPore plate was transferred to a new 1 mL deepwell plate and centrifuged at 1000×g for 30 seconds to collect the photocleaved aptamer and protein:aptamer complexes.

F. Protein Capture and Free Aptamer Removal

50 μL of MyOne-streptavidin C1 paramagnetic beads (Invitrogen) (10 mg/mL in 1× SB17T) was added to a microtiter plate. The beads were separated with a magnet for 60 seconds and the supernatant was removed. 225 μL of photocleavage mixture was added to the beads and mixed for 5 minutes. The beads were washed four times with 200 μL 1× SB17T by separating the magnetic beads and replacing the wash buffer. The final wash buffer was removed.

G. Aptamer Elution

100 μL Sodium Phosphate Elution Buffer (10 mM $Na_2HPO_4$, pH 11) was added to the beads and mixed for 5 minutes. 90 μL of eluate was transferred to a microtiter plate and neutralized with 10 μL Sodium Phosphate Neutralization Buffer (10 mM $NaH_2PO_4$, pH 5).

H. Aptamer Hybridization to Microarrays

DNA arrays were prepared with oligonucleotide capture probes comprised of the complementary sequence of the variable region of each aptamer immobilized on a custom microscope slide support. Multiple arrays (subarrays) exist on each slide, and subarrays were physically separated by affixing a gasket (Grace) for sample application. Arrays were pretreated with 100 μL Blocking Buffer and incubated for 15 minutes at 65° C. on a thermomixer. 30 μL of high salt Hybridization Buffer was added to 90 μL of neutralized aptamer eluate in a microtiter plate, incubated at 95° C. for 5 minutes in a thermalcycler, and cooled to 65° C. at 0.1° C./second. Blocking Buffer was removed from the arrays and 110 μL of aptamer sample was added to the arrays and incubate in a humid chamber at 65° C. for 20 hours.

I. Array Washing

Aptamer sample was removed from the arrays, and the arrays were washed once with 200 μL of sodium phosphate Tween-20 wash buffer at 65° C., with the gasket in place, and three times with 25 mL sodium phosphate, Tween-20 wash buffer at 65° C. in a pap jar with the gasket removed. Arrays were dried with a nitrogen gun.

J. Quantitate Signal on Arrays

Array slides were scanned on a TECAN LS300 Reloaded. in an appropriate channel for Cy3 detection and Cy3 signal on each array feature is quantified.

Figure 12A:
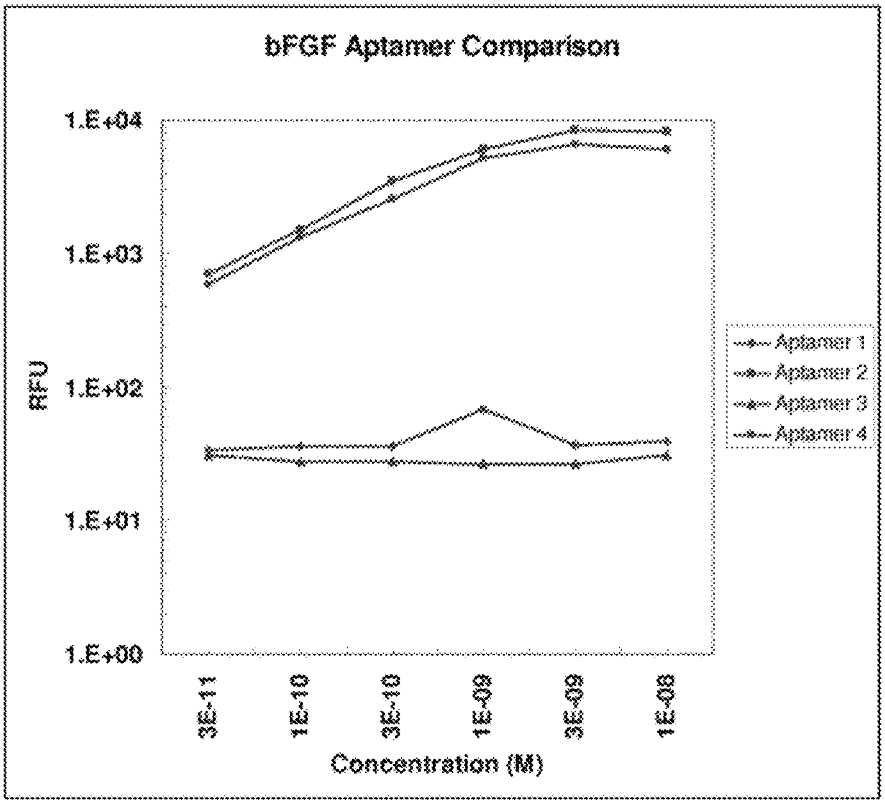
FIGS. 12A to 12C illustrate dose response curves for slow off-rate aptamers versus traditional aptamers for three different targets.
Figure 12B:
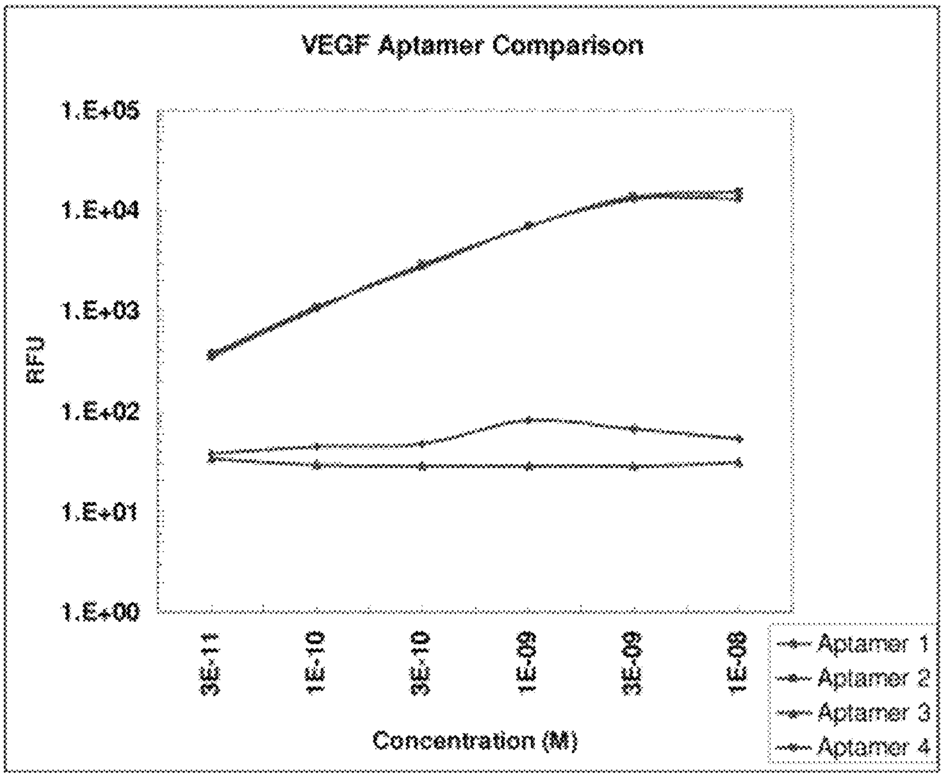
Figure 12C:
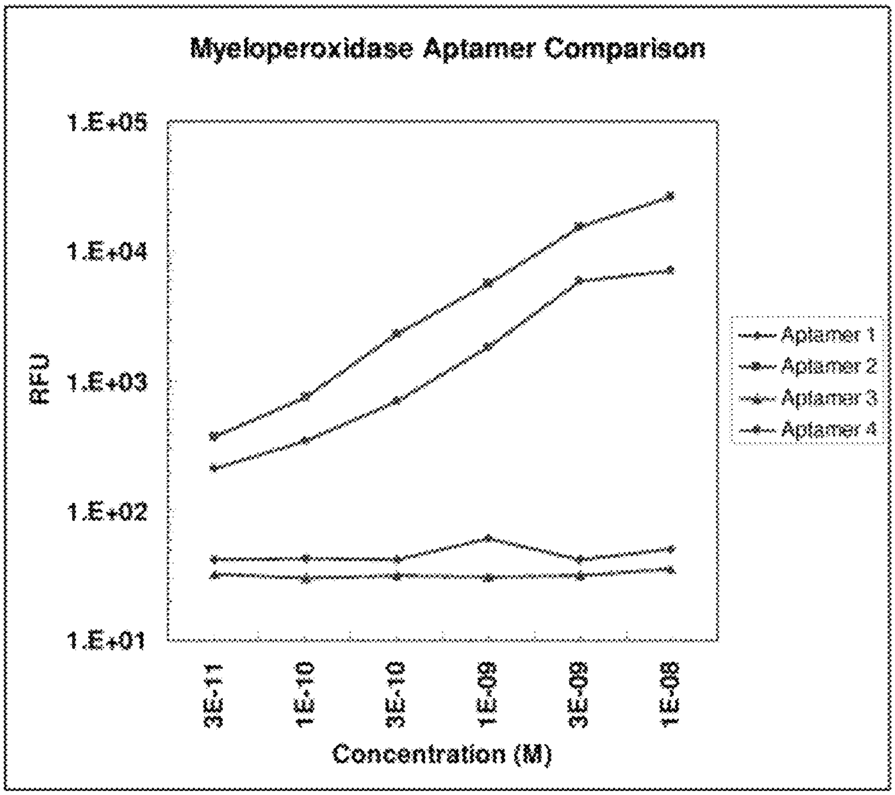

Results:

Aptamers specific to three different targets (bFGF, VEGF, and Myeloperoxidase) were produced using traditional SELEX methods and materials. A second set of aptamers specific to the same set of targets were made using 5-position modified nucleotides and selected for very slow off-rates for their respective targets. Aptamers made in the traditional process had measured off-rates on the order of less than 5 minutes. Aptamers made with the modified nucleotides and using slow off-rate enrichment process during selection had off-rates of greater than 20 minutes. Two sets of aptamers were made for each target by the two different methods for a total of 4 different aptamer populations for each target. The ability of these aptamer populations to measure analyte concentrations in test samples was evaluated as described above over a range of target concentrations. Relative signal from the DNA chip detection was plotted against the input target concentration. See FIGS. 12A to 12C. The response curve of the traditional aptamers is very flat and the sensitivity of the detection is fairly low. The sensitivity of detection of the respective targets with the slow off-rate aptamers is excellent. The data supports the need to use the slow off-rate aptamers for maximum analytic performance.

Example 8

Generation of High Affinity BndU Aptamers to Human Thrombin

A. Preparation of Candidate Mixture

A candidate mixture containing dATP, dCTP, dGTP, and BndUTP was prepared by polymerase extension of a primer with a 5' ANA chromophore and purified as described in Example 3.

B. Preparation of Target Protein

Human thrombin was tagged with biotin as describe in Example 2.

C. Aptamer Selection with Slow Off-Rate Enrichment and Photocrosslinking

Aptamer selection was performed as described in Example 3 with biotinylated human thrombin as the target.

D. Aptamer Amplification and Purification

Amplification and purification were performed as described in Example 3.

E. Selection Stringency and Feedback

Selection stringency and feedback were performed as described in Example 3.

F. Aptamer Properties

Figure 15:
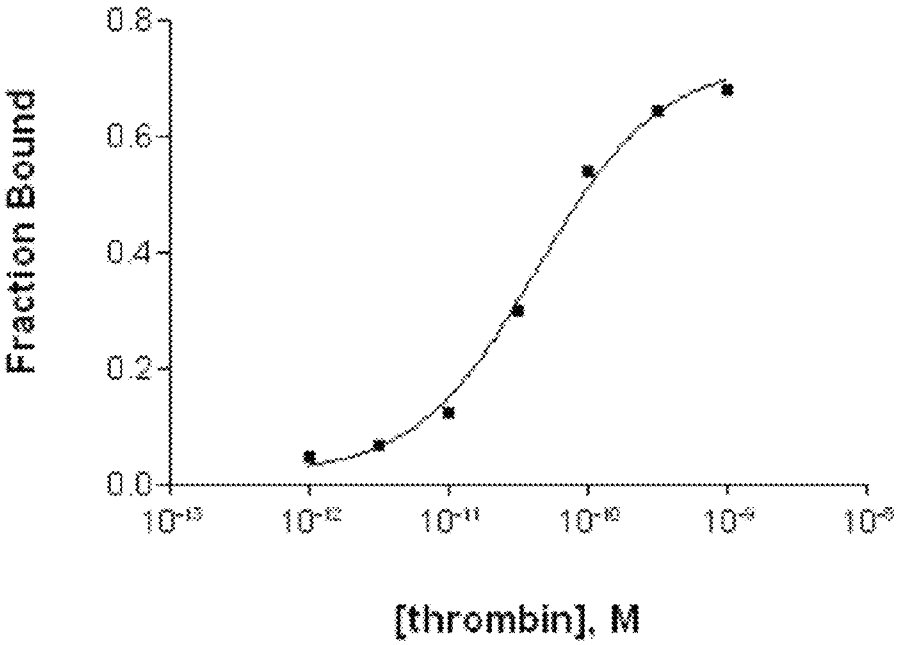
FIG. 15 illustrates a plot used in the determination of the binding constant for a slow off-rate aptamer containing C-5 modified pyrimidines to thrombin.

The equilibrium binding constant ($K_d$) of aptamer 2336-17 from this selection with a modified BndU was $4.4.\times10^{-11}$ M (measured according to the protocol described in Example 1) as demonstrated in FIG. 15.

In the art, single-stranded DNA aptamers to human thrombin were selected from a library comprised of natural dA, dC, dG, and dT nucleotides (Bock, et al., "Selection of Single-Stranded DNA Molecules that Bind and Inhibit Human Thrombin," Nature (1992) 355:564-566). The binding affinities of the aptamers had $K_d$ values ranging from $2.5.\times10^{-8}$ M to $2.0.\times10^{-7}$ M. Using a similar protocol with a library comprised of natural dA, dC, dG, and modified 5-(1-pentynyl)-dUTP, aptamers were selected with $K_d$ values ranging from $4.\times10^{-7}$ M to $1.\times10^{-6}$ M (Latham, et al., "The Application of a Modified Nucleotide in Aptamer Selection: Novel Thrombin Aptamers Containing 5-(1-Pentynyl)-2'-Deoxyuridine," Nucleic Acid Research (1994) 22(14): 2817-2822).

A number of patents, patent application publications, and scientific publications are cited throughout and/or listed at the end of the description. Each of these is incorporated herein by reference in their entirety. Likewise, all publications mentioned in an incorporated publication are incorporated by reference in their entirety.

Examples in cited publications and limitations related therewith are intended to be illustrative and not exclusive. Other limitations of the cited publications will become apparent to those of skill in the art upon a reading of the specification and a study of the drawings.

Example 9

Generation of High Affinity BndU Aptamers to Her2 (ErbB-2) and Histological Applications A. Preparation of Candidate Mixture A candidate mixture containing dATP, dCTP, dGTP, and BndUTP was prepared and purified as described in Example 5.

B. Immobilization of Target Proteins

A His-tagged $F_c$ fusion of the extracellular domain of HER2 was obtained from R&D Systems and was captured with Talon beads as described in Example 1.

C. Aptamer Selection with Slow Off-Rate Enrichment

Aptamer selection was performed as described in Example 5.

D. Aptamer Amplification and Purification

Amplification and purification were performed as described in Example 5.

E. Selection Stringency and Feedback

Selection stringency and feedback were performed as described in Example 5.

F. Aptamer Properties

The equilibrium binding constant ($K_d$) of aptamer 2616-24 from this selection with a modified BndU was $1.5 \times 10^{-8}$ M.

Figure 16:
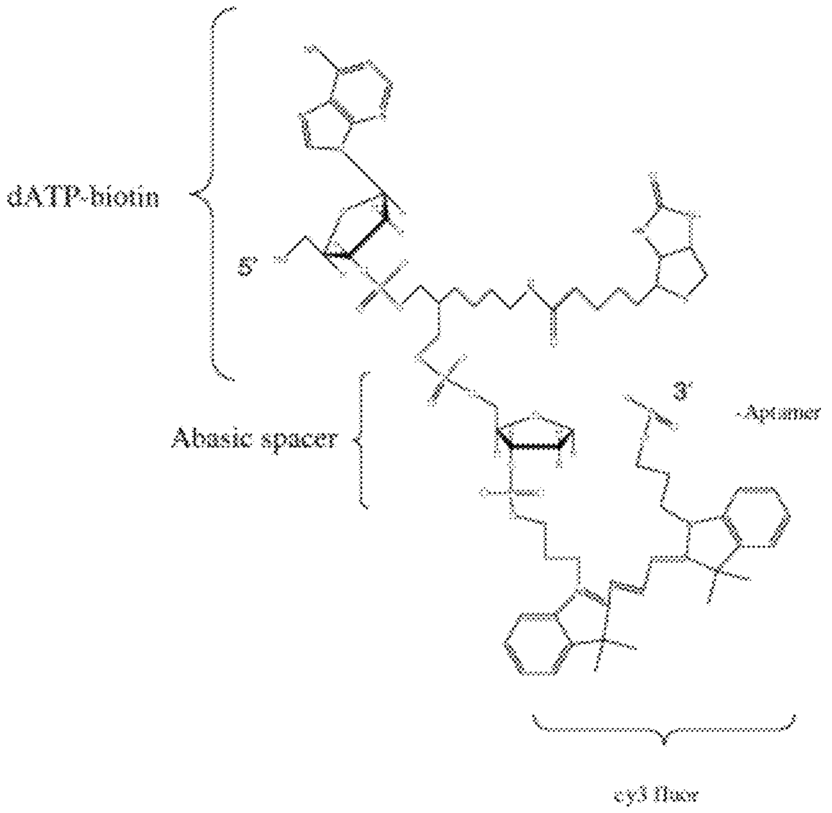
FIG. 16 illustrates an aptamer construct comprising a 5'-biotin tag, an abasic spacer and a Cy3 label. This construct was used in the synthesis of the aptamers described in Examples 9-11.

HER2 aptamer was synthesized with 5' modifications including biotin and Cy3 as shown in FIG. 16 and tested for its ability to stain HER2 protein in frozen breast carcinoma tissue sections. Deidentified tissue samples were obtained from surgical excision and autopsy specimens. Tissue was frozen immediately upon surgical excision in OCT medium, and stored at −70° C. until sectioned. Immunohistochemistry (IHC) analysis of HER2 status was performed using standard methodology by hospital pathology staff, and results were taken from the patient medical records prior to specimen deidentification. 5 μm frozen tissue sections were cut in a cryostat and immediately placed onto a charged slide (Superfrost plus), and the slide was then immersed in a fixative solution (100% ethanol or acetone) for at least 1 hour. OCT medium was removed from slides by a 2 minute rinse in deionized water, followed by 5 minute rinse in SB18 buffer (40 mM Na-HEPES, pH 7.5, 52 mM NaCl, 5 mM KCl, 5 mM $MgCl_2$, 0.05% Tween-20). 10-1000 nM Aptamer solutions made up in SB18 buffer, with or without 1 mM dextran sulfate (DS) were applied for varying times to rinsed sections and then washed for 5 minutes with SB18+/−1 mM dextran sulfate (DS). Fluorescence images were obtained with a Nikon 80i upright microscope equipped with Digital Sight DS-Ril camera, mercury lamp illumination source, and neutral density and optical filters appropriate for DAPI or Cy3 imaging. Fast nuclear Aptamer dissociation was imaged at 5 Hz. For time course experiments, trials were taken without addition of reagents to confirm that photobleaching was not a significant source of fluorescence decay over the observed time period.

Figure 17A:
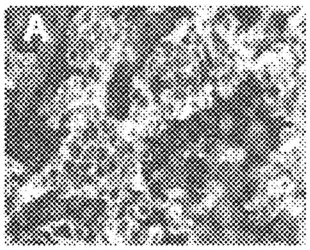
FIG. 17A illustrates HER2 positive invasive ductal carcinoma tissue stained with 100 nM Cy3-HER2 aptamer+1 nM dextran sulfate. The nuclei are counterstained with DAPI.
Figure 17B:
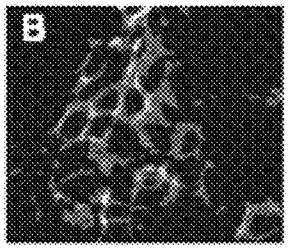
FIG. 17B illustrates magnified Cy3 channel deconvolution from the same sample as in FIG. 17A, demonstrating membranous aptamer location.
Figure 17C:
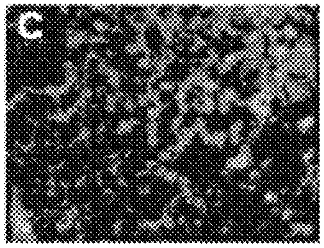
FIG. 17C illustrates HER2 negative breast tumor stained with 100 nM Cy3-HER2 aptamer+1 mM dextran sulfate. The nuclei are counterstained with DAPI.
Figure 18A:
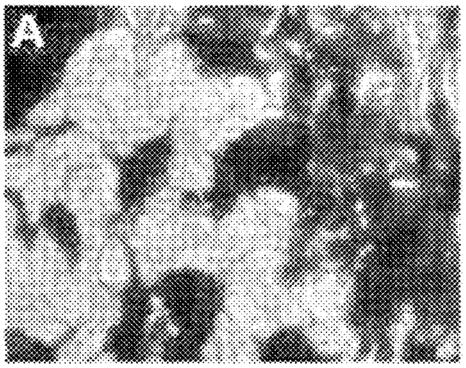
FIG. 18A illustrates HER2 positive breast carcinoma tissue stained with Cy3-HER2 aptamer in the absence of competitor.
Figure 18B:
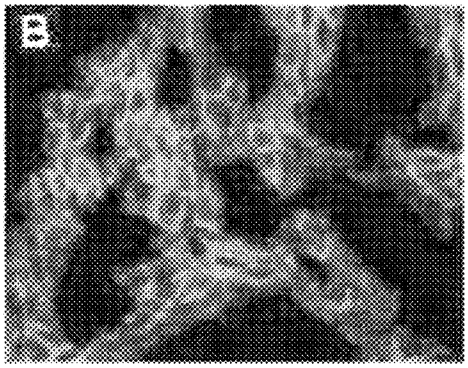
FIG. 18B illustrates the tumor tissue as in FIG. 18A, followed by a buffer wash and 30 minutes incubation with 1 mM dextran sulfate.

In the presence of 1 mM DS, the HER2 aptamer binds to cell membranes (FIG. 17A, B) in the expected morphologic pattern in frozen breast tumors that have been classified by immunohistochemistry (IHC) as having 3+ HER2 expression, but it does not bind to breast tumors classified by IHC as 0/negative, or non-breast negative control tissues (FIG. 17C). In the absence of DS, the HER2 aptamer binds to nuclei, cytoplasm, and stroma in any tissue to which it is applied, with no significant membranous localization in IHC HER2 3+ breast carcinoma tissue (FIG. 18A). Application of the HER2 aptamer alone to IHC HER2 3+ breast carcinoma tissue, followed by a buffer wash and 30 minute incubation with DS (FIG. 18B), recapitulates the staining pattern observed when DS is co-applied with the aptamer, indicating that the nonspecific binding is reversible. A scrambled oligonucleotide with the same base composition but random sequence shows only nuclear binding in breast carcinoma tissue, which can only partly be prevented or reversed with DS (not shown).

Figures 19A, 19B, 19C, 19D:
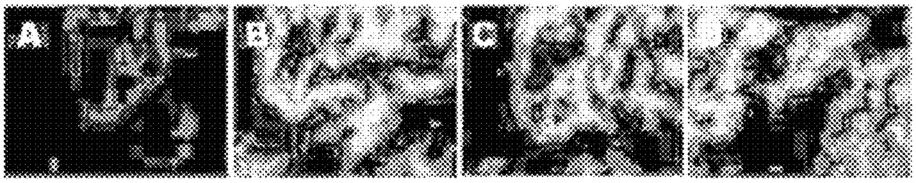
FIGS. 19A-D illustrate HER2 IHC 3+ invasive ductal carcinoma frozen sections stained with Cy3-HER2 aptamer in the presence of 1 mM dextran sulfate under the following conditions: [aptamer]=100 nM at a staining time of 1 min (FIG. 19A), 5 min (FIG. 19B) and 30 min (FIG. 19C) and at [aptamer]=1 μM at a staining time of 1 min (FIG. 19D).

The association kinetics of specific HER2 aptamer binding in frozen tissue are quite fast, saturating its target in less than 5 minutes when applied at 100 nM (FIGS. 19A-C) and less than 1 minute when applied at 1 μM (FIG. 19D). The speed and simplicity of staining indicate that a rapid assay targeting a protein with diagnostic relevance in the intraoperative setting could assist in identifying occult metastatic carcinoma in sentinel lymph nodes.

Kinetics of binding in tissue were evaluated by loading a HER2+ breast carcinoma frozen section with fluorescent HER2 aptamer in the absence of DS (generating a staining pattern as seen in FIG. 18A), washing in buffer alone, and then adding 1 mM DS in the absence of aptamer. Under these conditions, most of the nonspecific nuclear staining was lost in a matter of seconds (FIG. 20A); a small fraction of residual nuclear fluorescence, <10% of the total, decayed more slowly over 30-60 minutes, indicating that nonspecific binding occurs in at least two compartments.

In a second experiment, HER2+ breast carcinoma frozen section was incubated with fluorescent HER2 aptamer in the presence of DS (generating a staining pattern as seen in FIG. 17A), washed in buffer alone, and then 1 mM DS plus 100 nM non-fluorescent HER2 aptamer was added. Specific membranous staining was lost over 30-45 minutes, as excess non-fluorescent aptamers replaced the dissociated fluorescent aptamer (FIG. 20B). The dissociation rate of aptamer from its target in the membrane was ~100-fold slower than the dissociation rate from the non-specific binding sites in the nucleus. In both this experiment, as well as the previous experiment, tissue autofluorescence prevented the measured signal from decaying to zero.

Example 10

Generation of High Affinity BndU Aptamers to Epidermal Growth Factor Receptor (EGFR/ErbB-1) and Histological Applications A. Preparation of Candidate Mixture A candidate mixture containing dATP, dCTP, dGTP, and BndUTP was prepared and purified as described in Example 5.

B. Immobilization of Target Protein

An $F_c$ fusion of EGFR was tagged with biotin as describe in Example 2, and was captured with Streptavidin beads.

C. Aptamer Selection with Slow Off-Rate Enrichment

Aptamer selection was performed as described in Example 5.

D. Aptamer Amplification and Purification

Amplification and purification were performed as described in Example 5.

E. Selection Stringency and Feedback

Selection stringency and feedback were performed as described in Example 5.

F. Aptamer Properties

The equilibrium binding constant ($K_d$) of aptamer 3138-49 to its target protein was $1.3.\times10^{-9}$ M and the $K_d$ of aptamer 3159-1 was $1.4\times10^{-10}$ M.

Figure 21A:
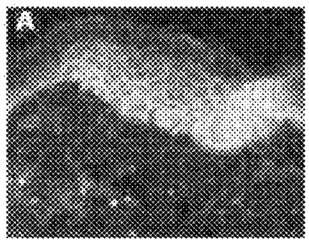
FIG. 21A illustrates normal skin stained with 100 nM Cy3 EGFR aptamer 3138-49+1 mM dextran sulfate; nuclei are counterstained with DAPI.
Figure 21B:
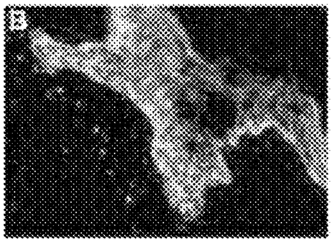
FIG. 21B illustrates normal skin stained with 100 nM Cy3 EGFR aptamer 3159-1+1 mM dextran sulfate, nuclei are counterstained with DAPI.
Figure 21C:
FIG. 21C illustrates the staining of normal skin with 100 nM biotinylated EGFR aptamer 3159-1+1 mM dextran sulfate, detected by streptavidin-horseradish peroxidase.

EGFR aptamers were synthesized with 5' modifications including biotin and Cy3 as shown in FIG. 16 and tested for its ability to stain EGFR protein in frozen human skin tissue sections. Tissue preparation and staining were as described in Example 9 except that frozen skin tissue was used instead of breast carcinoma tissue. The aptamer to EGFR behaves similarly to the HER2 aptamer, binding to nuclei in frozen normal human epidermis if applied in the absence of DS (not shown), but binding in the expected, predominantly basal epidermal membranous pattern when co-incubated (FIG. 21) or post-incubated with DS (not shown). Both direct fluorescent detection of EGFR, using Cy3 labeled aptamer (FIGS. 21A and B), and colorimetric detection using horse radish peroxidase (FIG. 21C) were demonstrated. EGFR aptamer showed no staining in a variety of tissues known to lack EGFR expression (not shown).

Example 11

Generation of High Affinity BndU Aptamers to Prostate Specific Antigen (PSA) and Histological Applications A. Preparation of Candidate Mixture A candidate mixture containing dATP, dCTP, dGTP, and BndUTP was prepared and purified as described in Example 5.

B. Immobilization of Target Protein

Native PSA purified from seminal fluid was tagged with biotin as describe in Example 2, and was captured with Streptavidin beads.

C. Aptamer Selection with Slow Off-Rate Enrichment

Aptamer selection was performed as described in Example 5.

D. Aptamer Amplification and Purification

Amplification and purification were performed as described in Example 5.

E. Selection Stringency and Feedback

Selection stringency and feedback were performed as described in Example 5.

F. Aptamer Properties

The equilibrium binding constant ($K_d$) of PSA aptamer to its target protein was $1.\times10^{-9}$M.

The PSA aptamer was synthesized with 5' modifications including biotin and Cy3 as shown in FIG. 16. Aptamer-Qdot 605 streptavidin was conjugated at a final aptamer concentration of 20 nM, with an aptamer-nanoparticle labeling ratio of 40:1 in HBS-T (40 mM HEPES pH 7.5, 120 mM NaCl, 5 mM KCl, 5 mM MgCl2, 0.05% Tween20) buffer. The mixture was incubated with shaking at 650 rpm for 60 minutes at 22° C. Reaction was quenched with 200 μg/ml d-biotin to Qdot complex (20-30 minutes). Excess biotin was removed by ultrafiltration. Aptamer staining of frozen prostate tissue was performed on 5 μm thick sections of cryosectioned OCT embedded frozen tissue on positively charged glass slides. The sectioned tissue slides were stored in acetone (or, alternatively, absolute ethanol) at 4° C. until use and with care to not let the tissue air dry. The tissue section slides were rinsed for a couple minutes in DI water to remove the OCT embedding media. A paper towel was used to dry around the section then a VectorLab ImmEdge hydrophobic barrier pen was used to draw a perimeter around the tissue section to minimize the slide assay volume. The aptamer-Qdot 605 conjugate (20 nM aptamer-Qdot, 1 mM Dextran Sulfate) was added directly to the tissue sections on slides for 60 minutes. The slides were then washed sequentially by briefly dipping each slide in HBS-T for two minutes after blotting off the aptamer staining solution. The stained slides were coverslipped with Fluoromount-G that has been supplemented with 10 mM $Mg^{2+}$ and 15 mM n-propyl gallate antifade reagent. As a comparator, immunofluorescence (IF) of prostate tissue was performed using a PSA specific fluorescent antibody (FIG. 22A). Staining with the Qdot-conjugated PSA aptamer (FIG. 22B, C) gave a comparable staining pattern to that seen with IHC. Staining was cytosolic (FIG. 22 D,E) consistent with the expected subcellular localization of PSA.

The words "comprise", "comprises", and "comprising" are to be interpreted inclusively rather than exclusively.

The invention claimed is:

1. A method for the diagnosis of a specific disease state in a tissue or cell sample comprising:

(a) contacting a tissue sample or cell sample with an aptamer, wherein the aptamer comprises at least one C-5 modified pyrimidine that increases the dissociation half-life of the aptamer compared to the aptamer without the C-5 modified pyrimidine;

(b) measuring the presence, absence or quantity of the aptamer; and (c) diagnosing the disease state of the tissue or cell based on the presence, absence or quantity of the aptamer measured.

2. The method of claim 1, wherein said tissue or cell sample is fixed by a method used for histology or cytology.

3. The method of claim 1, wherein the aptamer has a dissociation half-life from the target of from about 15 minutes and about 240 minutes.

4. The method of claim 3, wherein said aptamer has a dissociation half-life from the target selected from the group consisting of a time ≥about 15 minutes, ≥about 30 minutes, ≥about 60 minutes, ≥about 90 minutes, ≥about 120 minutes, ≥about 150 minutes, ≥about 180 minutes, ≥about 210 minutes and ≥about 240 minutes.

5. The method of claim 1, wherein said aptamer comprises a detectable moiety.

6. The method of claim 5, wherein said detectable moiety is selected from the group consisting of a dye, a quantum dot, a radiolabel, a electrochemical functional group, an enzyme, an enzyme substrate, a ligand and a receptor.

7. The method of claim 1, wherein said aptamer is a single-stranded nucleic acid or a double-stranded nucleic acid.

8. The method of claim 7, wherein said aptamer comprises DNA, RNA, or both DNA and RNA.

9. The method of claim 1, wherein said aptamer further comprises at least one additional chemical modification.

10. The method of claim 9, wherein said at least one additional chemical modification is a chemical substitution at one or more positions independently selected from a ribose position, a deoxyribose position, a phosphate position, and a base position.

11. The method of claim 1, wherein said C-5 modified pyrimidine is independently selected from the group listed in FIG. 14.

12. The method of claim 11, wherein said C-5 modified pyrimidine is independently selected from the group consisting of 5-(N-benzylcarboxyamide)-2'-deoxyuridine (BndU), 5-(N-isobutylcarboxyamide)-2'-deoxyuridine (iBudU), 5-(N-tryptaminocarboxyamide)-2'-deoxyuridine (TrpdU) and 5-(N-naphthylmethylcarboxyamide)-2'-deoxyuridine (NapdU).

13. The method of claim 1, wherein said presence, absence or quantity of the target is a marker indicative of a specific disease state or condition and wherein the presence, absence or quantity of said target in the tissue sample or cell sample provides a basis for the diagnoses of the specific disease state or facilitates selection of, or a decision regarding whether to continue, a therapeutic regimen to treat the specific disease.

14. The method of claim 1, wherein said target is selected from the group listed in FIG. 8.

15. The method of claim 14, wherein said target is selected from the group consisting of prostate specific antigen, CMBK, CEA, CA125, HPV16, HPV18, YKL-40, VEGF, ErbB-1 and HER2.

16. The method of claim 1, wherein said tissue sample is selected from the group consisting of epithelium tissue, connective tissue, cartilage tissue, bone tissue, muscle tissue, nerve tissue, blood vessel tissue, heart tissue, lymphatic system tissue, respiratory tract tissue, urinary tract tissue, endocrine system tissue, tumor tissue and reproductive system tissue.

17. The method of claim 1, wherein said cell sample is selected from the group consisting of abdominal and pelvic washings, body cavity fluids (pleural, peritoneal), urine, gastric/esophageal washings, fine needle aspirates (FNA), breast fluid, CSF, cyst fluid, synovial fluid, and bronchial washings.

18. The method of claim 1, wherein said cell sample is cultured from epithelium tissue, connective tissue, cartilage tissue, bone tissue, muscle tissue, nerve tissue, blood vessel tissue, heart tissue, lymphatic system tissue, respiratory tract tissue, urinary tract tissue, endocrine system tissue, tumor tissue, and reproductive system tissue.

19. The method of claim 1, wherein said aptamer has a dissociation half-life from said target of greater than or equal to about 30 minutes.

20. The method of claim 10, wherein said additional chemical modification is independently selected from the group consisting of a 2'-position sugar modification, a 2'-amino (2'-$NH_2$), a 2'-fluoro (2'-F), a 2'-O-methyl (2'-OMe), an 8-position purine modification, a modification at a cytosine exocyclic amine, a substitution of 5-bromouracil, a substitution of 5-bromodeoxyuridine, a substitution of 5-bromodeoxycytidine, a backbone modification, methylation, a 3' cap, and a 5' cap.

21. The method of claim 1, wherein said the aptamer is selected from a slow off-rate enrichment process, wherein the slow off-rate enrichment process is selected from incubation of a candidate mixture with a competitor molecule, dilution of a candidate mixture, or dilution of a candidate mixture in the presence of a competitor molecule.

22. The method of claim 1, further comprising a kinetic challenge at any point after (a) and before (b).

23. The method of claim 22, wherein said kinetic challenge comprises diluting the mixture containing the aptamer affinity complex and incubating the mixture containing the aptamer affinity complex for a time selected from the group consisting of greater than or equal to 30 seconds, 1 minute, 2 minutes, 3 minutes, 4 minutes, 5 minutes, 10 minutes, 30 minutes and 60 minutes.

24. The method of claim 22, wherein said kinetic challenge comprises diluting the mixture containing the aptamer affinity complex and incubating the mixture containing the aptamer affinity complex for a time such that the ratio of the measured level of aptamer affinity complex to the measured level of the non-specific complex is increased.

25. The method of claim 22, wherein said kinetic challenge comprises adding a competitor to the mixture containing the aptamer affinity complex, and incubating the mixture containing the aptamer affinity complex for a time selected from the group consisting of greater than or equal to 30 seconds, 1 minute, 2 minutes, 3 minutes, 4 minutes, 5 minutes, 10 minutes, 30 minutes, and 60 minutes.

26. The method of claim 22, wherein said kinetic challenge comprises adding a competitor to the mixture containing the aptamer affinity complex and incubating the mixture containing the aptamer affinity complex for a time such that the ratio of the measured level of aptamer affinity complex to the measured level of the non-specific complex is increased.

27. The method of claim 22, wherein said kinetic challenge comprises diluting the mixture containing the aptamer affinity complex, adding a competitor to the mixture containing the aptamer affinity complex, and incubating the mixture containing the aptamer affinity complex for a time selected from the group consisting of greater than or equal to 30 seconds, 1 minute, 2 minutes, 3 minutes, 4 minutes, 5 minutes, 10 minutes, 30 minutes, and 60 minutes.

28. The method of claim 22, wherein said kinetic challenge comprises diluting the mixture containing the aptamer affinity complex, adding a competitor to the mixture containing the aptamer affinity complex and incubating the mixture containing the aptamer affinity complex for a time such that the ratio of the measured level of aptamer affinity complex to the measured level of the non-specific complex is increased.

29. The methods of claim 22, wherein the kinetic challenge comprises the introduction of a competitor molecule and said competitor molecule is selected from the group consisting of an oligonucleotide, heparin, herring sperm DNA, salmon sperm DNA, dextran sulfate, polyanion, abasic phosphodiester polymer, dNTP, and pyrophosphate.

* * * * *

SEQUENCE LISTING

<160> NUMBER OF SEQ ID NOS: 23

<210> SEQ ID NO 1
<211> LENGTH: 79
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (23)..(62)
<223> OTHER INFORMATION: n is a, c, g, or t

<400> SEQUENCE: 1
ababgtcttc ttgtcgtttc gcnnnnnnnn nnnnnnnnnn nnnnnnnnnn nnnnnnnnnn 60
nnggtggagt gtggtgagg 79

<210> SEQ ID NO 2
<211> LENGTH: 25
<212> TYPE: DNA
<213> ORGANISM: Artificial
<220> FEATURE:
<223> OTHER INFORMATION: Synthetic

<400> SEQUENCE: 2
atatatatcc tcaccacact ccacc 25

<210> SEQ ID NO 3
<211> LENGTH: 30
<212> TYPE: DNA
<213> ORGANISM: Artificial
<220> FEATURE:
<223> OTHER INFORMATION: Synthetic

<400> SEQUENCE: 3
ababtttttt ttgtcttctt gtcgtttcgc 30

<210> SEQ ID NO 4
<211> LENGTH: 78
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (22)..(61)
<223> OTHER INFORMATION: n is a, c, g, or t

<400> SEQUENCE: 4
ababccgtcc tcctctccgt cnnnnnnnnn nnnnnnnnnn nnnnnnnnnn nnnnnnnnnn 60
ngggacactg ggtgcagg 78

<210> SEQ ID NO 5
<211> LENGTH: 25
<212> TYPE: DNA
<213> ORGANISM: Artificial
<220> FEATURE:
<223> OTHER INFORMATION: Synthetic

<400> SEQUENCE: 5
atatatatcc tgcacccagt gtccc 25

<210> SEQ ID NO 6
<211> LENGTH: 29
<212> TYPE: DNA
<213> ORGANISM: Artificial
<220> FEATURE:
<223> OTHER INFORMATION: Synthetic

<400> SEQUENCE: 6
ababtttttt ttccgtcctc ctctccgtc 29

<210> SEQ ID NO 7
<211> LENGTH: 18
<212> TYPE: DNA
<213> ORGANISM: Artificial
<220> FEATURE:
<223> OTHER INFORMATION: Synthetic

<400> SEQUENCE: 7
gtcttcttgt cgtttcgc 18

<210> SEQ ID NO 8
<211> LENGTH: 76
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (20)..(59)
<223> OTHER INFORMATION: n is a, c, g, or t

<400> SEQUENCE: 8
ababcccgct cgtcgtctgn nnnnnnnnnn nnnnnnnnnn nnnnnnnnnn nnnnnnnnnc 60
aggcagacgg tcactc 76

<210> SEQ ID NO 9
<211> LENGTH: 25
<212> TYPE: DNA
<213> ORGANISM: Artificial
<220> FEATURE:
<223> OTHER INFORMATION: Synthetic

<400> SEQUENCE: 9
atatatatga gtgaccgtct gcctg 25

<210> SEQ ID NO 10
<211> LENGTH: 25
<212> TYPE: DNA
<213> ORGANISM: Artificial
<220> FEATURE:
<223> OTHER INFORMATION: Synthetic

<400> SEQUENCE: 10
atatatatga gtgaccgtct gcctg 25

<210> SEQ ID NO 11
<211> LENGTH: 25
<212> TYPE: DNA
<213> ORGANISM: Artificial
<220> FEATURE:
<223> OTHER INFORMATION: Synthetic

<400> SEQUENCE: 11
atatatatga gtgaccgtct gcctg 25

<210> SEQ ID NO 12
<211> LENGTH: 25
<212> TYPE: DNA
<213> ORGANISM: Artificial
<220> FEATURE:
<223> OTHER INFORMATION: Synthetic

<400> SEQUENCE: 12
atatatatga gtgaccgtct gcctg 25

<210> SEQ ID NO 13
<211> LENGTH: 25
<212> TYPE: DNA
<213> ORGANISM: Artificial
<220> FEATURE:
<223> OTHER INFORMATION: Synthetic

<400> SEQUENCE: 13
atatatatga gtgaccgtct gcctg 25

-continued

```
<210> SEQ ID NO 14
<211> LENGTH: 23
<212> TYPE: DNA
<213> ORGANISM: Artificial
<220> FEATURE:
<223> OTHER INFORMATION: Synthetic

<400> SEQUENCE: 14

ttttttttcc cgctcgtcgt ctg                                               23

<210> SEQ ID NO 15
<211> LENGTH: 27
<212> TYPE: DNA
<213> ORGANISM: Artificial
<220> FEATURE:
<223> OTHER INFORMATION: Synthetic

<400> SEQUENCE: 15

ababtttttt ttcccgctcg tcgtctg                                           27

<210> SEQ ID NO 16
<211> LENGTH: 79
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (23)..(62)
<223> OTHER INFORMATION: n is a, c, g, or t

<400> SEQUENCE: 16

ababgtgtct gtctgtgtcc tcnnnnnnnn nnnnnnnnnn nnnnnnnnnn nnnnnnnnnn       60

nnggtggagt gtggtgagg                                                    79

<210> SEQ ID NO 17
<211> LENGTH: 25
<212> TYPE: DNA
<213> ORGANISM: Artificial
<220> FEATURE:
<223> OTHER INFORMATION: Synthetic

<400> SEQUENCE: 17

atatatatcc tcaccacact ccacc                                             25

<210> SEQ ID NO 18
<211> LENGTH: 25
<212> TYPE: DNA
<213> ORGANISM: Artificial
<220> FEATURE:
<223> OTHER INFORMATION: Synthetic

<400> SEQUENCE: 18

atatatatcc tcaccacact ccacc                                             25

<210> SEQ ID NO 19
<211> LENGTH: 25
<212> TYPE: DNA
<213> ORGANISM: Artificial
<220> FEATURE:
<223> OTHER INFORMATION: Synthetic

<400> SEQUENCE: 19

atatatatcc tcaccacact ccacc                                             25
```

-continued

<210> SEQ ID NO 20
<211> LENGTH: 25
<212> TYPE: DNA
<213> ORGANISM: Artificial
<220> FEATURE:
<223> OTHER INFORMATION: Synthetic

<400> SEQUENCE: 20
atatatatcc tcaccacact ccacc 25

<210> SEQ ID NO 21
<211> LENGTH: 25
<212> TYPE: DNA
<213> ORGANISM: Artificial
<220> FEATURE:
<223> OTHER INFORMATION: Synthetic

<400> SEQUENCE: 21
atatatatcc tcaccacact ccacc 25

<210> SEQ ID NO 22
<211> LENGTH: 26
<212> TYPE: DNA
<213> ORGANISM: Artificial
<220> FEATURE:
<223> OTHER INFORMATION: Synthetic

<400> SEQUENCE: 22
ttttttttgt gtctgtctgt gtcctc 26

<210> SEQ ID NO 23
<211> LENGTH: 30
<212> TYPE: DNA
<213> ORGANISM: Artificial
<220> FEATURE:
<223> OTHER INFORMATION: Synthetic

<400> SEQUENCE: 23
ababtttttt ttgtgtctgt ctgtgtcctc 30